US007111346B2

(12) United States Patent
Inman et al.

(10) Patent No.: US 7,111,346 B2
(45) Date of Patent: Sep. 26, 2006

(54) RECIPROCATING MOVEMENT PLATFORM FOR THE EXTERNAL ADDITION OF PULSES OF THE FLUID CHANNELS OF A SUBJECT

(75) Inventors: D. Michael Inman, Miami Shores, FL (US); Marvin A. Sackner, Miami, FL (US)

(73) Assignee: Non-Invasive Monitoring Systems, Inc., North Bay Village, FL (US)

( * ) Notice: Subject to any disclaimer, the term of this patent is extended or adjusted under 35 U.S.C. 154(b) by 111 days.

(21) Appl. No.: 10/439,957

(22) Filed: May 15, 2003

(65) Prior Publication Data

US 2003/0236476 A1 Dec. 25, 2003

Related U.S. Application Data

(60) Provisional application No. 60/380,790, filed on May 15, 2002.

(51) Int. Cl.
*A61B 5/00* (2006.01)
*A61G 7/00* (2006.01)

(52) U.S. Cl. ...................... 5/600; 5/109; 5/648; 601/24

(58) Field of Classification Search .................... 5/108, 5/109, 648–651, 624; 601/51, 98, 116, 24, 601/49; 128/882
See application file for complete search history.

(56) References Cited

U.S. PATENT DOCUMENTS

| | | | | | |
|---|---|---|---|---|---|
| 30,588 | A | | 11/1860 | Pitts | |
| 2,235,184 | A | | 3/1941 | Wettlaufer | |
| 2,570,676 | A | * | 10/1951 | Henderson | 601/98 |
| 2,591,212 | A | | 4/1952 | Stauffer | |
| 2,641,252 | A | * | 6/1953 | Hemming | 601/98 |
| 2,959,169 | A | | 11/1960 | Bless | |
| 3,014,478 | A | | 12/1961 | Ware | |
| 3,021,837 | A | | 2/1962 | Newell | |
| 3,056,144 | A | * | 10/1962 | McKinley | 5/109 |
| 3,311,935 | A | | 4/1967 | Petty | |
| 3,441,014 | A | * | 4/1969 | Ramsey | 601/98 |
| 3,654,918 | A | * | 4/1972 | Blok et al. | 601/98 |
| 3,752,154 | A | | 8/1973 | Clark | |
| 4,258,446 | A | * | 3/1981 | McAllister et al. | 5/109 |
| 4,430,992 | A | | 2/1984 | Christ | |
| 4,483,327 | A | * | 11/1984 | Graham et al. | 601/26 |

(Continued)

OTHER PUBLICATIONS

International Search Report dated Dec. 2, 2003 for International Application No. PCT/US03/15605.

*Primary Examiner*—Michael Trettel
(74) *Attorney, Agent, or Firm*—Cohen, Pontani, Lieberman & Pavane

(57) ABSTRACT

An apparatus for providing medical treatments is disclosed. In one aspect, an apparatus according the present invention comprises a mattress, a mattress support, cast shoes, a footboard support, a drive for causing the reciprocating movement, and a box frame to contain and support the reciprocating movement platform. In another aspect, an apparatus according to the present invention comprises a sling device connected to a drive causing the reciprocating movement, and a box frame to contain and support the reciprocating movement platform. In yet another aspect, medical treatments by externally applying periodic acceleration according to the present invention include the treatment of inflammatory diseases, the preconditioning or conditioning of vital organs to protect them from the deleterious effects of ischemia, non-invasive ventilation and cardiopulmonary resuscitation, treatment and preconditioning of the organs of animals such as horses, and the treatment of diseases or conditions where oxidative stress plays a role.

64 Claims, 39 Drawing Sheets

U.S. PATENT DOCUMENTS

| | | | | |
|---|---|---|---|---|
| 4,934,997 | A * | 6/1990 | Skakas | 600/26 |
| 6,468,236 | B1 | 10/2002 | Sumanac | |
| 6,682,495 | B1 * | 1/2004 | Park | 601/98 |
| 6,851,144 | B1 * | 2/2005 | Wang | 5/610 |

* cited by examiner

FIG. 4A
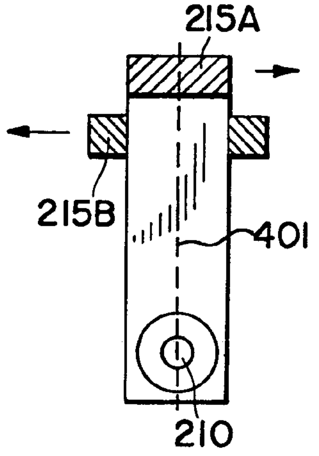
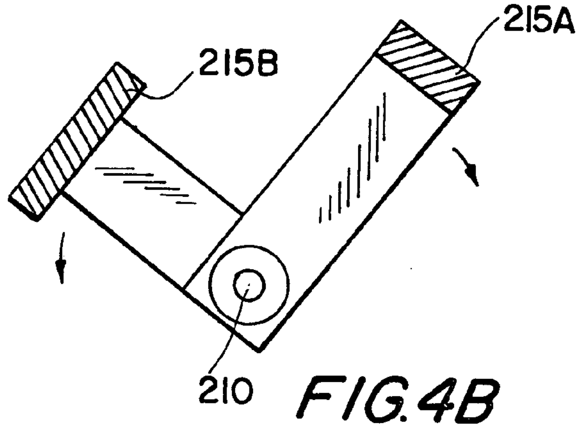
FIG. 4B
FIG. 4C
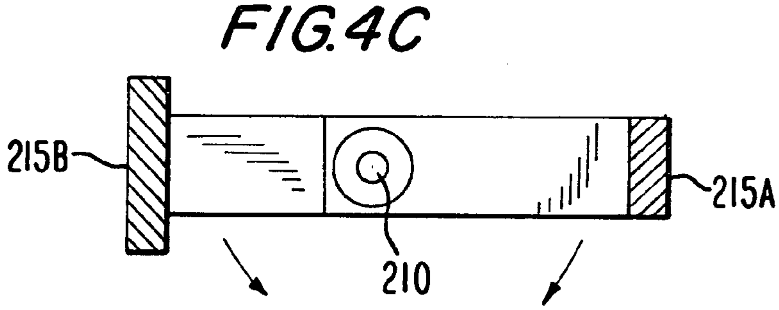
FIG. 4D
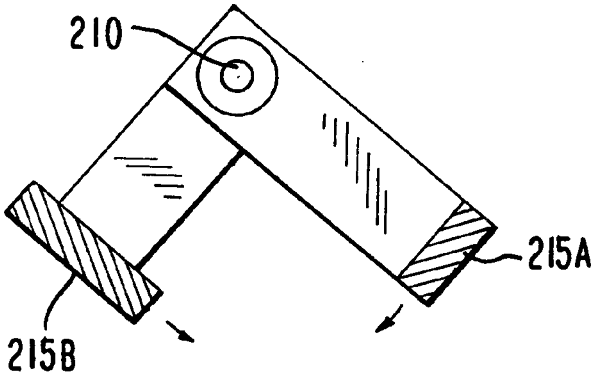
FIG. 4E
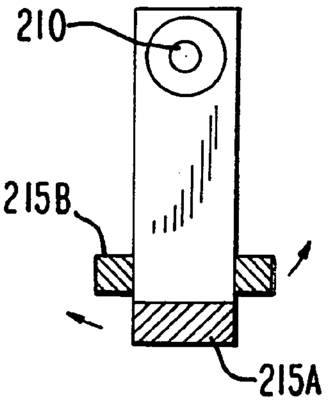

BEAT FREQUENCY & CYCLIC MOVEMENT OF DICROTIC NOTCH OF DIGITAL PULSE DURING AT 101 TREATMENT

SINGLE 1-HOUR PRETREATMENT WITH pGz OF ANTIGEN CHALLENGED ALLERGIC SHEEP

*PD400 INDICATES PROVOCATIVE DOSE OF CARBACHOL AEROSOL THAT INCREASES PULMONARY RESISTANCE BY 400%; A BREATH UNIT IS EQUIVALENT TO 1 BREATH OF 1% CARBACHOL.

* PD400 INDICATES PROVOCATIVE DOSE OF CARBACHOL AEROSOL THAT INCREASES PULMONARY RESISTANCE BY 400%; A BREATH UNIT IS EQUIVALENT TO 1 BREATH OF 1% CARBACHOL.

** L-NAME 25 MG/KG I.V. 30 MINUTES PRIOR TO pGz.

THREE DAYS, TWO 1-HOUR pGz TREATMENTS/DAY, ONE 1 HOUR PRETEATMENT WITH pGz ON DAY 4 IN ANTIGEN CHALLENGED ALLERGIC SHEEP

*PD400 INDICATES PROVOCATIVE DOSE OF CARBACHOL AEROSOL THAT INCREASES PULMONARY RESISTANCE BY 400%; A BREATH UNIT IS EQUIVALENT TO 1 BREATH OF 1% CARBACHOL.

RECIPROCATING MOVEMENT PLATFORM FOR THE EXTERNAL ADDITION OF PULSES OF THE FLUID CHANNELS OF A SUBJECT

RELATED APPLICATIONS

This application claims priority under 35 U.S.C. §119(e) from U.S. Provisional Patent Application Ser. No. 60/380,790 which was filed on May 15, 2002 and is hereby incorporated in its entirety.

BACKGROUND OF THE INVENTION

1. Field of the Invention

The present invention relates generally to a reciprocating motion platform for oscillating a subject in a back and forth, headward to footward manner in order to externally add pulses to the fluid channels of the subject. The external addition of pulses caused by the periodic acceleration of the subject results in many therapeutic benefits.

2. Description of the Related Art

This application builds on the work previously done in this field by Non-Invasive Monitoring Systems, Inc., located at 1666 Kennedy Causeway, Suite 400 in North Bay Village, Fla., as exemplified in U.S. Pat. No. 6,155,976 to Sackner et al. entitled "Reciprocating Movement Platform For Shifting Subject To and Fro in Headwards-Footwards Direction" (hereinafter referred to as the '976 patent) and U.S. patent application Ser. No. 09/967,422 written by the same inventors of the present application, entitled "External Addition of Pulses To Fluid Channels Of Body To Release Or Suppress Endothelial Mediators And To Determine Effectiveness Of Such Intervention" (hereinafter referred to as the '422 application). Both of the '976 patent and the '422 application are hereby incorporated by reference.

The '976 patent describes a reciprocating movement platform which can be used in medical treatments based on the external addition of pulses, whereas the '422 application is mainly concerned with describing various medical treatments based on the external addition of pulses. Although the present application builds on these two works, it is not limited by them.

SUMMARY OF THE INVENTION

It is an object of the present invention to provide a reciprocating movement platform for medical treatments based on the external addition of pulses.

The presently preferred embodiment of an apparatus of the present invention comprises a box frame, a drive module, and a support connected to the drive module. The support has a planar surface for supporting the subject, and a footboard to hold the subject's feet. The drive module provides periodic acceleration to the subject by moving in a line parallel to the planar surface of the support. Another presently preferred embodiment of an apparatus according to the present invention comprises a sling device connected to a drive causing the reciprocating movement, and a box frame to contain and support the reciprocating movement platform, where the sling is used to hold an animal subject.

The presently preferred medical treatments possible with externally applied periodic acceleration according to the present invention include the treatment of inflammatory diseases, the preconditioning or conditioning of vital organs to protect them from the deleterious effects of ischemia, non-invasive ventilation and cardiopulmonary resuscitation, treatment and preconditioning of the organs of animals such as horses, and the treatment of diseases or conditions where oxidative stress plays a role.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings:

FIGS. 4A–4E are diagrams showing the movement of a single pair of drive weights according to a preferred embodiment of the present invention;

DETAILED DESCRIPTION OF THE PRESENTLY PREFERRED EMBODIMENTS

Figure 1:
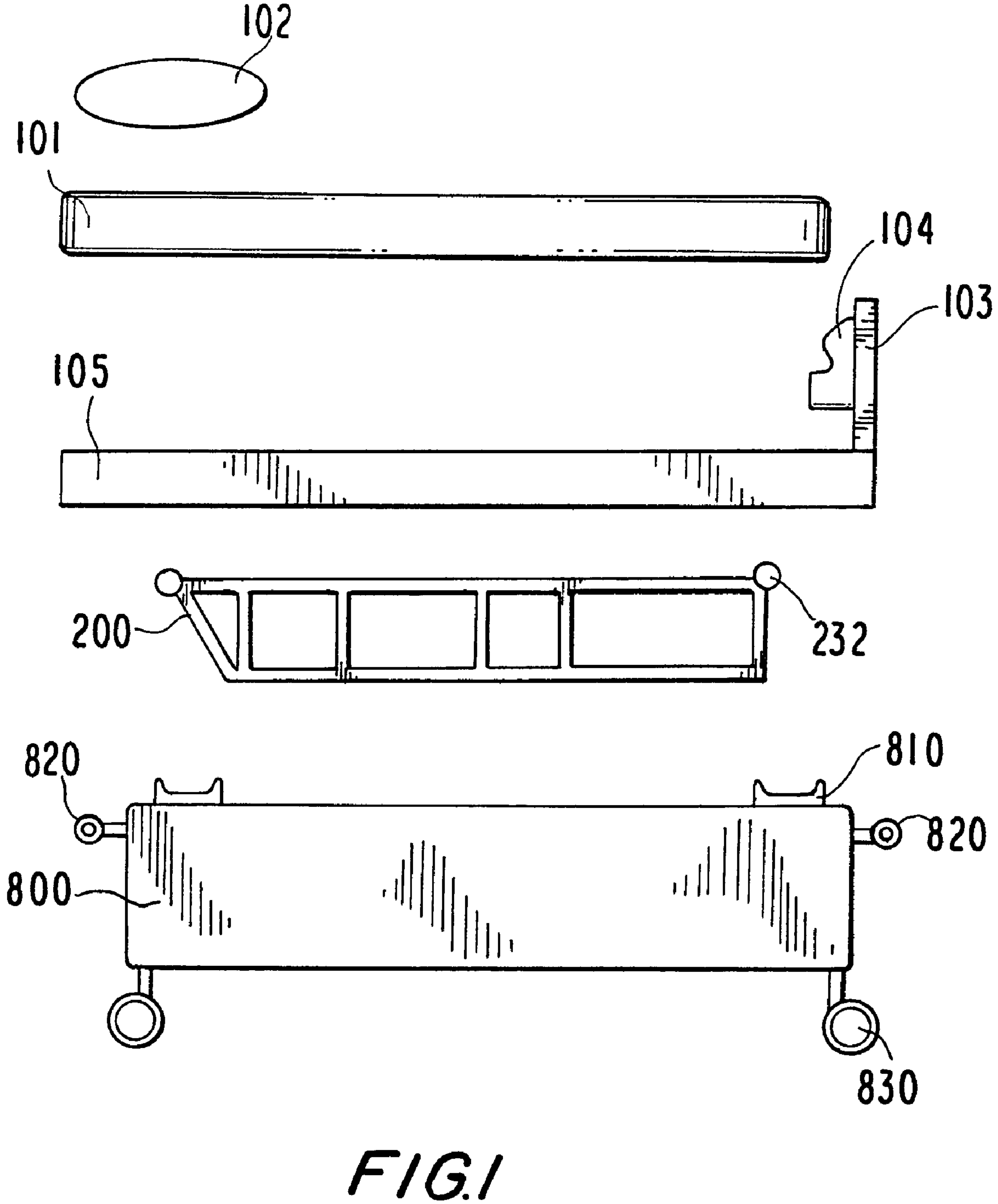
FIG. 1 is an exploded view of the components in a reciprocating movement platform according to a preferred embodiment of the present invention.

The present invention relates to both an apparatus and methods of treatment using the apparatus. This portion of the patent is broken into two sections: section I will describe some preferred embodiments of the apparatus, and section II will describe methods of treatment.

I. The Reciprocating Movement Platform

One presently preferred embodiment of the present invention comprises a reciprocating movement platform as shown in FIGS. 1, 9A, 9B, and 9C. FIGS. 1, 9A, 9B, and 9C show a completely constructed reciprocating movement platform comprised of a mattress 101 for the subject to lie upon, a pillow 102 for the subject's head, a footboard frame 103 with cast shoes 104 attached in order to secure the subject, a mattress support 105 to hold the mattress 101 and to which the footboard frame 103 is attached, a box frame 800 which holds the drive machinery (or "drive") 200 onto which the mattress support 105 is attached, bumpers 820 attached to the top and bottom of the box frame 800, and casters 830 at the four corners of the bottom of the box frame 800 for moving the reciprocating movement platform.

According to the presently preferred embodiment, the entire reciprocating movement platform system (without patient, i.e., mattress 101 and mattress support 105, footboard support 105, box frame 800, and drive machinery 200) weighs between 400 and 500 lbs. It is contemplated that future embodiments will have a reduced weight, perhaps as little as 250 lbs., for example. This will be done by replacing heavy materials, such as some of the machined metallic parts of the presently preferred embodiment, with lighter materials, such as plastic. The entire reciprocating movement platform system is 30" wide, which is the standard width of a hospital gurney, so that it may be easily moved through doorways, semi-crowded offices, etc. The length of the entire system from bumper to bumper is 88", which is as long as a standard twin or king size bed. The mattress 101 is 30" above the floor, and the top of the footboard support 103 is 42" above the floor.

According to the presently preferred embodiment, the mattress support secures the mattress by means of VELCRO strips (i.e., hook-and-loop strips). The mattress support and footboard support together weigh roughly 120 lbs. total. When assembled, the combined mattress support and footboard support are 30" wide and 82" long. The mattress is 6" thick, 30" wide, 80" long, and weighs approximately 30 lbs. The top 3" of the mattress foam is the "visco-elastic" type foam for form-fitting comfort while the subject is on the platform. The mattress can be designed to fold in half for easier transport and storage. It is contemplated that future embodiments may use a thinner and/or lighter mattress.

Figure 10:
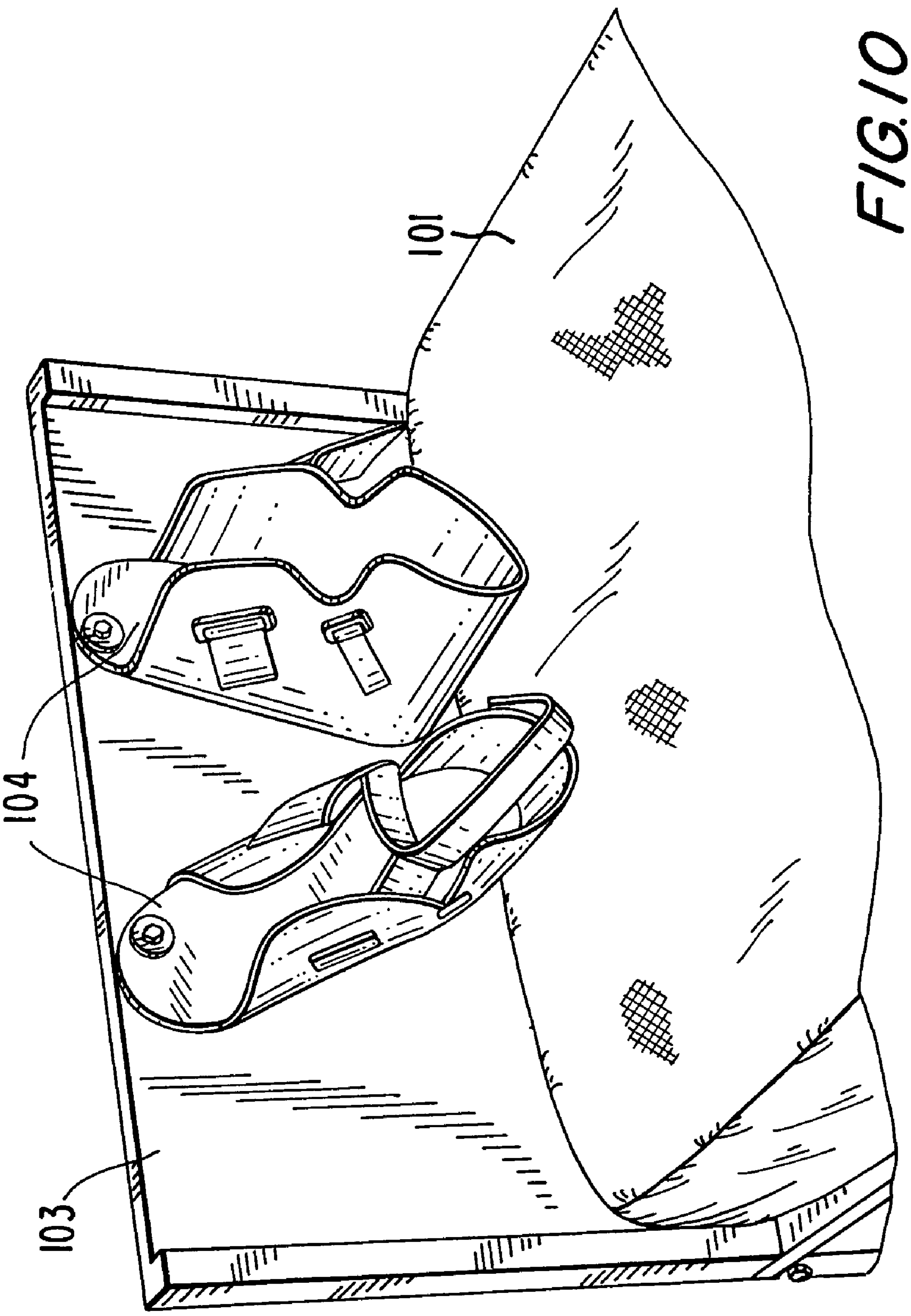
FIG. 10 shows cast shoes and a footboard support according to a preferred embodiment of the present invention.

FIG. 10 shows the cast shoes and the footboard frame to which they are attached. The cast shoes of the footboard frame are the only means by which the subject is secured to the mattress support, and thus, is the means by which the subject is "pulsed" by the reciprocating platform. The two cast shoes are rigidly attached by nuts and bolts to the footboard frame. Once the subject is lying on the mattress, he or she will put his or her feet (with shoes on) into the cast shoes and then the cast shoes will be secured around the shoes by a system of VELCRO (i.e.. hook-and-loop strips) and straps and cloth. Experiments have shown that "one size fits many", with the cast shoes servicing most adults quite adequately due to the flexibility of the VELCRO closure system. Other means of fastening the feet in the cast shoes are contemplated, such as a ski boot-like apparatus, or another fastening means, such as a snap, a buckle, a lock, etc. connection.

Figure 11:
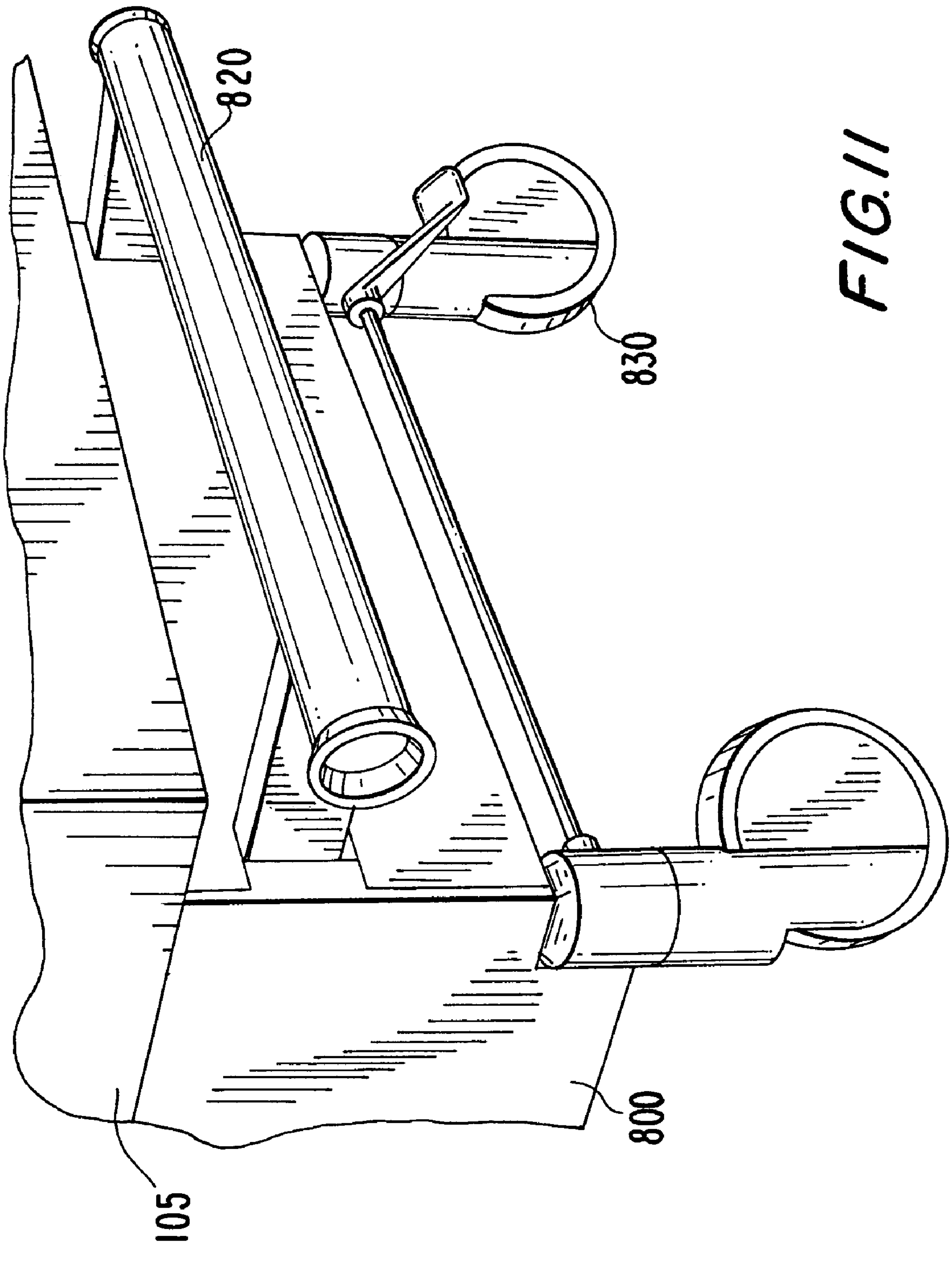
FIG. 11 shows the bottom portion of a reciprocating movement platform according to a preferred embodiment of the present invention.

FIG. 11 shows the bottom portion of the reciprocating movement platform, specifically the casters 830 and the bumper 820. The casters 830 are 6" hospital bed casters 830 with central locking features; these provide easy rolling and maneuvering, good ground clearance, easy locking (as shown by the brake petal), and an attractive appearance. The ground clearance is approximately 8", which accommodates the use of equipment (such as hoists) to lift the reciprocating movement platform. The bumpers 820 make sure the reciprocating platform is not set too close to a wall. As shown in FIG. 11, the bumper 820 extends further out than the mattress support 105. The mattress support 105 is 82" long and, when the platform is engaged in a reciprocating movement, has a range of movement of +/−2". The bumpers 820 are built to extend 1" beyond the furthest limit the mattress support 105 can travel so that the reciprocating movement platform will not be accidentally set too close to a wall where it might bump the wall during operation.

Figure 12:
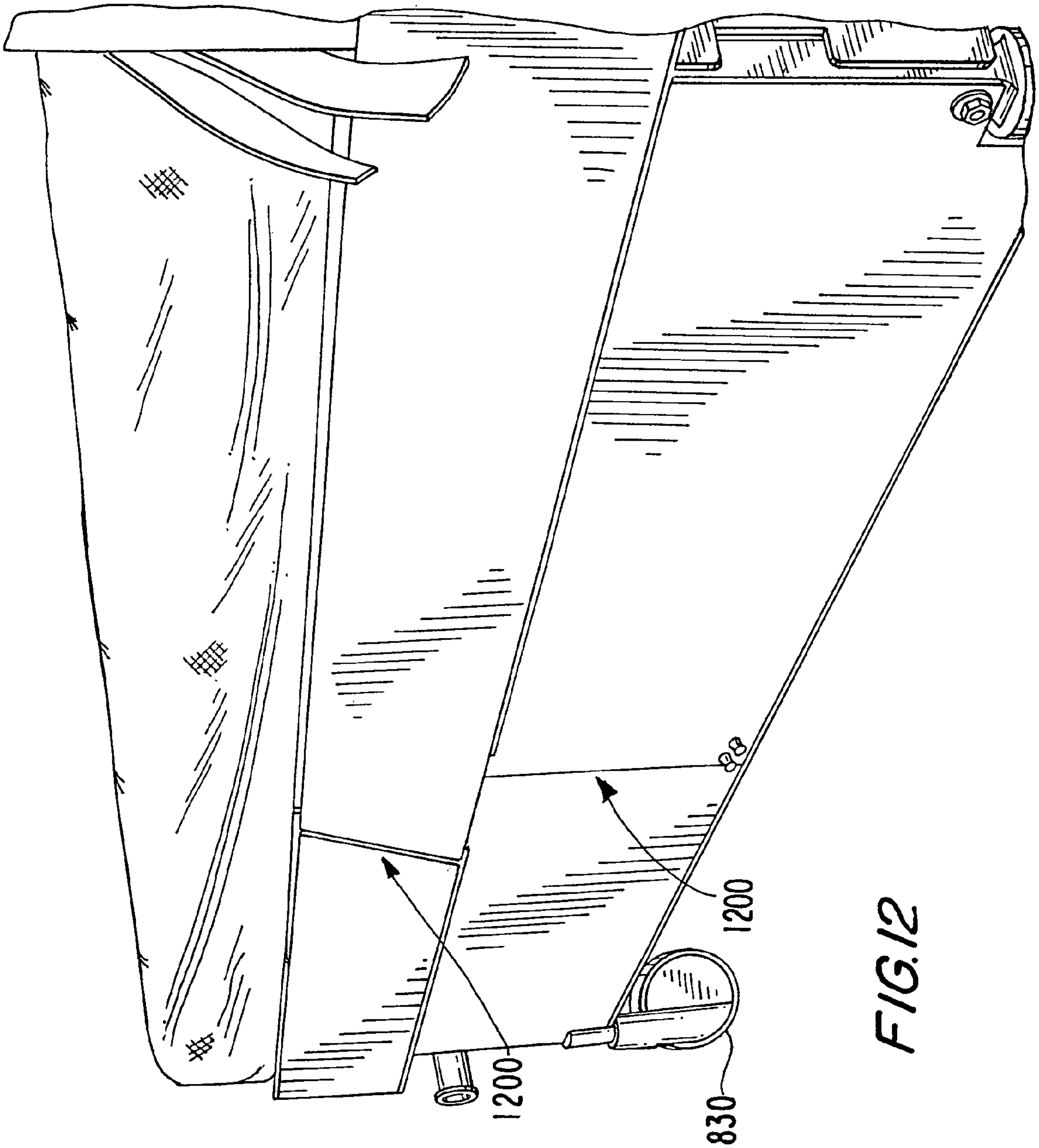
FIG. 12 shows the lines between the two halves of the mattress support and the box frame according to a preferred embodiment of the present invention.

The mattress support 105 and the box frame 800 may be built in two parts, making them easier to transport. When the two parts reach their destination, they may be attached to one another. FIG. 12 shows the thin line 1200 between the two parts after assembly. The mattress support 105 and the box frame 800 can each also be built as one solid unit and then transported. When the mattress support 105 is removed, the box frame 800 (with or without an enclosed drive 200) is only 27" wide, making it easier to transport.

The drive machinery (or "drive") is enclosed within the box frame and, as such, cannot be seen from the outside of the fully assembled movement platform. Supported by the box frame and attached to the mattress support, the drive provides the reciprocating movement of the device. The reciprocating (headwards-footwards) movement preferably has a rate of about 120–180 rpm with a force in the range of about +/−0.2 to about +/−0.3 g. The relationship between the parts can be seen in the exploded view of the reciprocating movement platform shown in FIG. 1. Starting from the top, the mattress attaches to the mattress support with VELCRO strips (i.e., hook-and-loop strips), while the footboard frame (with attached cast shoes) is bolted onto the mattress support. The mattress support is securely attached to the drive (in a manner described below). The drive has four track wheels located in the four top corners of the drive. These wheels sit in four similarly placed tracks in the box frame. Hence, the drive, mattress support, and mattress form one part of the assembled movement platform, and the only physical connection between this top part and the bottom box frame is the four wheels of the drive sitting in the four tracks of the box frame.

Figure 13:
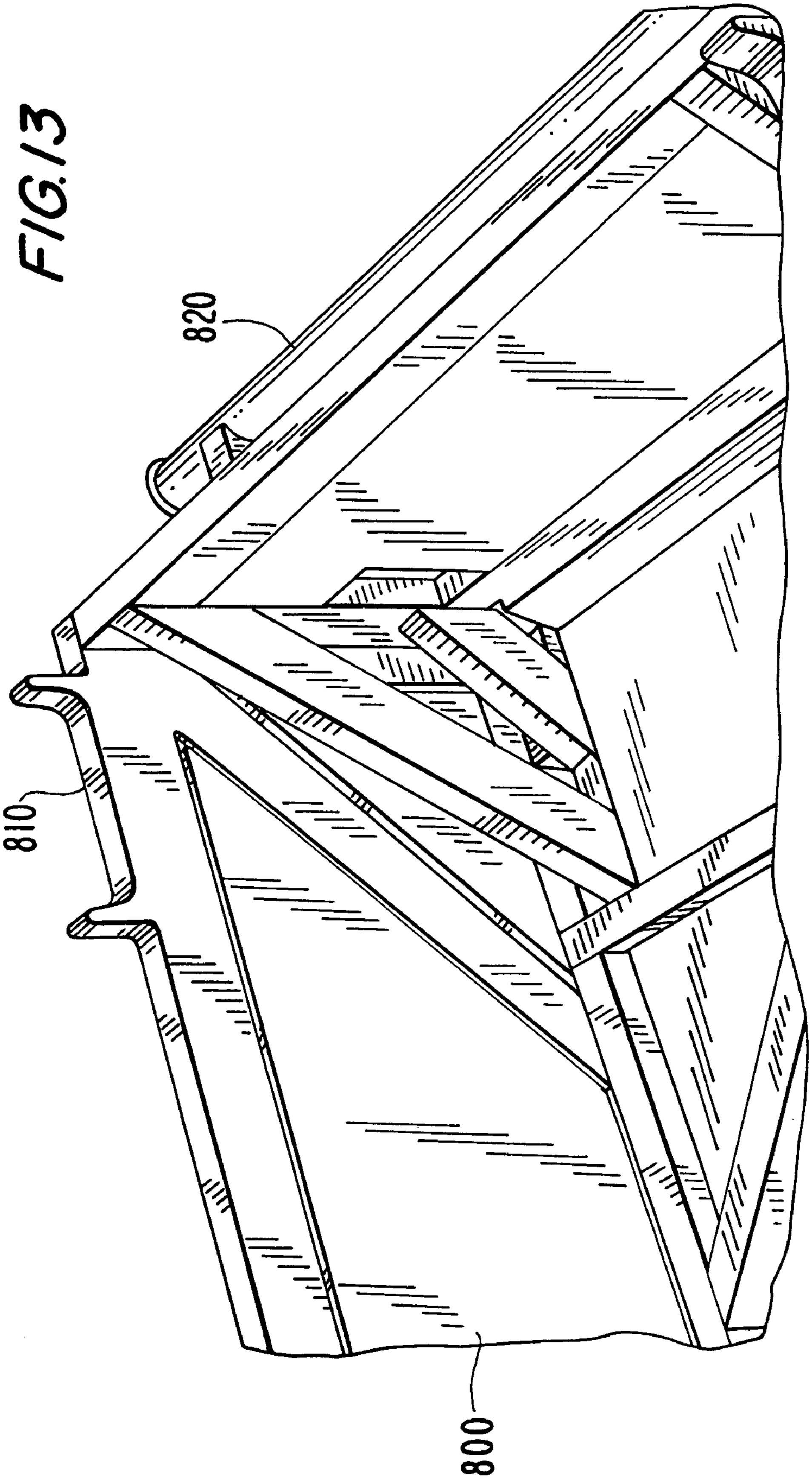
FIG. 13 shows the inside corner of a box frame (without the drive) according to a preferred embodiment of the present invention.

When the drive 200, by means which will be discussed further below, moves within the box frame 800, the wheels 232 move within the tracks, which serve to both support the drive 200 and limit the reciprocating motion of the drive 200. FIG. 13 shows the inside corner of the box frame 800 without a drive 200. The track on top of the box frame 800 has rounded ends so that the wheel 232 of the drive 200 may only move a certain distance in either direction. The track is beveled so that the track wheel 232 of the drive 200 will rest naturally in the center of the track. The track is also located near the metal support struts of the box frame 800 which thus transfer the weight of the drive 200 (and the attached mattress support 105, mattress 101, and subject) directly down to the caster 830 in the corner below.

The box frame 800 currently weighs about 120 lbs. and serves at least the following 5 purposes: 1) supporting the rest of the platform (the drive 200, mattress support 105, mattress 101, and subject); 2) providing a foundation that can be moved or anchored by means of the casters 830; 3) maintaining an adequate distance from surrounding walls by means of its bumpers 820; (4) carrying the system electronics; and (5) encasing the drive 200 for safety and noise reduction. In addition, the box frame 800 provides ground clearance for the hoist legs.

Figure 14A:
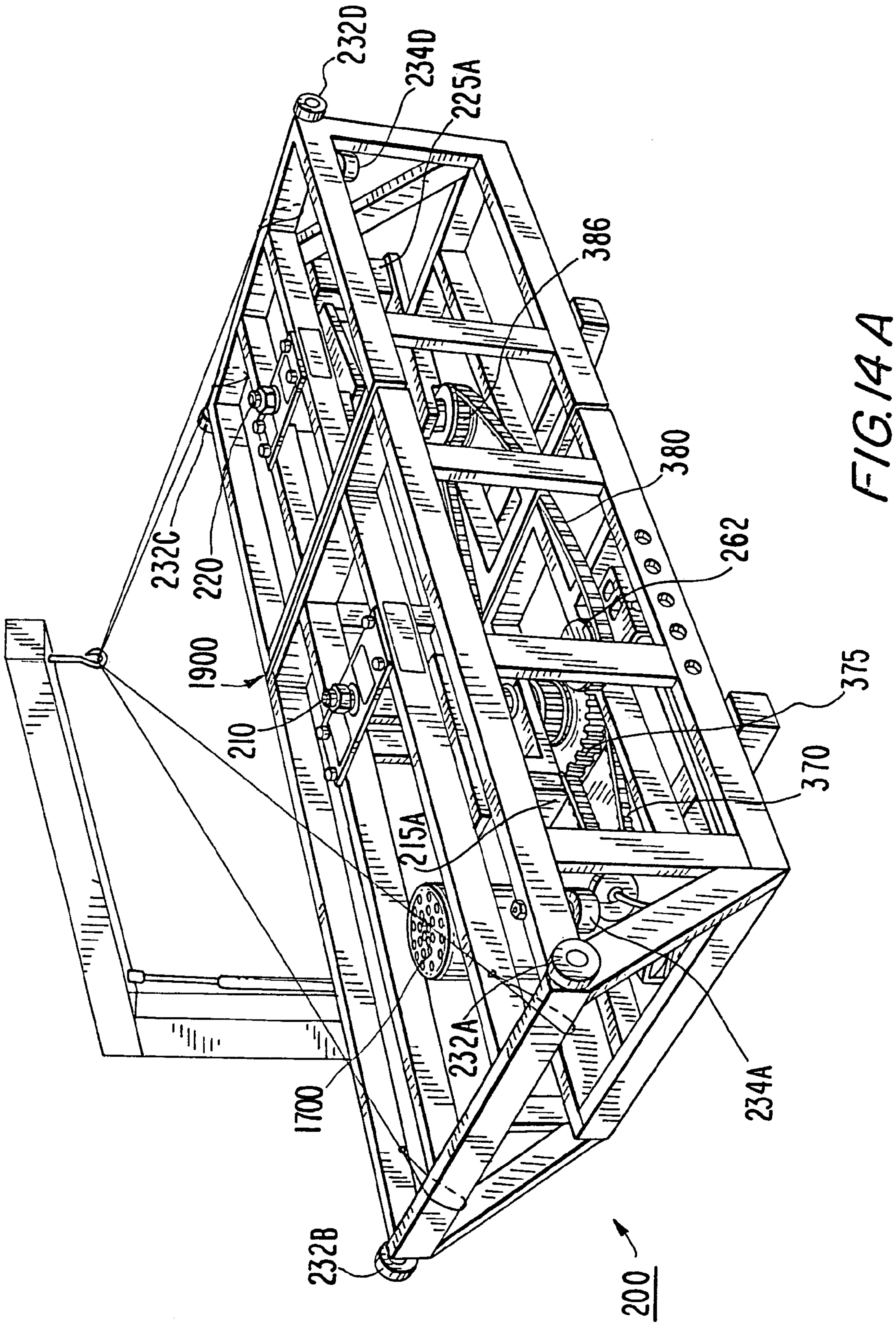
FIG. 14A shows a drive held alone and aloft, according to a preferred embodiment of the present invention.
Figure 14B:
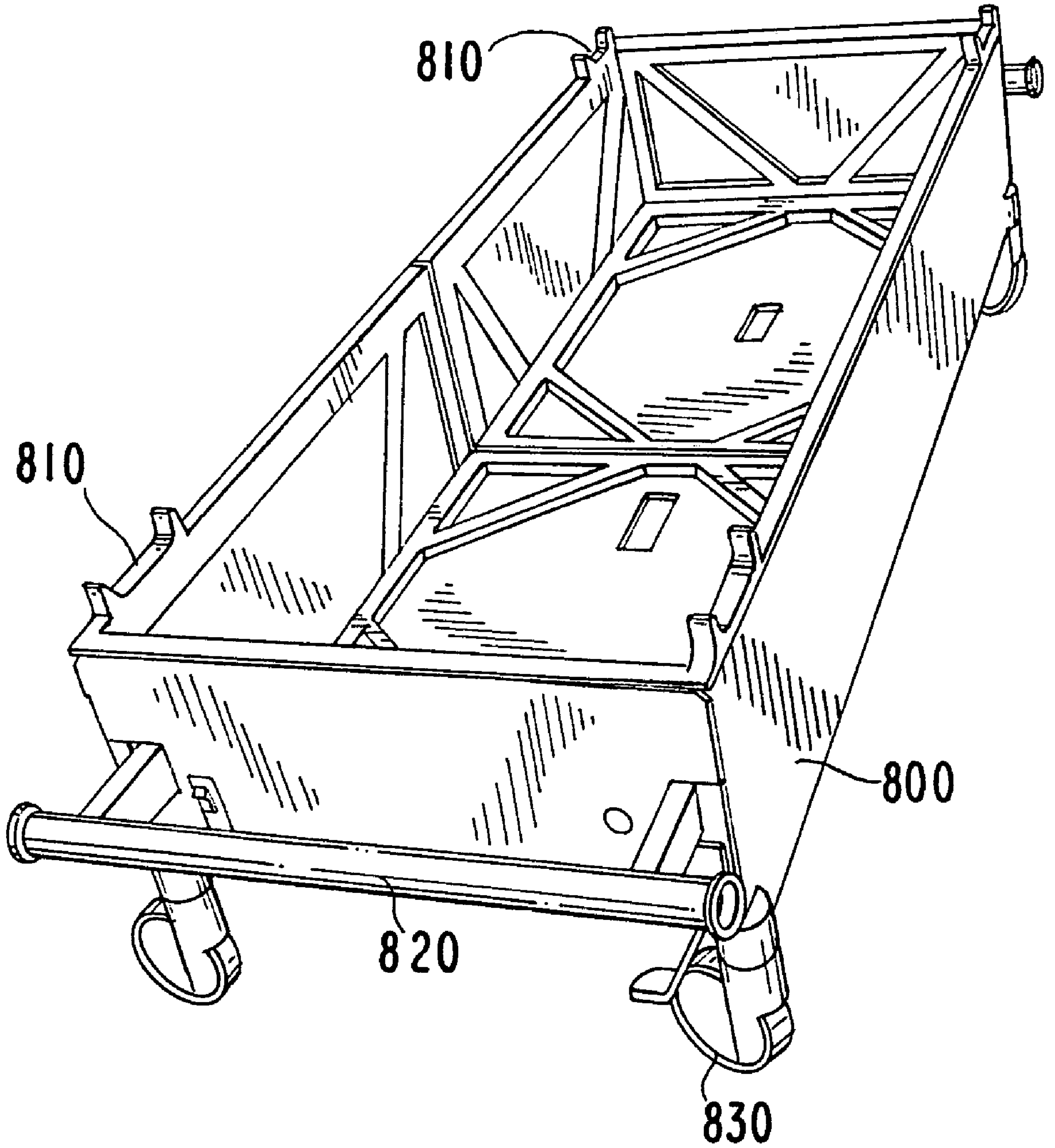
FIG. 14B shows a box frame without a drive, according to a preferred embodiment of the present invention.
Figure 15A:
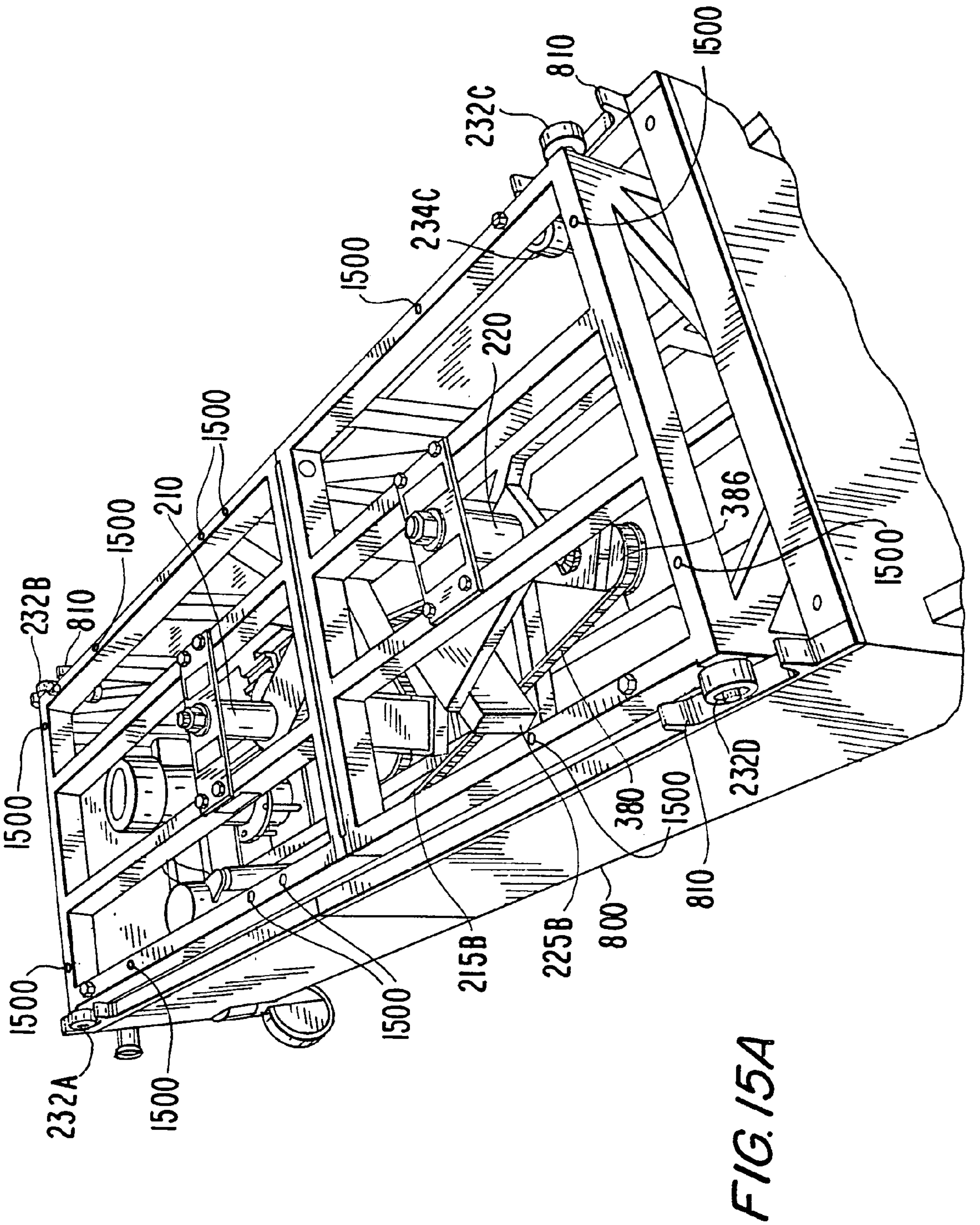
FIG. 15A shows a drive resting its track wheels on the tracks of a box frame according to a preferred embodiment of the present invention.
Figure 15B:
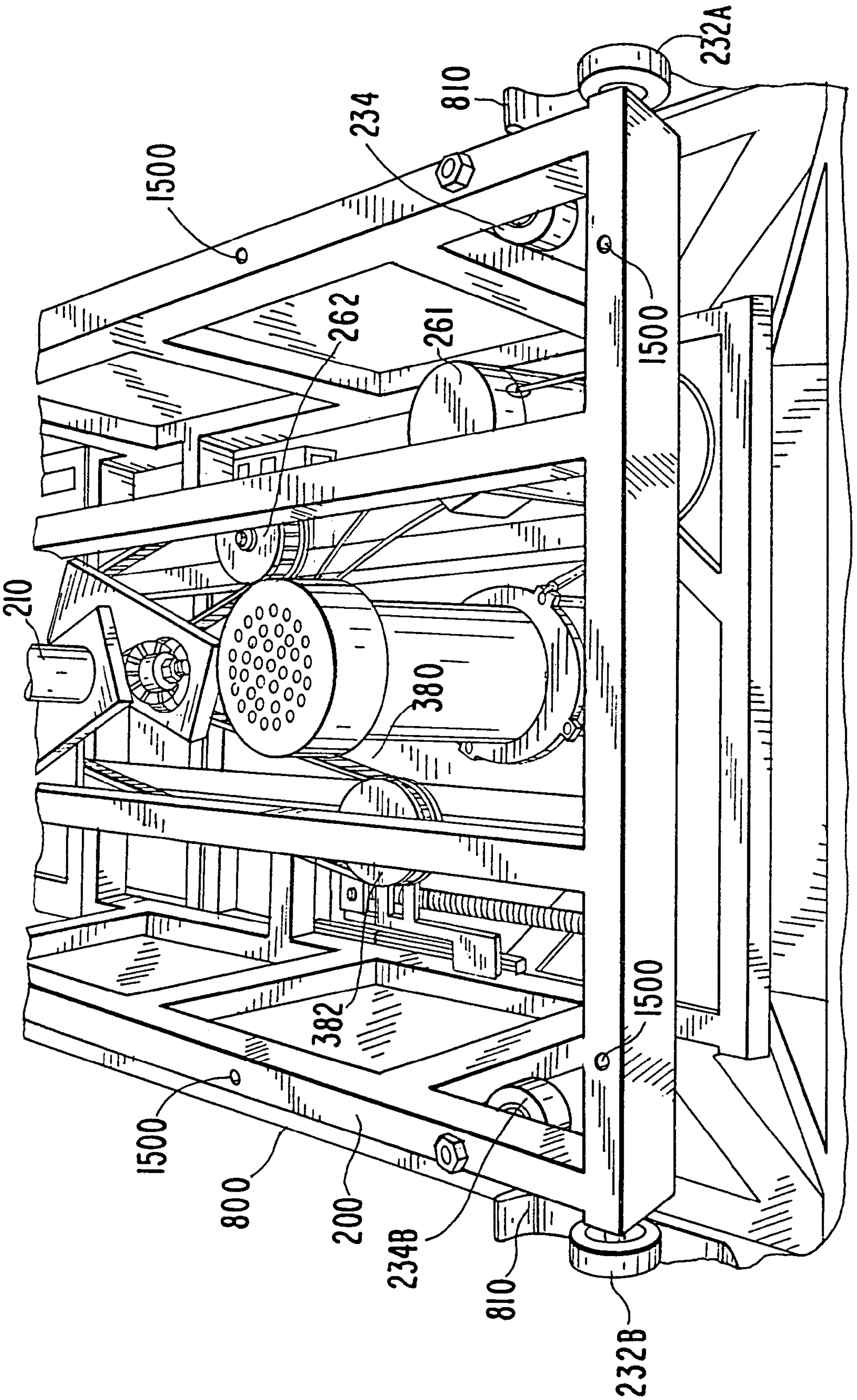
FIG. 15B is a closeup of one end of the box frame in FIG. 8B, according to a preferred embodiment of the present invention.
Figure 16:
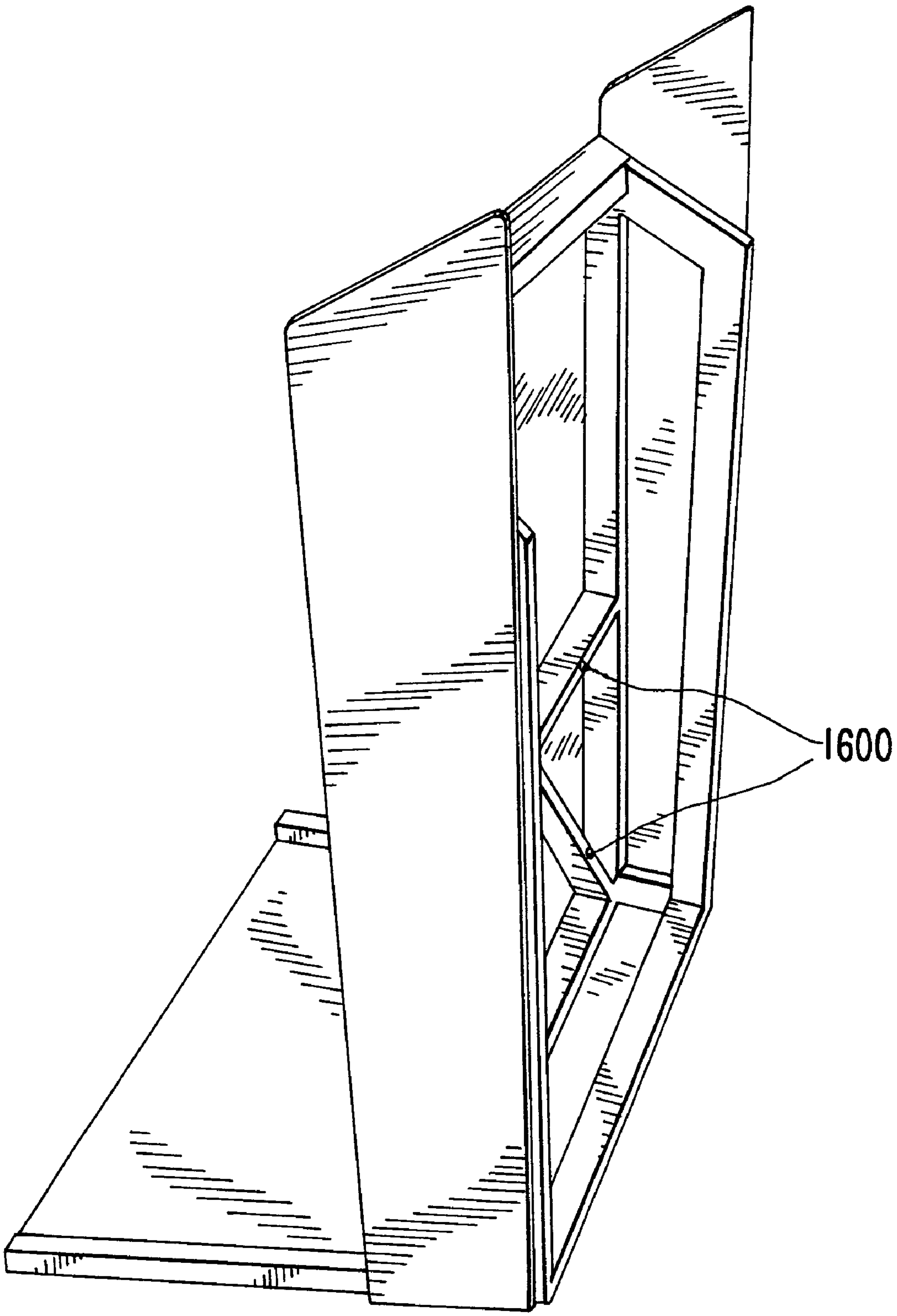
FIG. 16 shows the two halves of a disassembled mattress support according to a preferred embodiment of the present invention.

The following drawings are intended to clarify the spatial relationships of the various components. FIG. 14A shows the drive alone held aloft; FIG. 14B shows the box frame without the drive. FIG. 15A shows the drive resting by its wheels in the tracks of the box frame, while FIG. 15B is a closeup of one end of the box frame. In FIG. 15B. two of the horizontal wheels are shown. There are four low-friction horizontal wheels which run in contact with the inner side of the box frame in order to provide extra stability. Four holes can be seen on the top edges of the drive: two on the top edge at the bottom of FIG. 15B, and one on each of the top edges on either side of FIG. 15B. These are connection points where the mattress frame is attached to the drive. Similar points appear at the other end of the drive. FIG. 16 shows the two halves of a mattress support (one is halfway out of the left side of the drawing). In the center of FIG. 16 is the half of the mattress support with the footboard support attached (seen resting on the floor), whereas only the bottom side of the other half can be seen on the left side of the picture. Some of the connection points corresponding to the connection points in FIG. 15B can be seen in FIG. 16.

Figure 2:
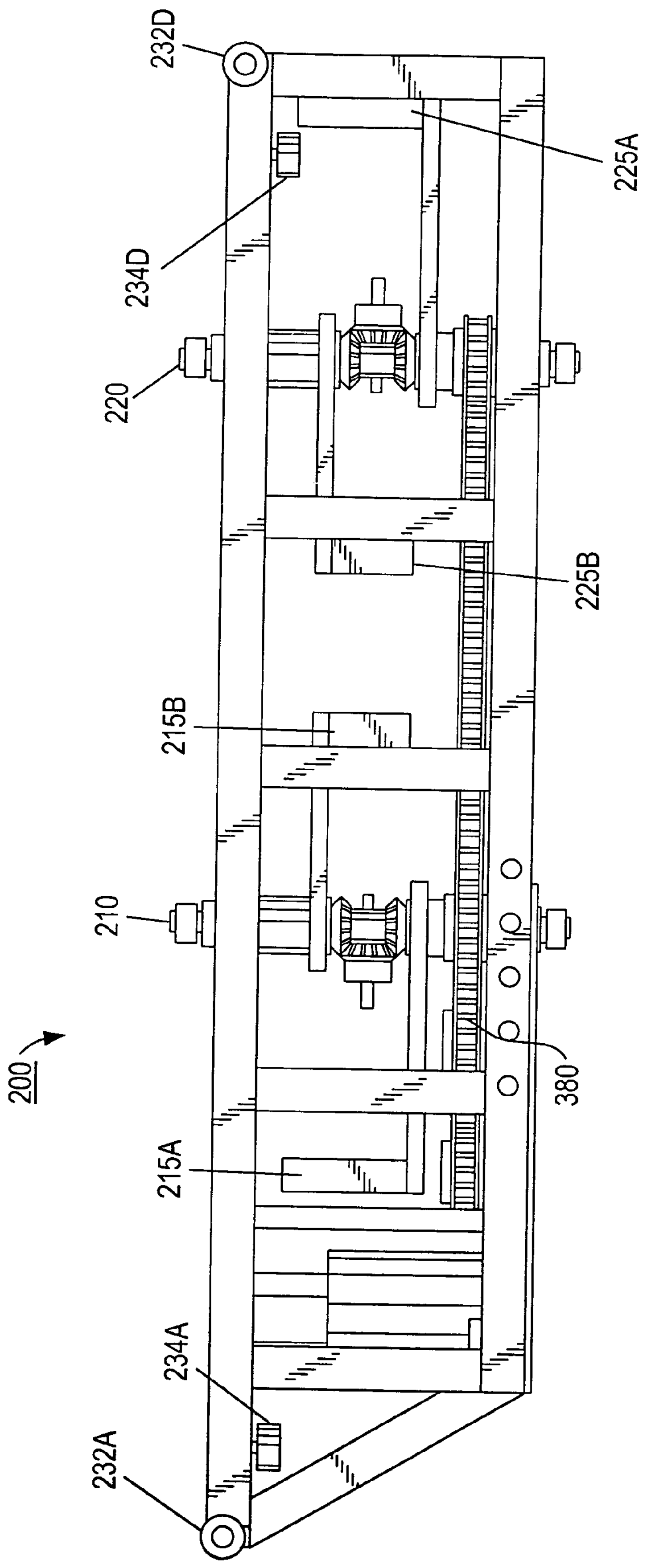
FIG. 2 is a schematic drawing of a side view of a drive according to a preferred embodiment of the present invention.
Figure 3A:
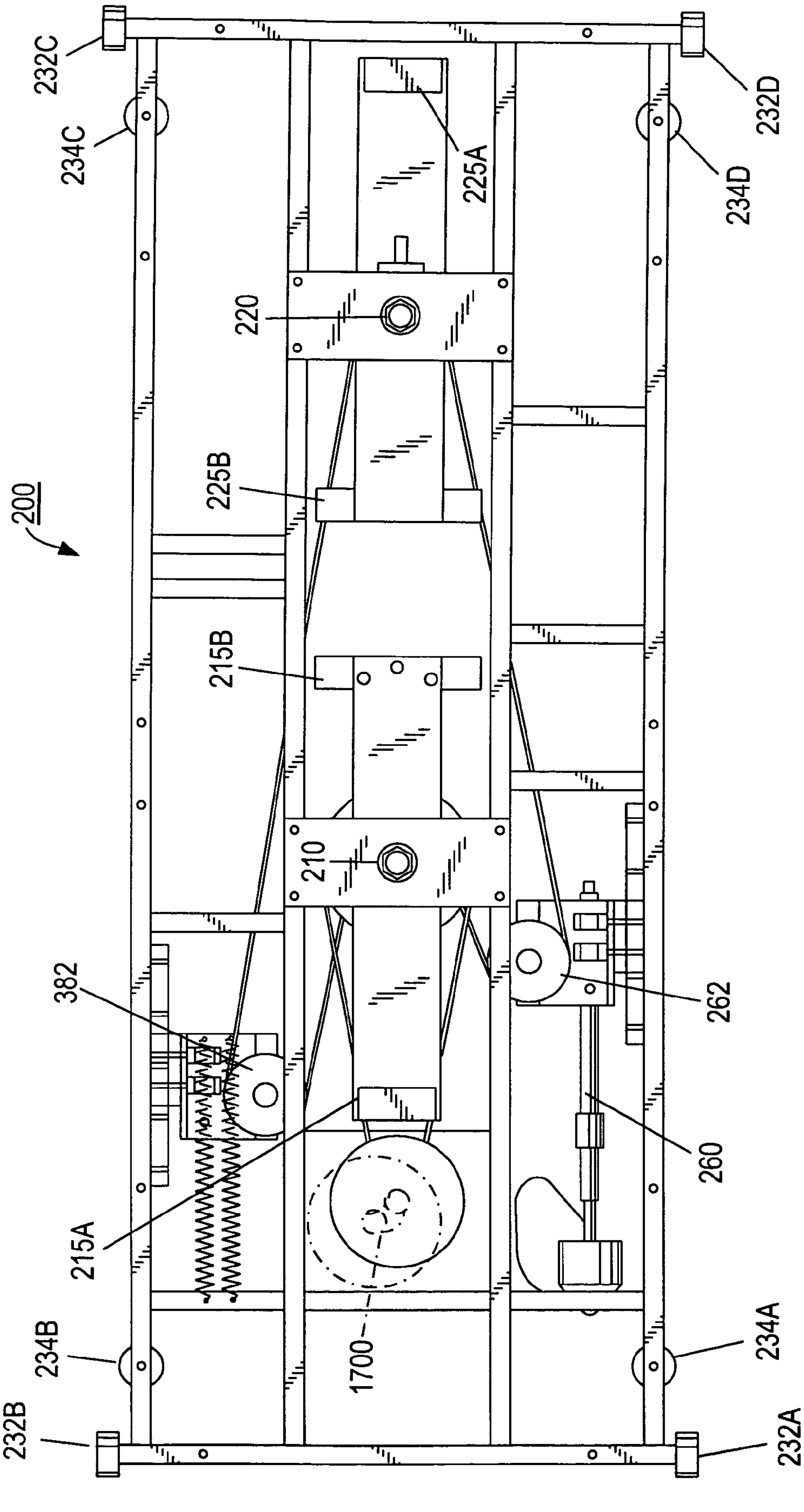
FIG. 3A is a schematic drawing of a top view of a drive according to a preferred embodiment of the present invention.

Now that the physical connections and orientations of the various components has been described, the mechanism in the drive will be described. According to the presently preferred embodiment of the present invention, the drive weighs 200 lbs and is 24" wide. The displacement modules in the drive take the form of two pairs of rotating counterweights, connecting belts, pulleys, springs, and motors. FIG. 2 is a side view and FIG. 3A is a top view of the drive and its various mechanisms. One end of the drive (shown on the left in FIG. 2) was built angled in so that the necessary electronics could fit in that corner of the box frame under the angled in end of the drive. However, the electronics do not take up that much room and there is no necessity to build one end of the drive angled in (at least not for the sake of electronics).

Figure 17:
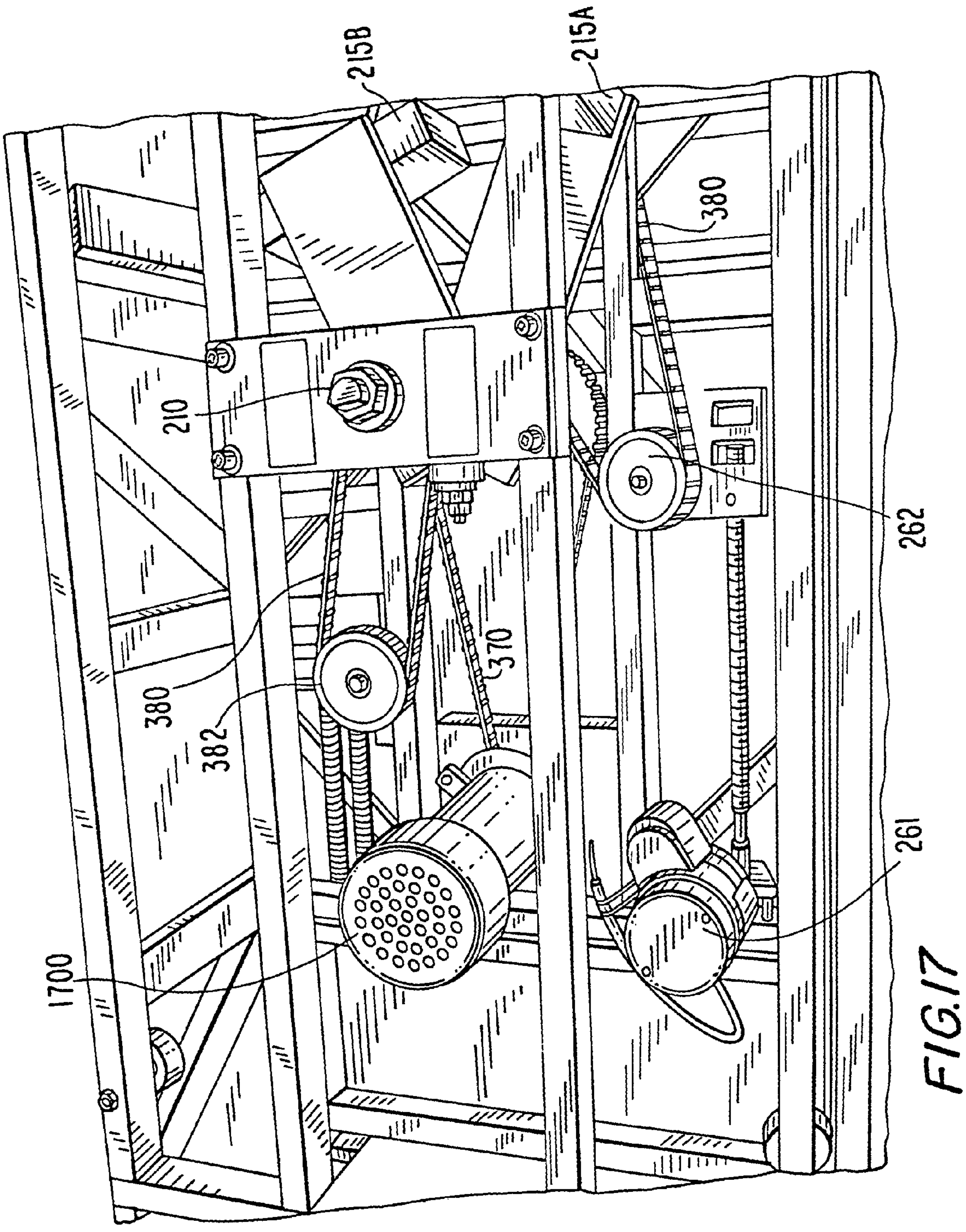
FIG. 17 is a closeup of the top part of a drive inside of a box frame according to a preferred embodiment of the present invention.

In FIGS. 2 and 3A, the two pairs of drive weights 215A & 215B and 225A & 225B are shown attached to their respective horizontal shafts 210 and 220. The side of track wheels 232A and 232D can be seen in FIG. 2 and the side of horizontal wheels 234A–D can be seen in FIG. 3A. There are two motors, the drive rotation motor 1700 (which rotates rotation shaft 350) which drives the drive weights and a linear displacement motor 261 (which moves pulley wheel 262 up and down linear shaft 260) which sets the phase difference between the two pairs of drive weights (this will be explained further below). FIG. 17 is a drawing taken from a picture of the top part of the drive 200 in the box frame 800. Some of the parts in FIGS. 2 and 3A can be seen in FIG. 17: the drive rotation motor 1700, the linear displacement motor 261, the movable pulley wheel 262 controlled by the linear displacement motor 261, and the drive shaft 210.

As might be apparent from FIG. 17, the positions of the drive weights in FIGS. 2 and 3A are inaccurate, in the sense that the drive weights would never be in the positions shown. The correct movement of counterweights 215A and 215B as seen from above is shown in FIGS. 4A–E. In FIG. 4A, the centers of gravity of both drive weights 215A and 215B are on the same line 401 from center drive shaft 210. As center drive shaft 210 continues to rotate in FIG. 4B, drive weights 215A and 215B continue their rotations in opposite directions: drive weight 215A in a clockwise direction, drive weight 215B in a counterclockwise direction. In FIG. 4C, the drive weights have moved into positions opposite each other. This is beneficial because the force of the two drive weights are also in opposite directions and thus, negate each other's effect. The rotation continues in FIG. 4D and then the drive weights end up adding the force of their weights in the same direction in FIG. 4E. FIGS. 4A–E show how the motion of the drive weights moves the drive 200 up and down the box frame tracks (i.e., headwards and footwards for a subject on the mattress 101), but not sideways within the box frame 800. If FIG. 4A is the position which causes the headward movement, FIG. 4C is the position which negates any movement, and FIG. 4E causes the footward movement.

Figure 18:
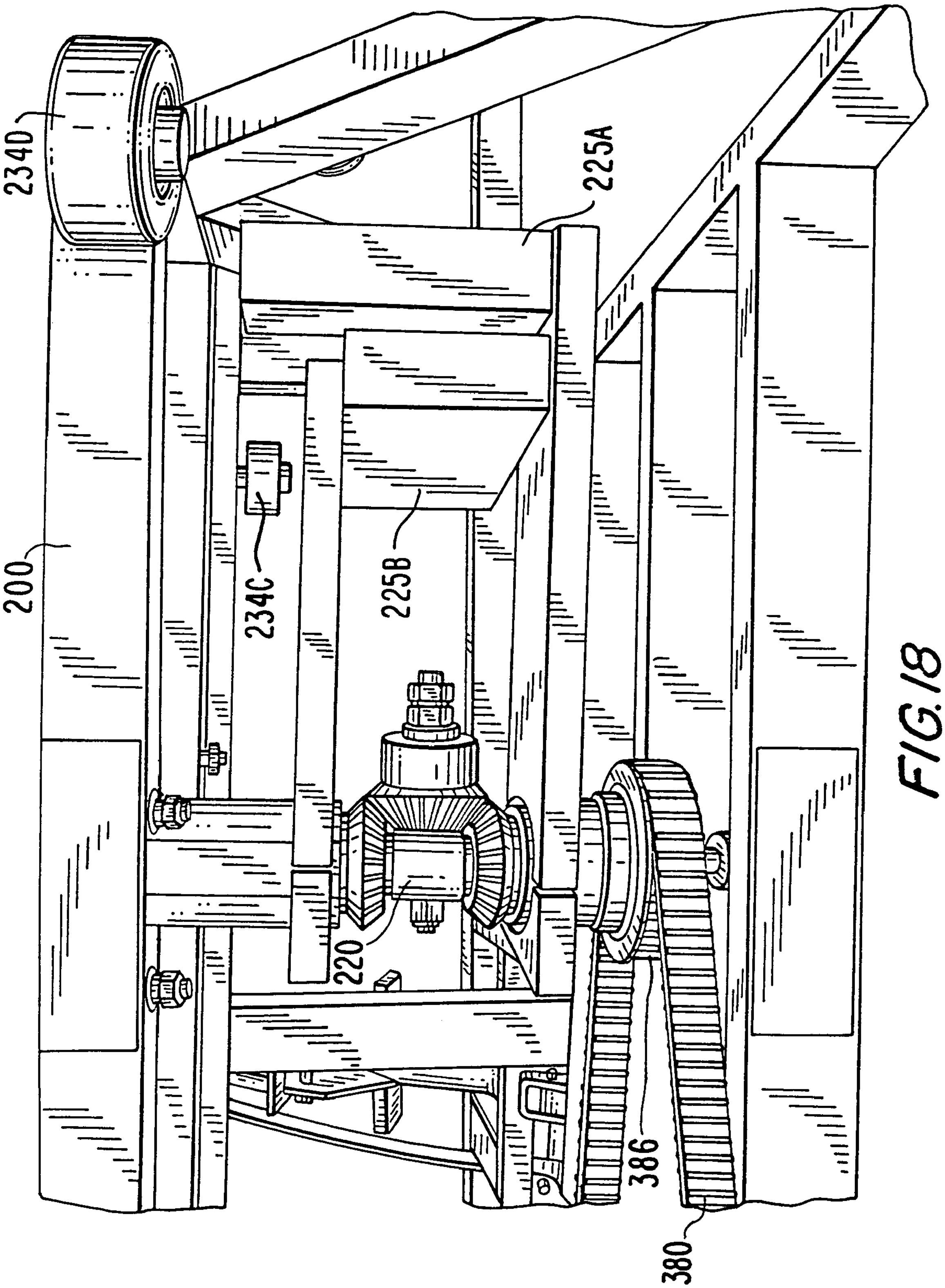
FIG. 18 is a closeup of a shaft and its drive weights in a drive according to a preferred embodiment of the present invention.

As can be seen in FIGS. 2 and 3A, the drive weights are of unequal size. This is because the weights are located at different distances from the center of drive shaft 210. If the drive weights were the same mass, their effects would not be balanced and the drive 200 would rock sideways in the box frame 800. However, if drive weight 215B is a predetermined amount of mass less than drive weight 215A, the effect of the drive weights when rotating in opposite directions will cancel each other out. Because of this arrangement, the drive weights are in the same horizontal plane as shown in FIG. 2, which greatly reduces any shimmy effect that was produced in previous platform versions which had their drive weights in different horizontal planes. The outer edge of drive weight 215A is 12" from drive shaft 210 and this outer edge travels past the very outside edge of the drive itself when rotating. FIG. 18 is a side view of shaft 220 with drive weights 225A and 225B. The drive belt 380 connecting drive shaft 220 (at pulley wheel 386) to drive shaft 210 (at pulley wheel 384) and pulley wheel 262 through the pulley system can be seen at the bottom of shaft 220.

Figure 3B:
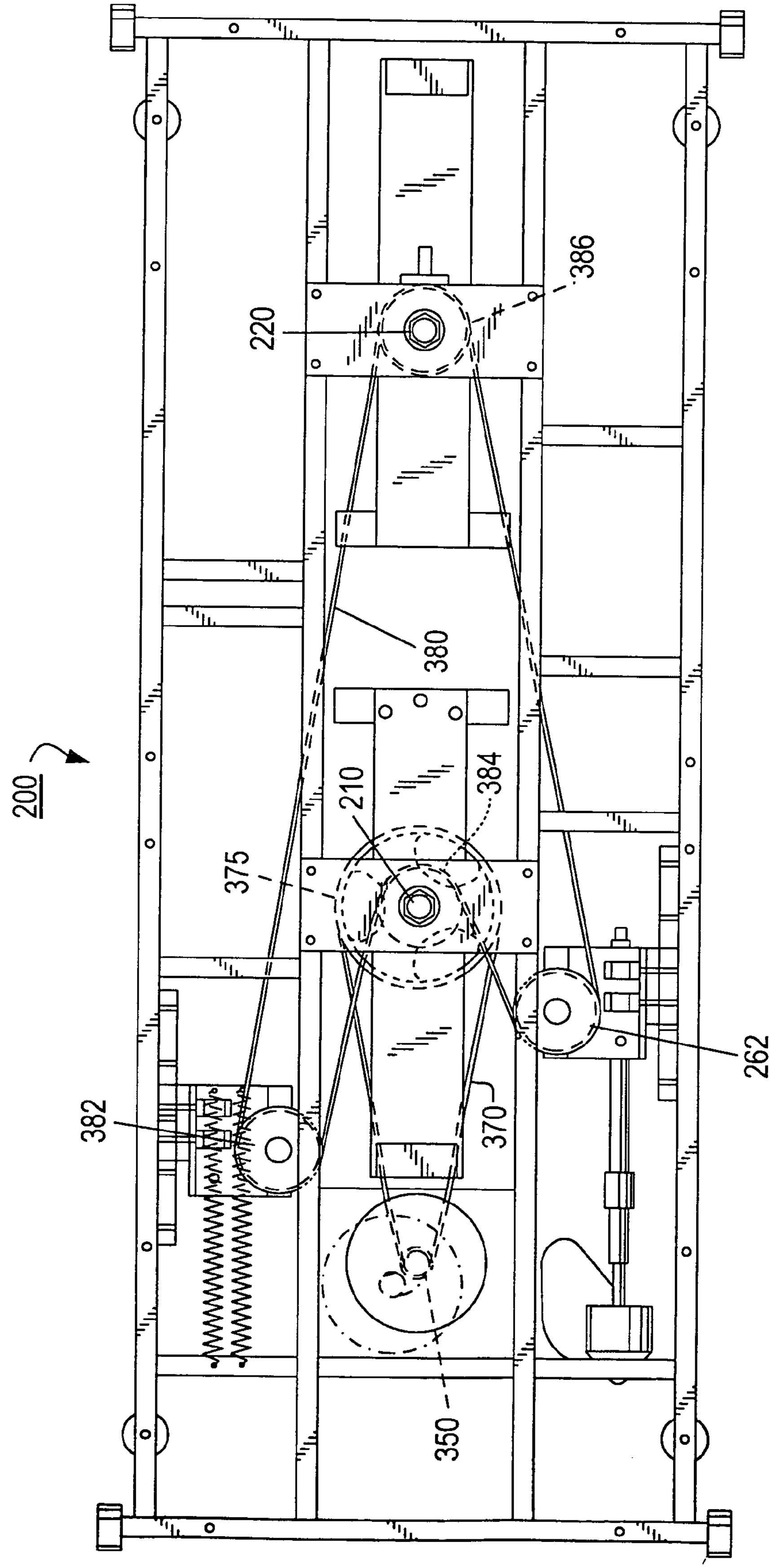
FIG. 3B is a schematic drawing of the top view of FIG. 3A, but with the drive belt and phase control belt highlighted, according to a preferred embodiment of the present invention.

FIG. 3B is a top view of the drive, identical in shape to FIG. 3A. However, FIG. 3B shows the pulley system with drive belt 370 and the phase control belt 380. In the presently preferred embodiment, drive belt 370 runs from rotation shaft 350 to drive shaft 210 and provides the power to rotate drive weights 215A and 215B around drive shaft 210 and indirectly provides the power to rotate drive weights 225A and 225B around shaft 220. Drive belt 370 in the presently preferred embodiment is a ¾" L pitch timing belt, although a timing belt is not required in this position. Because of the size of the wheel 375 around drive shaft 210 which is driven by drive belt 370 in comparison to the size of rotation shaft 350, there is a 5:1 speed reduction from the drive rotation motor to the actual rotational speed of the drive weights. In the presently preferred embodiment, the drive rotation motor is a 180 VDC ½ hp 0–1750 RPM motor, although only ⅒ hp is actually used (which means a smaller motor may be safely used).

Phase control belt 380 runs around four pulley wheels of equal size: release pulley wheel 382, drive shaft pulley wheel 384, secondary shaft pulley wheel 386, and linear displacement pulley wheel 262. Because it is also attached to drive shaft 210, drive pulley wheel 384 drives the phase control belt. Secondary shaft pulley wheel 386 receives the power to rotate the drive weights around shaft 220 from drive shaft pulley wheel 384 through phase control belt 380. Release pulley wheel 382 provides required tension for phase control belt 380, and can also be used to release the tension on phase control belt 380 in order that phase control belt 380 can be taken off for repair or transport. Linear displacement pulley wheel 262 can be moved in position up and down linear shaft 260 under the control of linear displacement motor 261. It is by this means that the relative phases of the two pairs of drive weights are controlled.

The drive weights around each shaft make the same movements as shown in FIGS. 4A–4E. However, one pair of drive weights can be moved in and out of phase with the other pair of drive weights. The two pairs of drive weights are in phase when they are in the same rotational positions at the same time. Both pairs would look like FIG. 4A at the same time, like FIG. 4B at the same time, etc. The two pairs are out of phase when they are not in the same rotational positions at the same time. For instance, drive weights 215A & 215B might be in the position shown in FIG. 4A, while drive weights 225A & 225B might be in the positions shown in FIG. 4B. In that case, they would be 45° out of phase with each other. Although the sideways forces of these out-of-phase pairs of drive weights would still cancel themselves out (and thus not produce a rocking effect in the movement platform), the force produced in the headwards-footwards directions would lessen in comparison to when the pairs of drive weights are in phase.

The linear displacement motor 261 is a 9" per minute 400 lb. 110 VAC linear displacer with 12" of travel, which is much more than necessary. A smaller, cheaper, and less powerful linear displacer may be used instead. Phase control belt 380 is a 1" H pitch timing belt, approximately 110" long. It is important for this belt to be a timing belt in order to prevent the drive weights from coming out of adjustment. The reversing gears currently used are Boston L130Y or equivalent miter gears. It is contemplated that the miter gears may be replaced with unequal sized bevel gears. Any means of varying the phase may be used, including manually, rather than using a linear displacement motor.

The relative phases of the pairs of drive weights are controlled by moving linear displacement pulley wheel 262 on linear shaft 262. The speed of rotation of the pairs of drive weights are controlled by increasing or decreasing the speed of the drive rotation motor 1700. Thus, one can control both the speed of the headwards-footwards movement (by increasing or decreasing the speed of the drive rotation motor 1700) and the force applied by the headwards-footwards movement (by moving the pairs of drive weights in and out of phase with each other through linear displacement pulley wheel under the control of linear displacement motor 261). In its simplest form, the control electronics of the present invention merely control these two variables in order to get the desired effect on the subject (as described, for example, in the '962 patent and the '422 application). A handheld controller with a communication link to the control electronics of the drive 200 may be used by the health care provider or the subject him- or herself. Readings of the speed and peak acceleration could also be available. The control electronics also incorporate a "patient stop switch" which may be given to the subject to hold. The motors would stop whenever the switch was activated.

Figure 5:
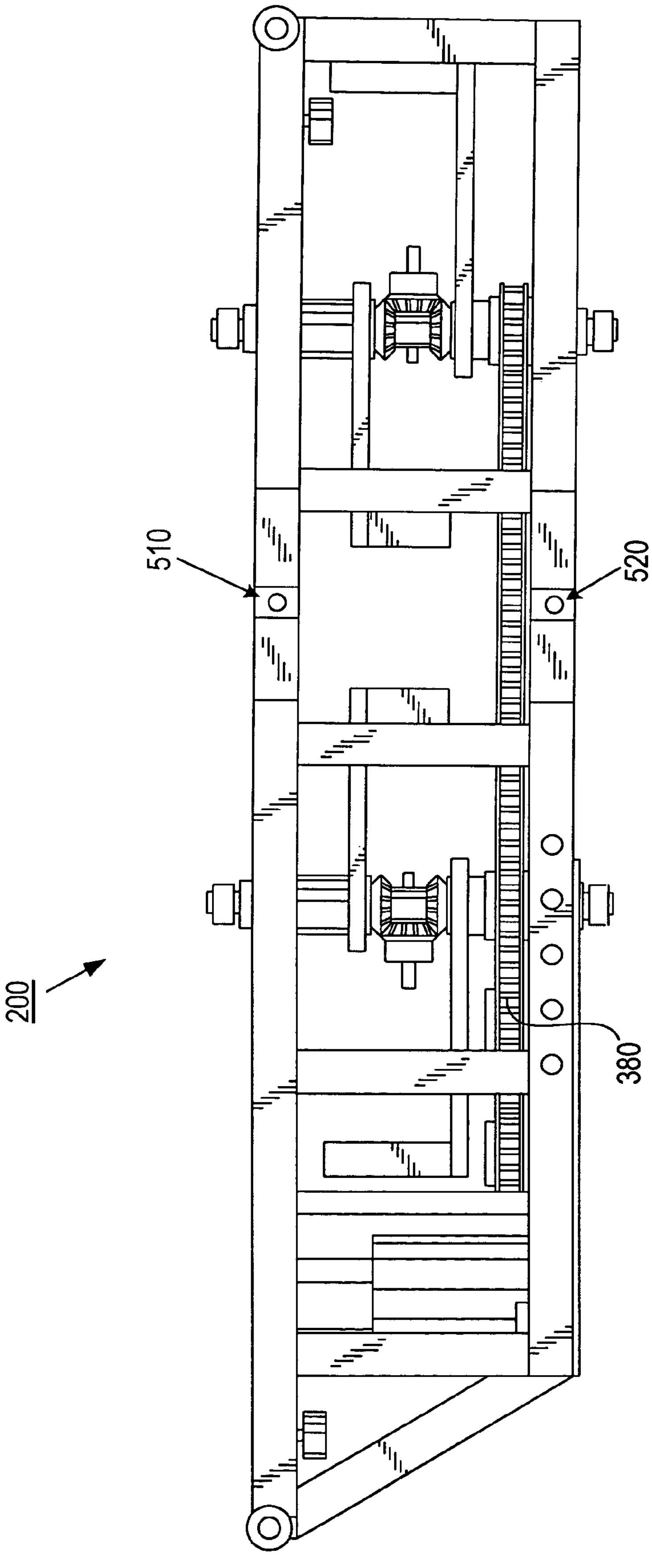
FIG. 5 is a schematic drawing of a side view of a two-piece drive according to a preferred embodiment of the present invention.
Figure 6:
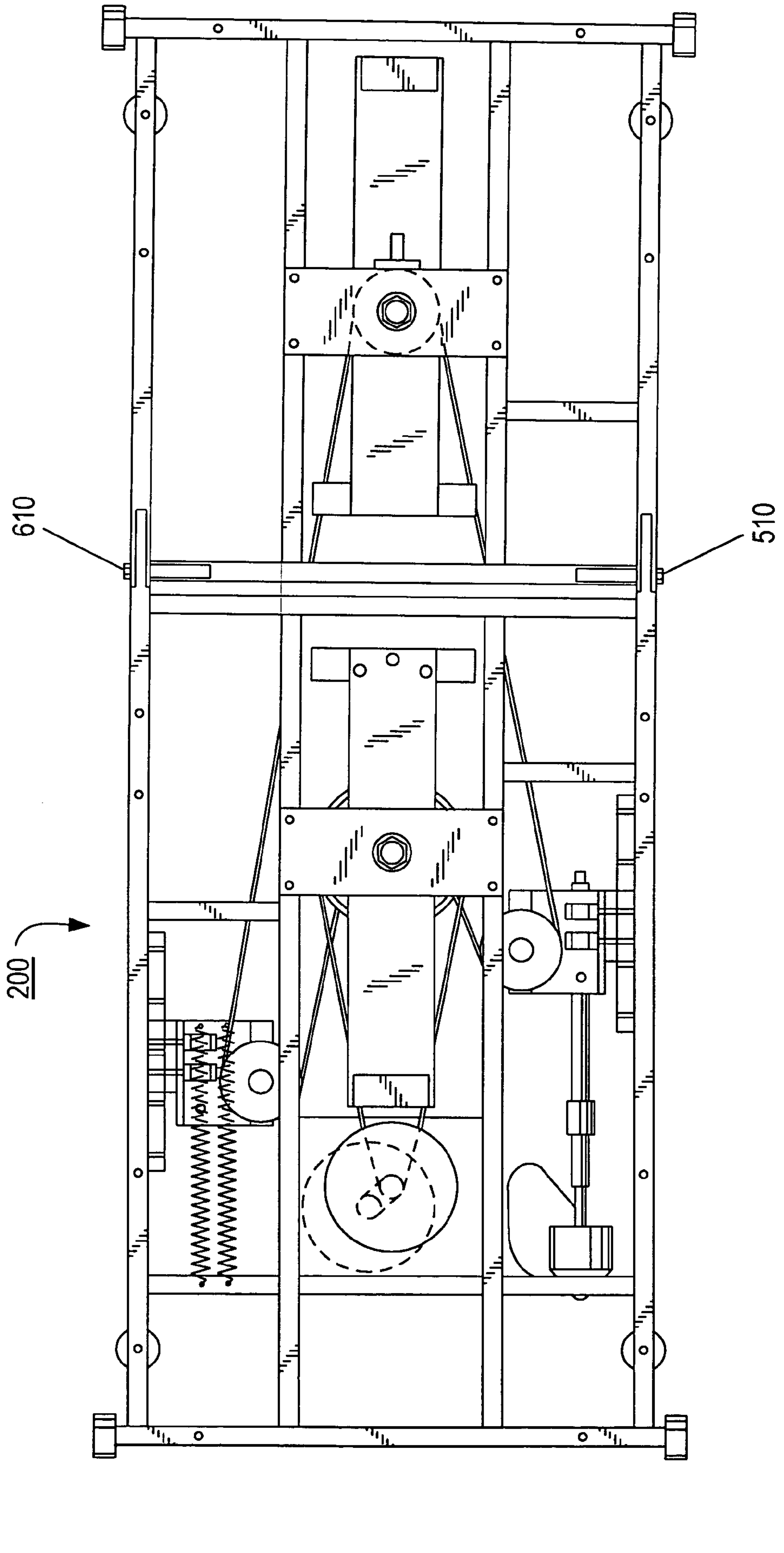
FIG. 6 is a schematic drawing of a top view of a two-piece drive according to a preferred embodiment of the present invention.
Figure 19A:
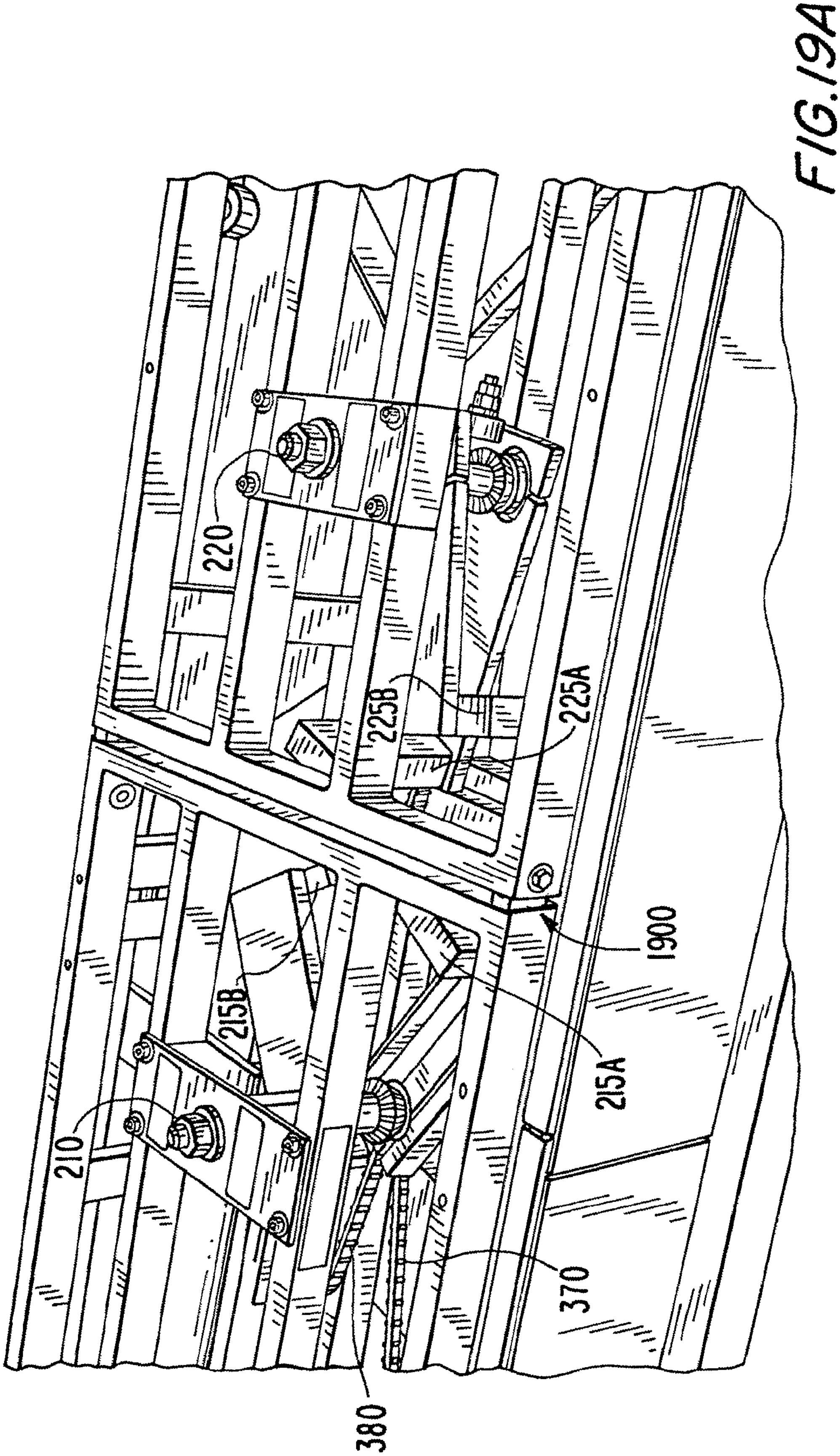
FIGS. 19A and 19B show two different views of the connection points on the top of a two-piece drive according to a preferred embodiment of the present invention.
Figure 19B:
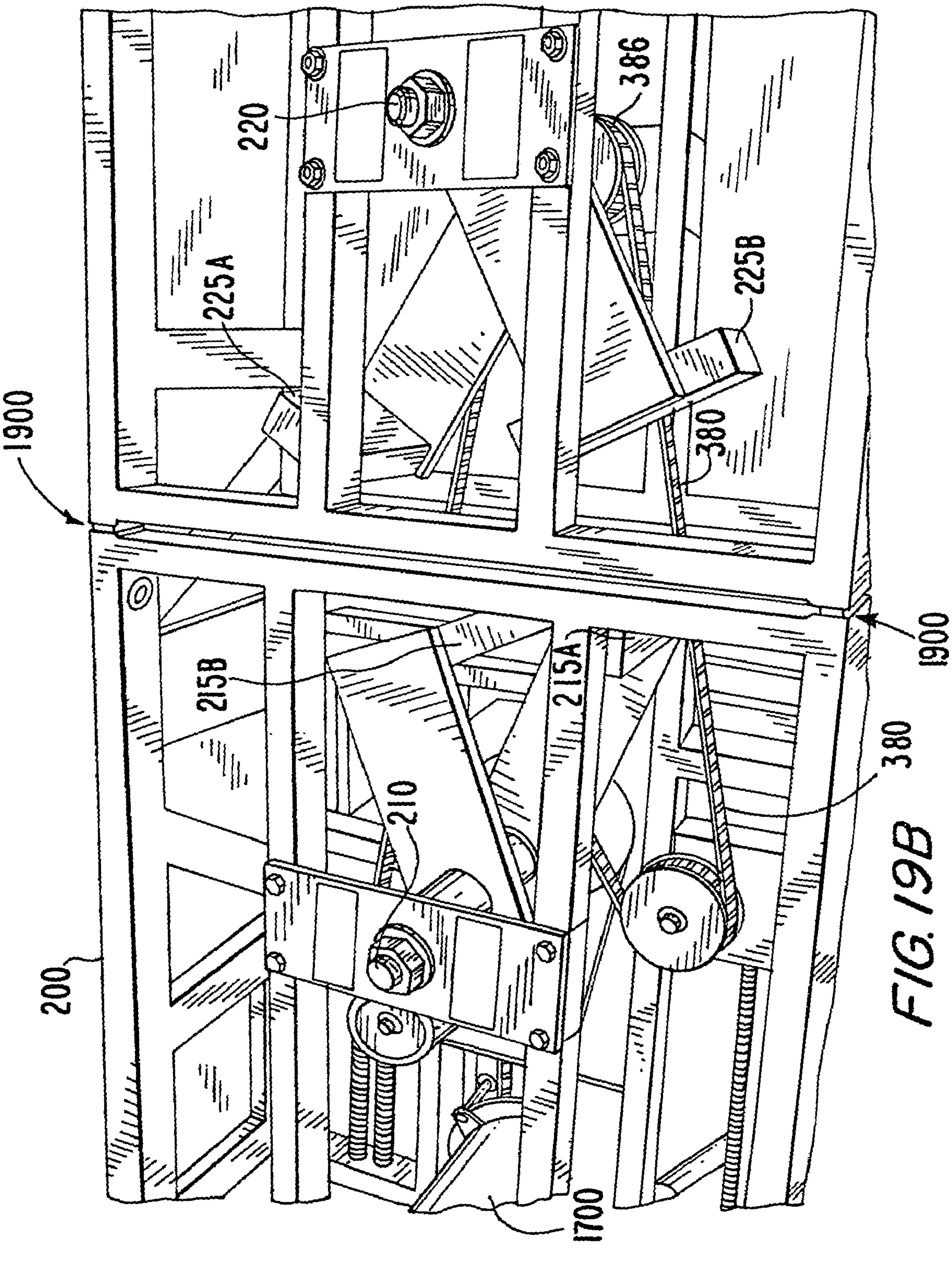

Although FIGS. 2, 3A and 3B show a one-piece embodiment of the present invention, a two piece embodiment is also possible (as has been described above in regards to the box frame and mattress support in FIGS. 12 and 16). The drive and box frame may be partially assembled into two complete halves, and then those halves are put together at the final destination place of the reciprocating movement platform. FIGS. 5 and 6 are a side view and a top view, respectively, of a two-piece embodiment of a drive according to the present invention. The points where the two halves were joined together are shown at 510, 520, and 610. The same bolts are used almost everywhere in the construction of the two-piece embodiment: 3½" long ⅜" bolts. 3⁄16" bolts could be used with the ⅜" bolts or instead of the ⅜" bolts. This uniformity makes assembly and inventory much easier. FIGS. 19A and 19B are two different top views of the connection points on the top side of the drive in a two-piece embodiment.

Figure 7:
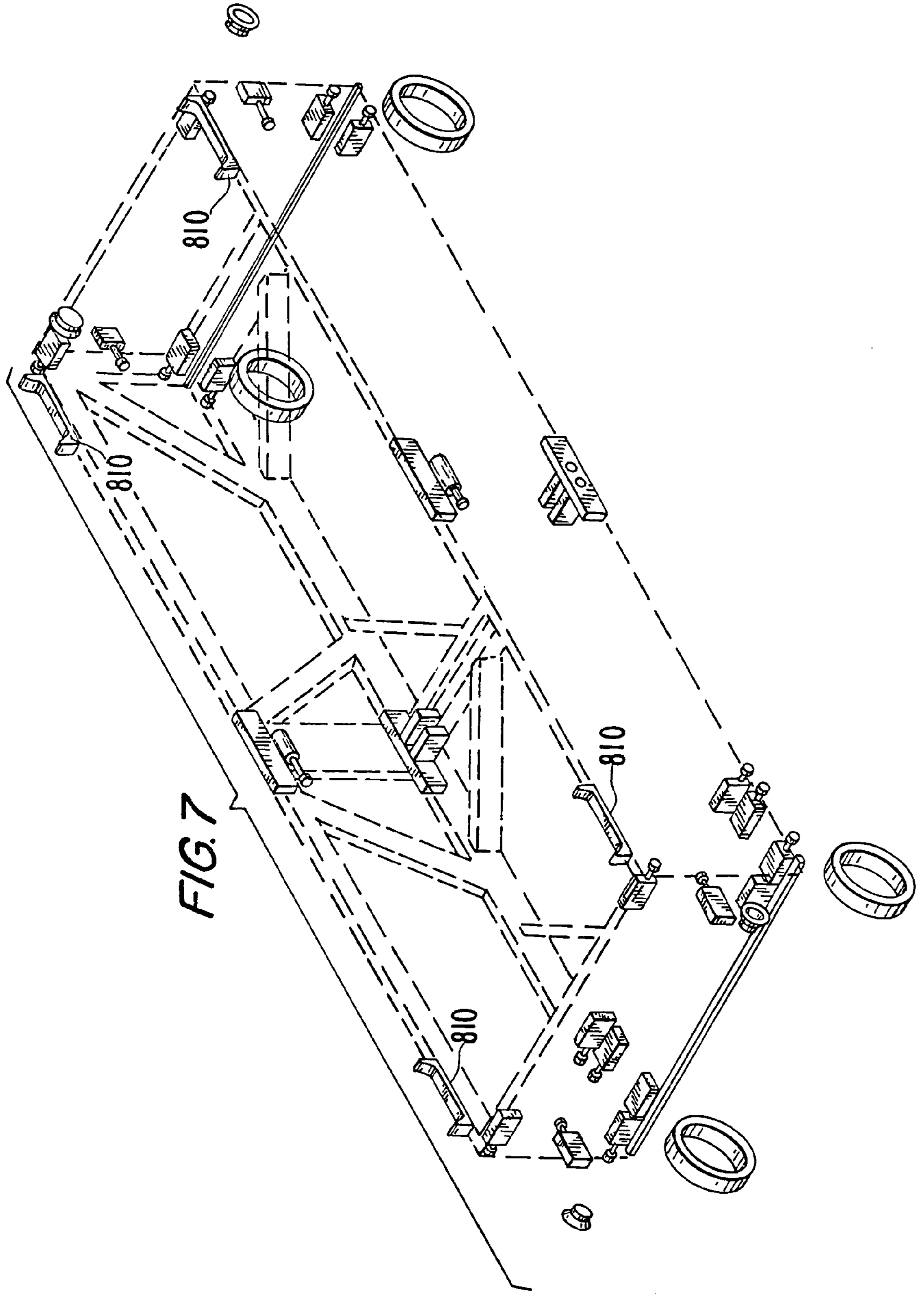
FIG. 7 is a schematic drawing of a side view of a two-piece box frame according to a preferred embodiment of the present invention.
Figure 8:
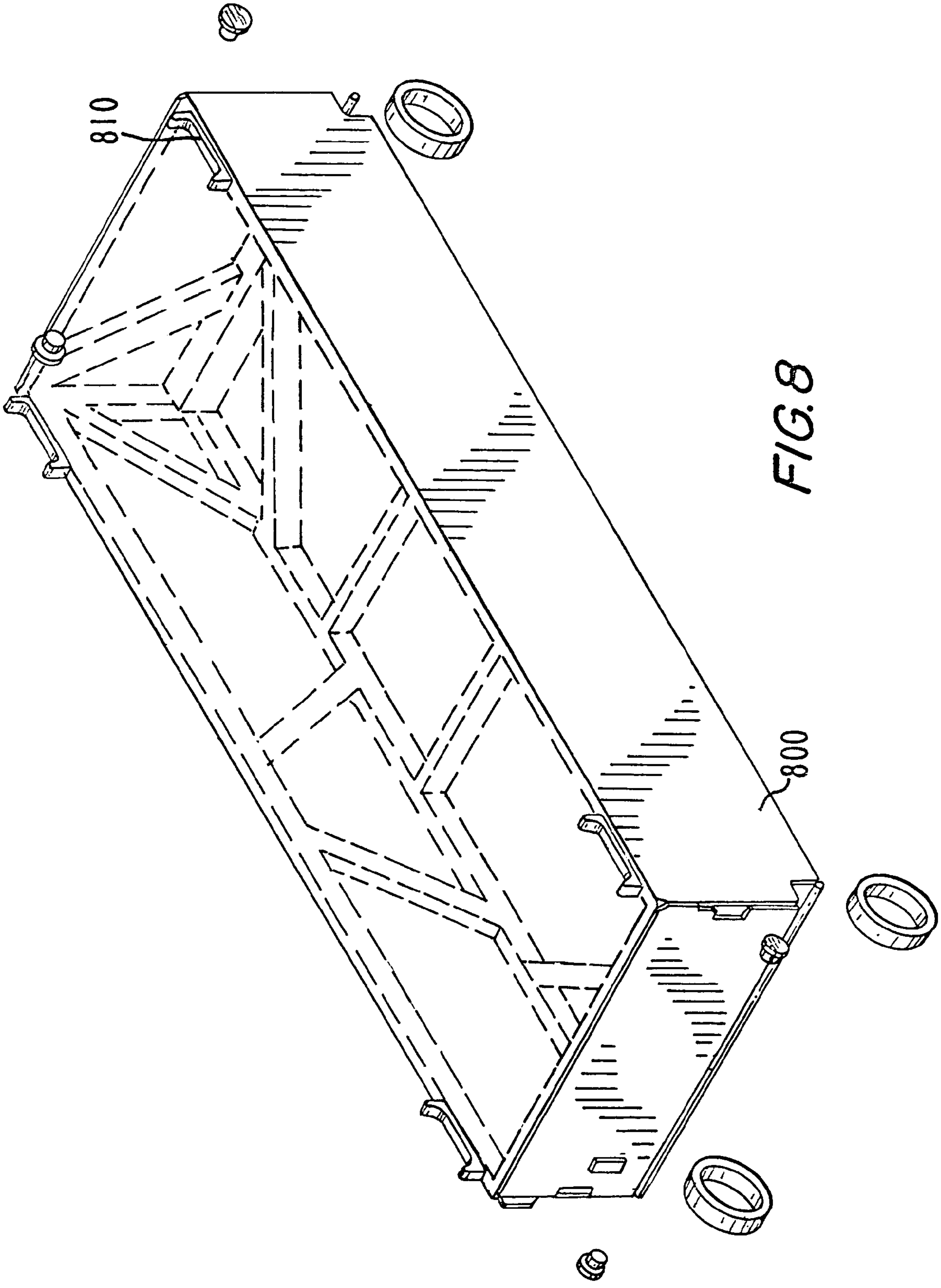
FIG. 8 is a schematic drawing of a side view of a one-piece box frame according to a preferred embodiment of the present invention.
Figure 9A:
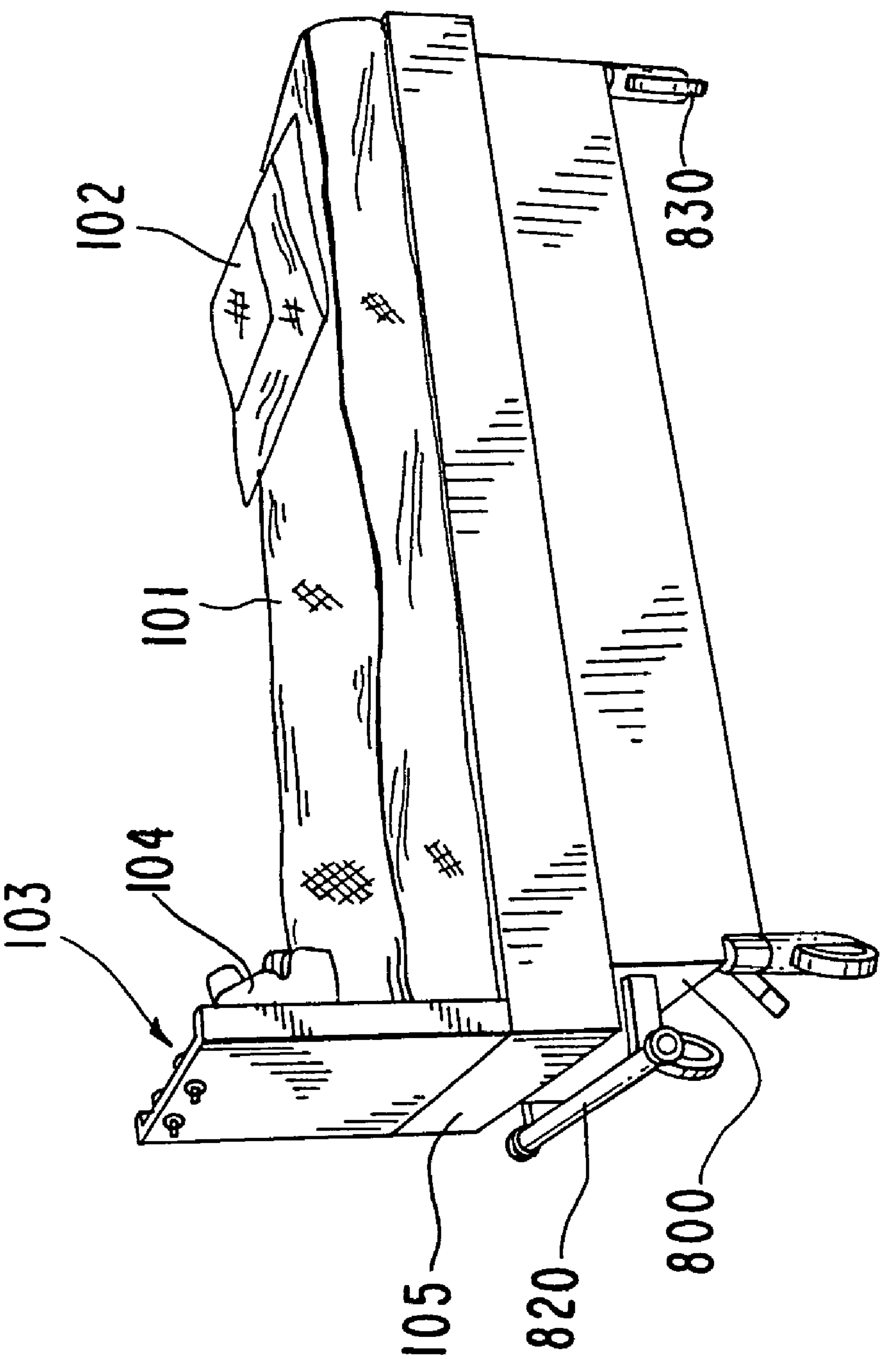
FIGS. 9A, 9B, and 9C are different views of a completely assembled reciprocating movement platform according to a preferred embodiment of the present invention.
Figure 9B:
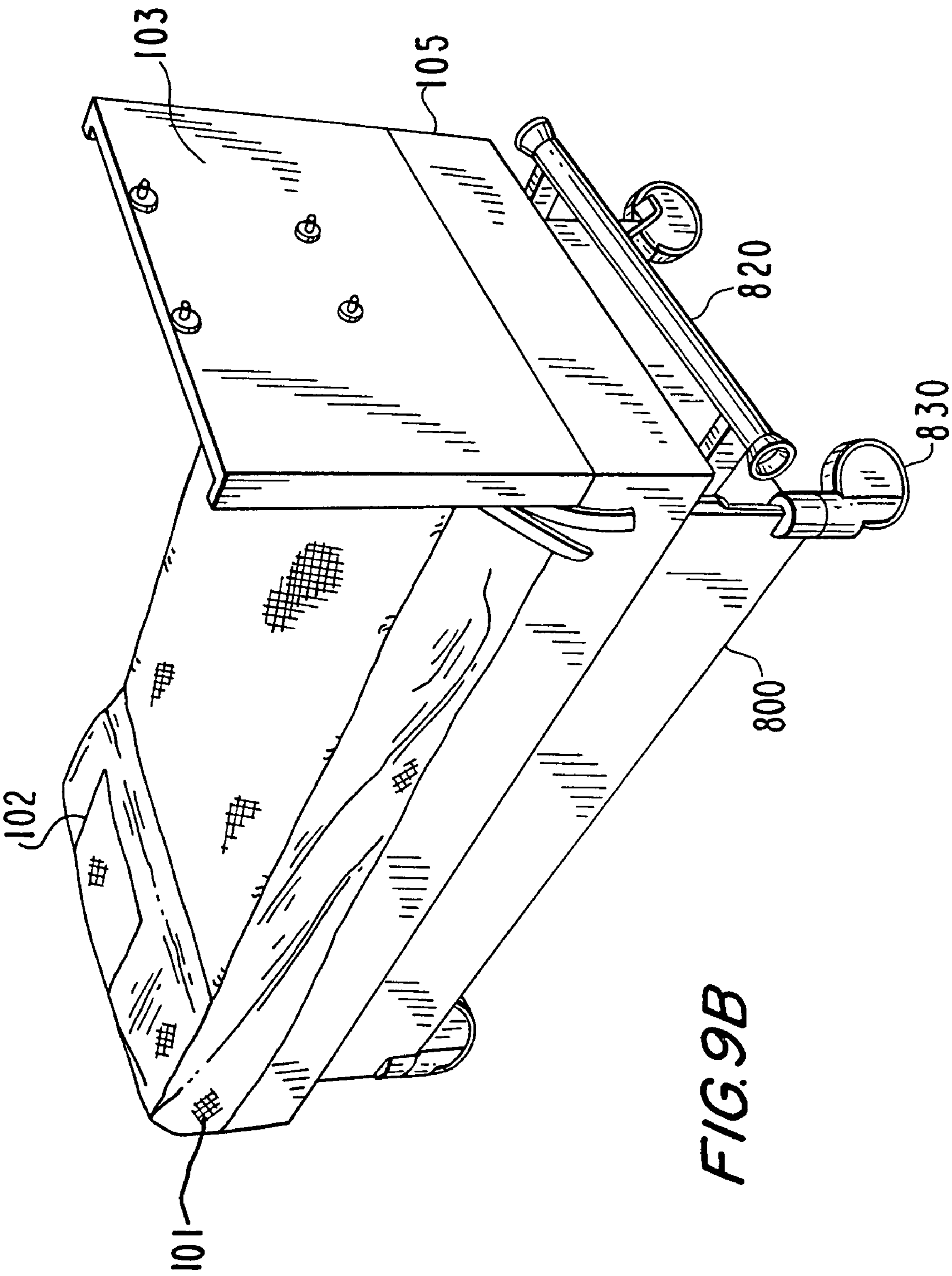
Figure 9C:
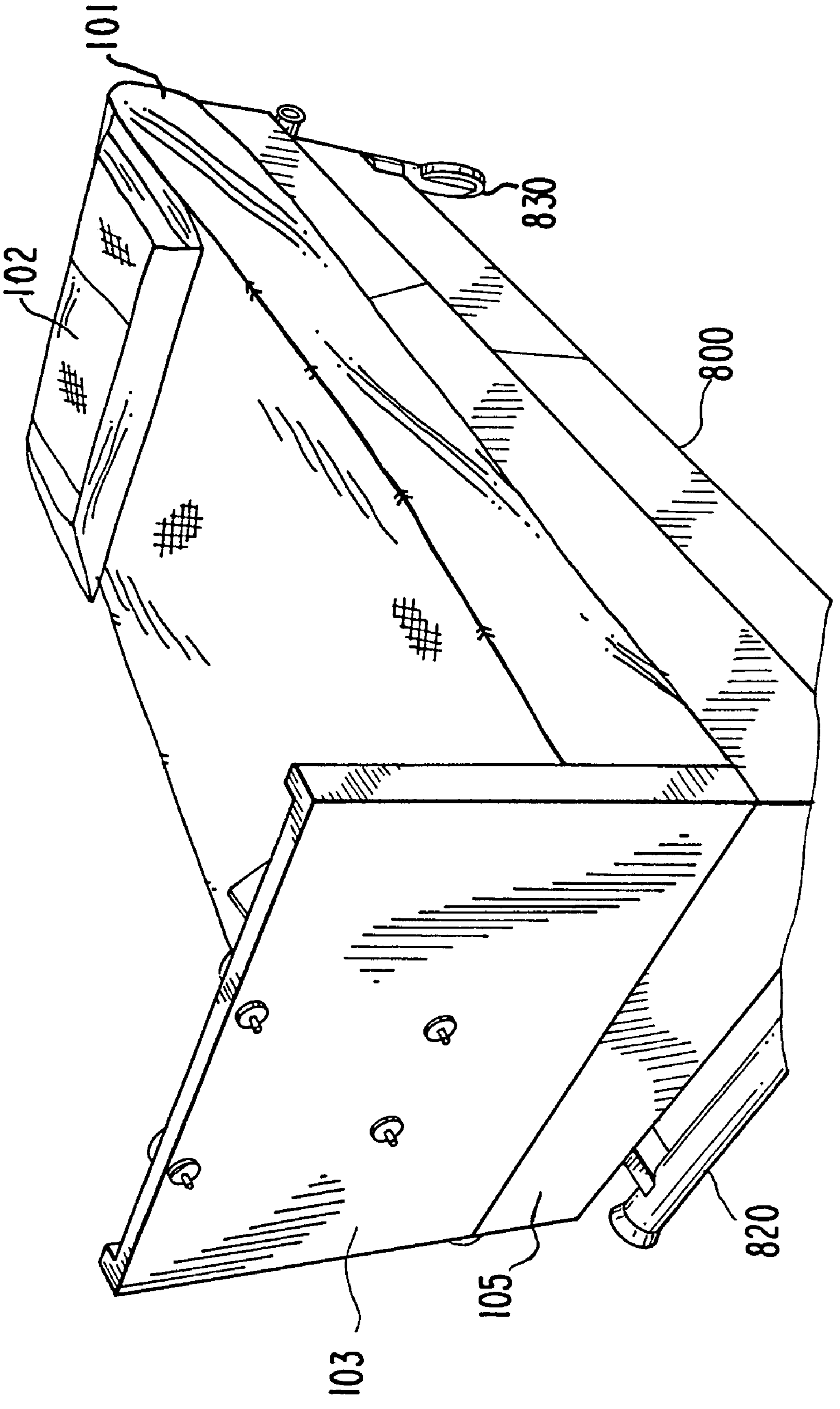

A drawing of a two-piece embodiment of the box frame according to the present invention is shown in FIG. 7. A corresponding drawing of a one-piece embodiment of the box frame according to the present invention is shown in FIG. 8.

Some, but not all, of the innovations and improvements introduced by the present invention include: a secure fastening of the subject to the reciprocating platform, a design for simple and easy assembly, an improved mechanism for creating and controlling reciprocating movement, an improved design for support of the moving portion of the platform, and an improved design for simplified and easier transport.

II. Methods of Treatment

This section will describe preferred embodiments of medical treatments using a reciprocating movement platform. Although use of the preferred embodiment of the reciprocating movement platform is preferred and the descriptions below are based on its use, another type of device which could apply pulses in the manner appropriate for the particular treatment (as discussed below) may be used.

In addition to the treatments previously disclosed in the '976 patent and the '422 application, embodiments of the reciprocating movement platform according to the present invention may be used to A) treat inflammatory diseases, B) serve as a means of preconditioning or conditioning vital organs to protect them from the deleterious effects of ischemia, C) function as a non-invasive ventilator and cardiopulmonary resuscitative device in human adults, children and babies, D) treat and precondition the organs of animals such as horses, and E) treat diseases or conditions where oxidative stress plays a role.

A. Treatment of Inflammatory Diseases

Immunologic Basis for treatment of Inflammatory Diseases with Pulses added to the Circulation and Fluid Channels of the Body Stress injures tissues thereby provoking an inflammatory response by the body's cells. Stress is caused by infection, trauma, behavioral, psychological, obesity, hormonal, environmental temperature & humidity, air quality, genetic, sleep disturbance, physical inactivity, strenuous exercise, aging, smoking, and air pollution among others. In most instances, the cause of stress is unknown and termed idiopathic. The inflammatory response initiated by stress involves elaboration of nuclear factor kappa beta, a transcriptional gene that is ubiquitously present in the body's cells. Nuclear factor kappa beta activates white blood cells and others to produce inflammatory cytokines, tumor necrosis factor alpha, metalloproteinases, adhesion molecules, and nitrogen & oxygen free radicals as well as liberating the vasoconstrictor molecule, endothelin-1 (Conner E. M., Grisham M. B. *Inflammation, free radicals, and antioxidants,* Nutrition, 12:274–77 (1996); Li X, Stark G. R. *NF kappa B-dependent signaling pathways,* Exp. Hematol., 30:285–96 (2002); and De Caterina R., Libby P., Peng H. B., Thannickal V. J., Rajavashisth T. B., Gimbrone M. A., Jr. et al. *Nitric oxide decreases cytokine-induced endothelial activation: Nitric oxide selectively reduces endothelial expression of adhesion molecules and proinflammatory cytokines.* J. Clin. Invest., 96:60–68 (1995)). This reaction serves to as a defense to combat the stress but these substances that are activated by nuclear kappa beta factor cannot distinguish between the stress that provoked the inflammation and the body's cells. Inflammatory cytokines as well as nitrogen and oxygen free radicals breakdown cellular membranes, damage DNA, depress enzyme functions, and cause cellular death of the agent inciting the stress but can also have the same effects on cells of the host.

Examples of Inflammatory Diseases and/or Disorders

Nathan classified inflammatory disorders with respect their effects upon the host and listed examples under each category (Nathan C., *Points of control in inflammation,* Nature, 420:846–52 (2002)). He asserted that inflammatory responses that affected the host consist of 1) disorders in which an important pathogenic role is assigned to inflammation, 2) diseases of infectious origin in which inflammation may contribute as much to pathology as does microbial toxicity, and 3) diseases of diverse origin in which post-inflammatory fibrosis is a principal cause of the pathology. The first category included Alzheimer's disease, anaphylaxis, ankylosing spondylitis, asthma, atherosclerosis, chronic obstructive pulmonary disease, Crohn's disease, gout, Hashimoto's thyroiditis, ischemic-reperfusion injury (occlusive and embolic stroke attacks and myocardial infarction), multiple sclerosis, osteoarthritis, pemphigus, periodic fever syndrome, psoriasis, rheumatoid arthritis, sarcoidosis, systemic lupus erythematosis, Type 1 diabetes mellitus, ulcerative colitis, vasculitides (Wegener's syndrome, Goodpasture's syndrome, giant cell arteritis, polyarteritis nodosa) and xenograft rejection. The second category consisted of bacterial dysentery, Chagas disease, cystic fibrosis pneumonia, filiarisis, heliobacter pylori gastritis, hepatitis C, influenza virus pneumonia, leprosy, neisseria or pneumococcal meningitis, post-streptococcal glomerulonephritis, sepsis syndrome, and tuberculosis. The third category included bleomycin-induced pulmonary fibrosis, chronic allograft rejection, idiopathic pulmonary fibrosis, hepatic cirrhosis (post-viral or alcoholic), radiation-induced pulmonary fibrosis, and schistosomiasis.

Inflammation plays a significant pathophysiologic role in several other diseases/conditions that were not cited by Nathan (Nathan, *Id.*). These include cardiovascular diseases such as peripheral vascular disease, coronary artery disease, angina pectoris, restenosis after relief of stenosis, arteriosclerotic plaque rupture, stroke, chronic venous insufficiency, cardiopulmonary bypass surgery, and chronic heart failure (Blake G. J., Ridker P. M., *Inflammatory bio-markers and cardiovascular risk prediction,* J. Intern. Med., 252: 283–94 (2002); Emsley H. C., Tyrrell P. J. *Inflammation and infection in clinical stroke,* J. Cereb. Blood Flow Metab., 22:1399–419 (2002); Esch T., Stefano G., Fricchione G., Benson H., *Stress-related diseases—a potential role for nitric oxide,* Med. Sci. Monit., 8:RA103-RA118 (2002); Forrester J. S. *Prevention of plaque rupture: a new paradigm of therapy,* Ann. Intern. Med., 137:823–33 (2002); Paulus W. J., *Cytokines and heart failure,* Heart Fail. Monit., 1:50–56 (2000); Ross J. S., Stagliano N. E., Donovan M. J., Breitbart R. E., Ginsburg G. S., *Atherosclerosis: a cancer of the blood vessels?* Am. J. Clin. Pathol., 116 Suppl:S97–107 (2001); Signorelli S. S., Malaponte M. G., Di Pino L., Costa M. P., Pennisi G., Mazzarino M. C., *Venous stasis causes release of interleukin* 1*beta* (*IL*-1*beta*), *interleukin* 6 (*IL*-6) *and tumor necrosis factor alpha* (*TNFalpha*) *by monocyte-macrophage,* Clin. Hemorheol. Microcirc., 22:311–16 (2000)).

Inflammation plays a role in several neuromuscular diseases that include amyotrophic lateral sclerosis, myasthenia gravis, Huntington's chorea, Parkinson's disease, fibromyalgia, chronic fatigue syndrome, complex regional pain syndrome, muscular dystrophy, myopathy, obstructive sleep apnea syndrome, cerebral palsy, neuropathy, HIV dementia, and head trauma/coma (Anderson E., Zink W., Xiong H., Gendelman H. E., *HIV*-1-*associated dementia: a metabolic encephalopathy perpetrated by virus-infected and immune-competent mononuclear phagocytes,* J. Acquir. Immune. Defic. Syndr., 31 Suppl 2:S43-S54 (2002); Carrieri P. B., Marano E., Perretti A., Caruso G., *The thymus and myasthenia gravis: immunological and neurophysiological aspects,* Ann. Med., 31 Suppl 2:52–56 (1999); Empl M., Renaud S., Erne B., Fuhr P., Straube A., Schaeren-Wiemers N. et al., *TNF-alpha expression in painful and nonpainful neuropathies,* Neurology, 56:1371–77 (2001); Gahm C., Holmin S., Mathiesen T., *Nitric oxide synthase expression after human brain contusion,* Neurosurgery, 50:1319–26 (2002); Hunot S., Hirsch E. C., *Neuroinflammatory processes in Parkinson's disease,* Ann. Neurol., 53 Suppl 3:S49–S58 (2003); Huygen F. J., De Bruijn A. G., De Bruin M. T., Groeneweg J. G., Klein J., Zijistra F. J., *Evidence for local inflammation in complex regional pain syndrome type* 1 *Mediators,* Inflamm., 11:47–51 (2002); Kadhim H., Sebire G., *Immune mechanisms in the pathogenesis of cerebral palsy: implication of proinflammatory cytokines and T lymphocytes, Eur. J. Paediatr. Neurol.,* 6:139–42 (2002); Kumar A., Boriek A. M., *Mechanical stress activates the nuclear factor-kappaB pathway in skeletal muscle fibers: a possible role in Duchenne muscular dystrophy,* FASEB J., 17:386–96 (2003); Mammarella A., Ferroni P., Paradiso M., Martini F., Paoletti V., Morino S. et al., *Tumor necrosis factor-alpha and myocardial function in patients with myotonic dystrophy type* 1, *J. Neurol. Sci.,* 201:59–64 (2002); Mohanakumar K. P., Thomas B., Sharma S. M., Muralikrishnan D., Chowdhury R., Chiueh C. C., *Nitric oxide: an antioxidant and neuroprotector,* Ann. N.Y. Acad. Sci., 962:389–401 (2002); Ohga E, Tomita T, Wada H, Yamamoto H, Nagase T, Ouchi Y. *Effects of obstructive sleep apnea on circulating ICAM*-1, *IL*-8, *and MCP*-1, J. Appl. Physiol., 94:179–84 (2003); Patarca R., *Cytokines and chronic fatigue syndrome,* Ann. N.Y. Acad. Sci., 933:185–200 (2001); Poloni M., Facchetti D., Mai R., Micheli A., Agnoletti L., Francolini G. et al., *Circulating levels of tumour necrosis factor-alpha and its soluble receptors are increased in the blood of patients with amyotrophic lateral sclerosis,* Neurosci. Lett., 287: 211–14 (2000); Tews D. S., Goebel H. H., *Cytokine expression profile in idiopathic inflammatory myopathies,* J. Neuropathol. Exp. Neurol., 55:342–47 (1996); and Boguniewicz M., Leung D. Y., *Pathophysiologic mechanisms in atopic dermatitis,* Semin. Cutan. Med. Surg., 20:217–25 (2001)).

Skin disorders such as atopic dermatitis, urticarias, pressure ulcers, burns and Behcet's disease have a major inflammatory component (Boguniewicz M, Leung D Y. *Pathophysiologic mechanisms in atopic dermatitis,* Semin. Cutan. Med. Surg., 20:217–25 (2001); Frezzolini A., De Pita O., Cassano N., D'Argento V., Ferranti G., Filotico R. et al., *Evaluation of inflammatory parameters in physical urticarias and effects of an anti-inflammatory/antiallergic treatment,* Int. J. Dermatol., 41:431–38 (2002); Schwacha M. G., *Macrophages and post-burn immune dysfunction,* Burns, 29:1–14 (2003); Ladwig G. P., Robson M. C., Liu R., Kuhn M. A., Muir D. F., Schultz G. S., *Ratios of activated matrix metalloproteinase*-9 *to tissue inhibitor of matrix metalloproteinase*-1 *in wound fluids are inversely correlated with healing of pressure ulcers,* Wound. Repair Regen., 10:26–37 (2002); Meador R., Ehrlich G., Von Feldt J. M., *Behcet's disease: immunopathologic and therapeutic aspects,* Curr. Rheumatol. Rep., 4:47–54 (2002)).

Acute injuries such as sprains (e.g., tennis elbow, whiplash injury) are associated with an inflammatory response. Other injuries with a strong inflammatory response include intervertebral disc disorder, sciatica, dislocations, fractures, and carpal tunnel syndrome (Freeland A. E., Tucci M. A., Barbieri R. A., Angel M. F., Nick T. G., *Biochemical evaluation of serum and flexor tenosynovium in carpal tunnel syndrome,* Microsurgery, 22:378–85 (2002); Brisby H., Olmarker K., Larsson K., Nutu M., Rydevik B., *Proinflammatory cytokines in cerebrospinal fluid and serum in patients with disc herniation and sciatica,* Eur. Spine J., 11:62–66 (2002); Kivioja J., Rinaldi L., Ozenci V., Kouwenhoven M., Kostulas N., Lindgren U. et al., *Chemokines and their receptors in whiplash injury: elevated RANTES and CCR*-5, J. Clin. Immunol., 21:272–77 (2001)). Gaucher disease, acute pancreatitis, and diverticulitis are associated with an inflammatory process (Bhatia M., Brady M., Shokuhi S., Christmas S., Neoptolemos J. P., Slavin J., *Inflammatory mediators in acute pancreatitis,* J. Pathol., 190:117–25 (2000); Cox T. M., *Gaucher disease: understanding the molecular pathogenesis of sphingolipidoses,* J. Inherit. Metab. Dis., 24 Suppl 2:106–21 (2001); Rogler G., Andus T., *Cytokines in inflammatory bowel disease,* World J. Surg., 22:382–89 (1998)). Interstitial cystitis and chronic prostatitis are generally sterile inflammatory disorders (Richard G., Batstone D., Doble A., *Chronic prostatitis,* Curr. Opin. Urol., 13:23–29 (2003); Erickson D. R., Xie S. X., Bhavanandan V. P., Wheeler M. A., Hurst R. E., Demers L. M. et al., *A comparison of multiple urine markers for interstitial cystitis,* J. Urol., 167:2461–69 (2002)).

The physiologic process of aging as well as the geriatric syndrome of frailty are associated with increasing levels of inflammatory cytokines and upregulated iNOS (Bruunsgaard H., Pedersen M., Pedersen B. K., *Aging and proin-*

*flammatory cytokines,* Curr. Opin. Hematol., 8:131 . 36 (2001); Brod S. A., *Unregulated inflammation shortens human functional longevity,* Inflamm. Res., 49:561–70 (2000); Grimble R. F., *Inflammatory response in the elderly,* Curr. Opin. Clin. Nutr. Metab Care, 6:21–29 (2003); Leng S., Chaves P., Koenig K., Walston J., *Serum interleukin-*6 *and hemoglobin as physiological correlates in the geriatric syndrome of frailty: a pilot study,* J. Am. Geriatr. Soc., 50:1268–71 (2002)). Endometriosis has high levels of levels of IL-8 in the tissue stroma (Arici A., *Local cytokines in endometrial tissue: the role of interleukin-*8 *in the pathogenesis of endometriosis.* Ann. N.Y. Acad. Sci., 955:101–09 (2002)).

Several neoplasms thrive in a milieu of inflammatory tissue that is activated by nuclear factor kappa beta. These include acute myeloblastic leukemia, melanoma, lung cancer, myelidysplastic syndrome, multiple myeloma, Kaposi's sarcoma in conjunction with HIV-1, and Hodgkin's disease (Berenson J. R., Ma H. M., Vescio R., *The role of nuclear factor-kappaB in the biology and treatment of multiple myeloma,* Semin. Oncol., 28:626–33 (2001); Dezube B. J., *The role of human immunodeficiency virus-I in the pathogenesis of acquired immunodeficiency syndrome-related Kaposi's sarcoma: the importance of an inflammatory and angiogenic milieu,* Semin. Oncol., 27:420–23 (2000); Hsu H. C., Lee Y. M., Tsai W. H., Jiang M. L., Ho C. H., Ho C. K, et al., *Circulating levels of thrombopoietic and inflammatory cytokines in patients with acute myeloblastic leukemia and myelodysplastic syndrome,* Oncology, 63:64–69 (2002); Yamamoto Y., Gaynor R. B., *Therapeutic potential of inhibition of the NF-kappaB pathway in the treatment of inflammation and cancer,* J. Clin. Invest., 107:135–42 (2001); Zhu N., Eves P. C., Katerinaki E., Szabo M., Morandini R., Ghanem G. et al., *Melanoma cell attachment, invasion, and integrin expression is upregulated by tumor necrosis factor alpha and suppressed by alpha melanocyte stimulating hormone,* J. Invest. Dermatol., 119:1165–71 (2002)).

The inflammatory process associated with several neoplasms produces cancer-related fatigue (Kurzrock R., *The role of cytokines in cancer-related fatigue,* Cancer, 92:1684–88 (2001)). Hemolytic anemias such as sickle cell disease, hemolytic-uremic syndrome, and thalassemia have strong inflammatory components (Abboud M. R., Taylor E. C., Habib D., Dantzler-Johnson T., Jackson S. M., Xu F. et al., *Elevated serum and bronchoalveolar lavage fluid levels of interleukin* 8 *and granulocyte colony-stimulating factor associated with the acute chest syndrome in patients with sickle cell disease,* Br. J. Haematol., 111:482–90 (2000); Andreoli S. P., *The pathophysiology of the hemolytic uremic syndrome,* Curr. Opin. Nephrol. Hypertens., 8:459–64 (1999); Archararit N., Chuncharunee S., Pornvoranunt A., Atamasirikul K., Rachakom B., Atichartakarn V., *Serum C-reactive protein level in postsplenectomized thalassemic patients,* J. Med. Assoc. Thai., 83 Suppl 1:S63-S69 (2000); Wun T., Cordoba M., Rangaswami A., Cheung A. W., Paglieroni T., *Activated monocytes and platelet-monocyte aggregates in patients with sickle cell disease,* Clin. Lab Haematol., 24:81–88 (2002)).

Mental disorders such as depression, autism, and schizophrenia may their basis in an inflammatory process (Anisman H., Merali Z., *Cytokines, stress and depressive illness: brain-immune interactions,* Ann. Med., 35:2–11 (2003); Croonenberghs J., Bosmans E., Deboutte D., Kenis G., Maes M., *Activation of the inflammatory response system in autism,* Neuropsychobiology, 45:1–6 (2002); Naudin J., Capo C., Giusano B., Mege J. L., Azorin J. M., *A differential role for interleukin-*6 *and tumor necrosis factor-alpha in schizophrenia?* Schizophr. Res., 26:227–33 (1997)).

Disorders of the upper airway with an inflammatory component include allergic rhinitis, nasal and sinus polyps, and chronic sinusitis (Churg A., Wang R. D., Tai H., Wang X., Xie C., Dai J. et al., *Macrophage metalloelastase mediates acute cigarette smoke-induced inflammation via tumor necrosis factor-alpha release,* Am. J. Respir. Crit Care Med., 167:1083–89 (2003); Carayol N., Crampette L., Mainprice B., Ben Soussen P., Verrecchia M., Bousquet J. et al., *Inhibition of mediator and cytokine release from dispersed nasal polyp cells by mizolastine,* Allergy 57:1067–70 (2002); Lennard C. M., Mann E. A., Sun L. L., Chang A. S., Bolger W. E., *Interleukin-*1 *beta, interleukin-*5, *interleukin-*6, *interleukin-*8, *and tumor necrosis factor-alpha in chronic sinusitis: response to systemic corticosteroids,* Am. J. Rhinol., 14:367–73 (2000)).

Inflammation is a strong feature of smoking, chronic bronchitis, bronchiectasis, and pneumoconiosis such as beryllium disease (Snider G. L., *Understanding inflammation in chronic obstructive pulmonary disease: the process begins,* Am. J. Respir. Crit Care Med., 167:1045–46 (2003); Maier L. A., *Genetic and exposure risks for chronic beryllium disease,* Clin. Chest Med., 23:827–39 (2002)). A severe inflammatory process occurs in adult respiratory distress syndrome (ARDS), severe acute respiratory syndrome (SARS), and smoke burn inhalation injury to the lungs (Chan-Yeung M., Yu W. C.. *Outbreak of severe acute respiratory syndrome in Hong Kong Special Administrative Region: case report,* BMJ, 326:850–52 (2003); Hamacher J., Lucas R., Lijnen H.R., Buschke S., Dunant Y., Wendel A. et al., *Tumor necrosis factor-alpha and angiostatin are mediators of endothelial cytotoxicity in bronchoalveolar lavages of patients with acute respiratory distress syndrome,* Am. J. Respir. Crit Care Med., 166:651–56 (2002); Enkhbaatar P., Murakami K., Shimoda K., Mizutani A., Traber L., Phillips G. B. et al., *The inducible nitric oxide synthase inhibitor BBS-*2 *prevents acute lung injury in sheep after burn and smoke inhalation injury,* Am. J. Respir. Crit Care Med., 167:1021–26 (2003)). Mechanical ventilation associated with overinflation of the lungs produces an inflammatory response (Held H. D., Boettcher S., Hamann L., Uhlig S., *Ventilation-induced chemokine and cytokine release is associated with activation of nuclear factor-kappaB and is blocked by steroids,* Am. J. Respir. Crit Care Med., 163: 711–16 (2001)).

Aseptic loosening of total hip replacement is due to an inflammatory process (Hukkanen M., Corbett S. A., Batten J., Konttinen Y. T., McCarthy I. D., Maclouf J. et al., *Aseptic loosening of total hip replacement. Macrophage expression of inducible nitric oxide synthase and cyclo-oxygenase-*2, *together with peroxynitrite formation, as a possible mechanism for early prosthesis failure,* J. Bone Joint Surg. Br., 79:467–74 (1997)), as is aseptic necrosis of the hip from other causes such as radiation and sickle cell anemia. Inflammation underlies periodontal disease (Greenwell H., Bissada N. F., *Emerging concepts in periodontal therapy,* Drugs, 62:2581–87 (2002)). Brain death causes a generalized inflammatory response which can adversely affect the viability of the donor organs (Stoica S. C., Goddard M., Large S. R., *The endothelium in clinical cardiac transplantation,* Ann. Thorac. Surg., 73:1002–08 (2002)).

About one-third of patients after cardiopulmonary bypass for open heart surgery develop severe systemic inflammation with a vasodilatory syndrome (Kilger E., Weis F., Briegel J., Frey L., Goetz A. E., Reuter D. et al., *Stress doses of hydrocortisone reduce severe systemic inflammatory*

*response syndrome and improve early outcome in a risk group of patients after cardiac surgery,* Crit Care Med., 31:1068–74 (2003)). Repeated cooling and drying of peripheral airways can cause asthma in winter athletes may be as a result of repeated deep breathing with cold air during winter sports activities (Davis M. S., Schofield B., Freed A. N., *Repeated Peripheral Airway Hyperpnea Causes Inflammation and Remodeling in Dogs,* Med. Sci. Sports Exerc., 35:608–16 (2003)). Cellulite might have as its basis chronic inflammation due to decreased dermal blood flow (Rossi A. B., Vergnanini A. L., *Cellulite: a review,* J. Eur. Acad. Dermatol. Venereol., 14:251–62 (2000)).

Sequence of Immunologic Response to Stress

The following description summarizes how stress at the injured affected site provokes the inflammatory response that is an important feature of most chronic diseases as well as soft tissue and skeletal acute injuries. Stress activates nuclear factor kappa beta that is expressed from cellular sources. This in turn initiates release of inflammatory cytokines from white blood cells and native cells at the site of the stress. These inflammatory cytokines comprise interleukins 1 beta, 2, 6, 8 and 18 but could be others as our knowledge of these molecules are expanded. Tumor necrosis factor alpha is also released that in turn stimulates the release of metalloproteinases. The inflammatory cytokines activate inducible nitric oxide synthase (iNOS) present in white blood cells, macrophages and other cells that release mMol/L quantities of nitric oxide into the circulation; such quantities of nitric oxide also cause more cytokine release. Further, high levels of nitric oxide form nitrogen free radicals that are potentially destructive to the stress as well as tissues of the host. Activation of white blood cells by inflammatory cytokines causes them to release oxygen free radicals that are also tissue destructive. Nuclear kappa beta factor also causes release of endothelin-1, a potent vasoconstrictor substance.

Nuclear factor kappa beta also mediates transcription of genes for adhesion molecules from lymphocytes, monocytes, and macrophages to the endothelial wall. These substances include 1) L, E, and P selectins that tether white blood cells to endothelial surface 2) integrins that firmly attach such cells to endothelial surface, and 3) intracellular adhesion molecules (ICAM-1 and ICAM-2) and vascular cellular adhesion molecules (VCAM-1) that glue the white blood cells to the endothelial surface thereby targeting the action of inflammatory cytokines to a local site. Moreover, both inflammatory cytokines and adhesion molecules may spillover into general circulation and produce high concentrations of free nitrogen and oxygen radicals.

Treatment of stress related illnesses should theoretically be directed to the cause but for most of these diseases or conditions the cause is unknown. If the stress is known to be of bacterial, viral, protozoan, or parasitic origin where specific pharmacological agents are available, then the cause can be treated. Otherwise, therapy is directed to treating the manifestations of the stress that involves suppression of inflammatory cytokines as well as oxygen and nitrogen free radicals. The time-honored treatment of this aspect of the inflammatory process is corticosteroids. Non-steroidal anti-inflammatory drugs (NSAID's), e.g., COX1 and/or COX2 inhibitors also have been used mainly for musculoskeletal inflammatory processes.

Corticosteroids are extremely effective anti-inflammatory agents that suppress formation of the transcriptional gene, nuclear factor kappa beta and hence release of inflammatory cytokines, tumor necrosis factor, adhesion molecules; these drugs also suppress iNOS activity and diminish formation of nitrogen and oxygen free radicals (Beauparlant P., Hiscott J., *Biological and biochemical inhibitors of the NF-kappa B/Rel proteins and cytokine synthesis,* Cytokine Growth Factor Rev., 7:175–90 (1996)). But there is a price to pay for the anti-inflammatory effects in terms of serious side effects such as Cushingoid syndrome, acne, osteoporosis with fractures, myopathy, dementia, diabetes, hypertension, weight gain, peripheral edema, duodenal ulcer, glaucoma, and cataracts among others (Belvisi M. G., Brown T. J., Wicks S., Foster M. L., *New Glucocorticosteroids with an improved therapeutic ratio?* Pulm. Pharmacol. Ther., 14:221–27 (2001)). NSAID's side effects include gastritis and bleeding, renal toxicity, and tendency to precipitate acute myocardial infarction (Bing R. J., Lomnicka M., *Why do cyclo-oxygenase-*2 *inhibitors cause cardiovascular events?* J. Am. Coll. Cardiol., 39:521–22 (2002); Dequeker J., *NSAIDs/corticosteroids—primum non nocere,* Adv. Exp. Med. Biol., 455: 319–25 (1999)).

By contrast, periodic acceleration that causes release of small quantities of nitric oxide in nMol/L concentrations is devoid of side effects since the molecule originates in the body itself as a natural response to increased pulsatile shear stress. Nitric oxide in small amounts is an effective suppressant of nuclear factor kappa beta factor as well as the protracted release of large quantities of nitric oxide from inducible nitric oxide synthase (iNOS) activity that create destructive nitrogen free radicals (Stefano G. B., Prevot V., Cadet P., Dardik I., *Vascular pulsations stimulating nitric oxide release during cyclic exercise may benefit health: a molecular approach* (*review*), Int. J. Mol. Med., 7:119–29 (2001)). In contrast to some patients with chronic inflammatory diseases who do not respond to the pharmacological administration of corticosteroids (see, Bantel H., Schmitz M. L., Raible A., Gregor M., Schulze-Osthoff K., *Critical role of NF-kappaB and stress-activated protein kinases in steroid unresponsiveness,* FASEB J. 16:1832–34 (2002)), this unresponsiveness is not the case for physiological release of nitric oxide from endothelial nitric oxide synthase (eNOS).

Application of Periodic Acceleration to Inflammatory Diseases/Disorders

Nitric oxide can be released from endothelial nitric oxide synthase in the vascular endothelium by means of periodic acceleration which produces pulsatile shear stress owing to addition of sinusoidal pulses to the circulation with each acceleration and deceleration (see, the '976 patent and the '422 application, also, Adams J. A., Mangino M. J., Bassuk J., Sackner M. A., *Hemodynamic effects of periodic G(z) acceleration in meconium aspiration in pigs,* J. Appl. Physiol., 89:2447–52 (2000); Hoover G. N., Ashe W. F., *Respiratory response to whole body vertical vibration,* Aerosp. Med., 33:980–84 (1962); Hutcheson I. R., Griffith T. M., *Release of endothelium-derived relaxing factor is modulated by both frequency and amplitude of pulsatile flow,* Am. J. Physiol., 261:257H–62H (1991)).

If a subject's pulse rate is 60 per minute and periodic acceleration is carried out at 140 times per minute, then the number of pulses in the circulation will be 60+140=200 pulses per minute. The pulses produced by periodic acceleration are generally of lesser amplitude than the natural pulse and superimposed upon it. Animal studies revealed that serum nitrite as measured with a nitric oxide electrode increased 450% above baseline during application of periodic acceleration and remained elevated at this level three-hours after termination of the periodic acceleration treatment.

Figure 20:
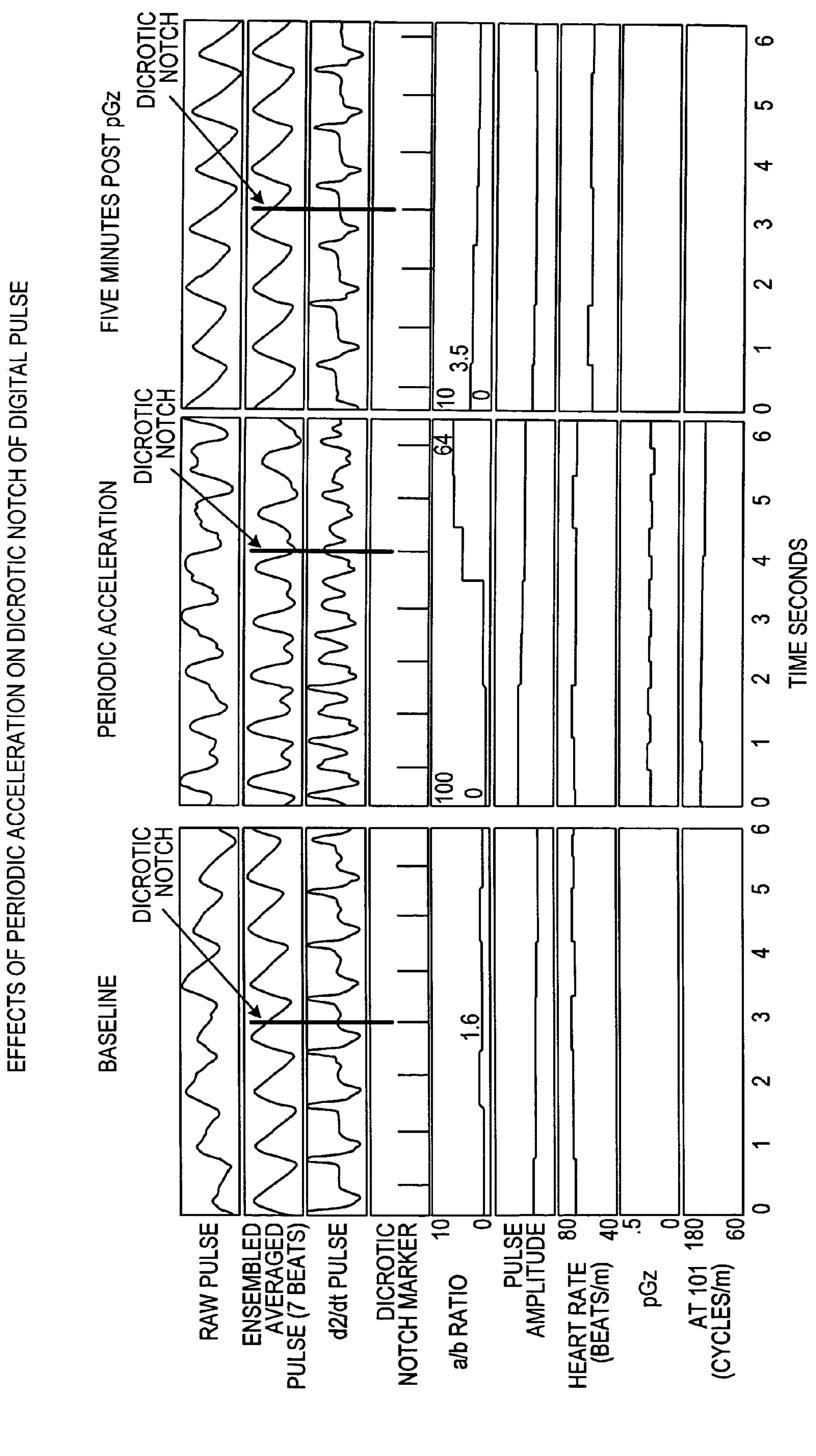
FIG. 20 shows three graphs that show the effects of periodic acceleration on the Dicrotic Notch according to a preferred embodiment of the present invention.

In humans, the digital arterial pulse serves as a means to non-invasively assess nitric oxide release from eNOS during periodic acceleration. This is accomplished by observing descent of the dicrotic notch in the diastolic limb of the pulse waveform (FIG. 20). This is because the dicrotic notch is formed by pulse wave reflection. Since nitric oxide dilates the resistance blood vessels as a specific effect, the pulse wave travels further into the periphery of the arterial circulation and returns later to the digital pulse thereby causing the dicrotic notch to occur later in the diastolic limb of the pulse. During periodic acceleration, the added pulses prevent recognition of the dicrotic notch in the raw electric photo-plethysmographic waveform and it is necessary to utilize an electrocardigraphic R-wave triggered ensemble-averaging routine (nominally seven beats) to depict the natural pulse with its dicrotic notch.

FIG. 20 depicts a pre-periodic acceleration recording on the left panel (Baseline), a recording during periodic acceleration in the middle panel (Periodic Acceleration), and a recovery recording on the right panel. The digital pulse measured with a photoelectric plethysmograph depicts added pulses and distortion during periodic acceleration labeled as Raw Pulse. This is processed by an ECG R-wave triggered 7 beat ensembled-averaging routine to eliminate the added pulses from periodic acceleration thereby allowing the dicrotic notch to be displayed. Thus, each pulse displayed in the ensembled average represents the mean of 7 preceding pulses. The dicrotic notch descends down the diastolic limb of the pulse wave with periodic acceleration treatment. The detection of the dicrotic notch is aided by computing the second derivative of the ensembled-averaged pulse wave. The largest deflection in diastole generally identifies the dicrotic notch automatically; the observers have the capability in the software program to adjust this point from their visual observations. The descent of the dicrotic notch as reflected by the increase in a/b ratio signifies that nitric oxide has been released into the circulation causing dilation of resistance blood vessels thereby lengthening the pathway for wave reflection and its time of return that creates the dicrotic notch. In the late 1970's, FDA recommended that the position of the dicrotic notch as a means to assay the absorption of nitroglycerin from skin patch delivery systems. The dicrotic notch position is quantified by measurement of the a/b ratio where 'a' is the pulse amplitude and 'b' is the distance of the dicrotic notch above the end-diastolic level. Dicrotic notches that fall on the subsequent pulse wave are arbitrarily assigned a value of '100' (middle panel). The higher the values of the dicrotic notch the greater the nitric oxide effect.

Figure 21:
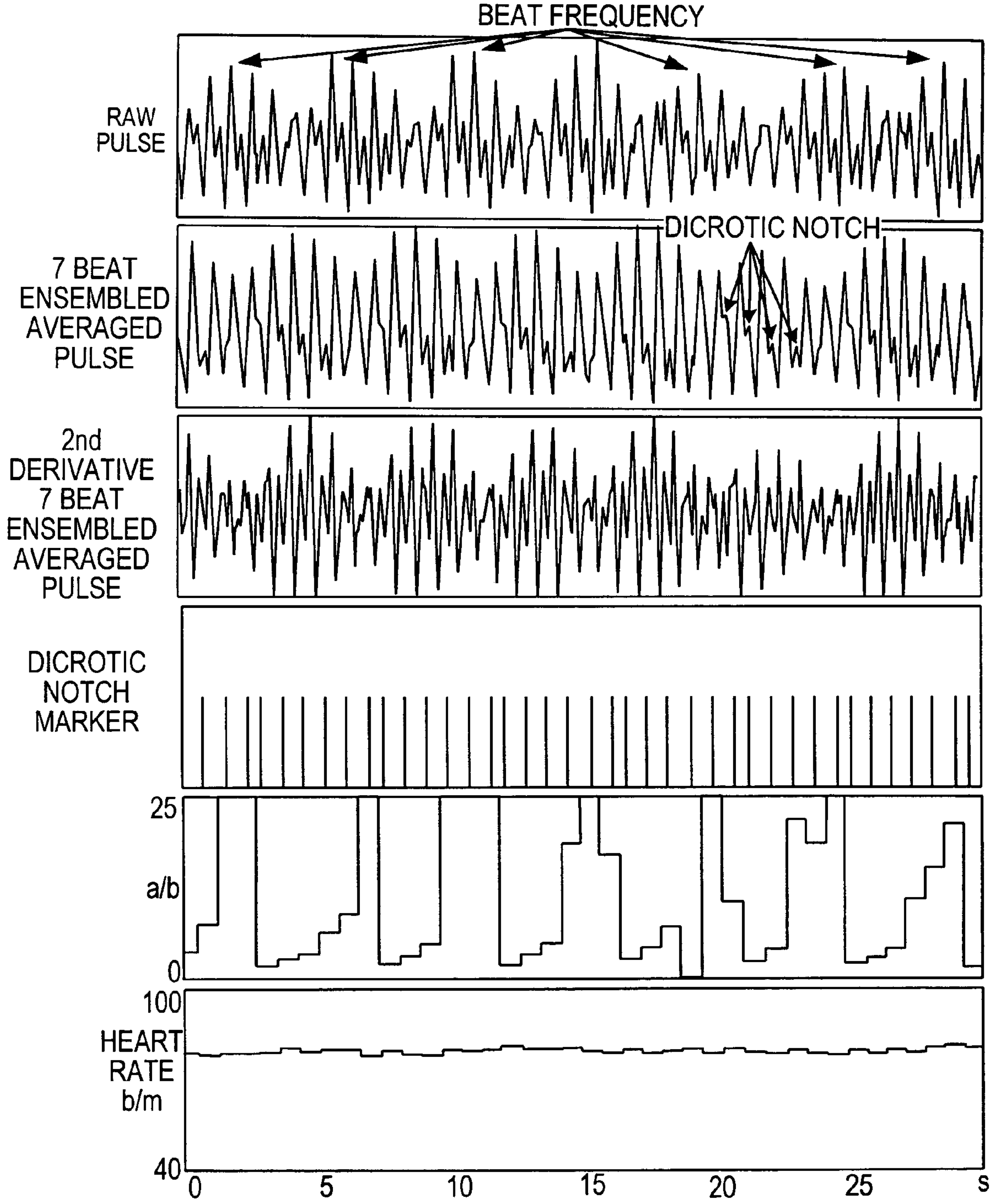
FIG. 21 is a graph showing the beat frequency and cyclic movement of the dicrotic notch during treatment according to a preferred embodiment of the present invention.

Periodic acceleration releases nitric oxide sporadically or cyclically into the circulation since homeostasis in a non-exercising subject needs to be maintained (FIG. 21). FIG. 21 depicts the cyclic release of nitric oxide from endothelial nitric oxide synthase during periodic acceleration. Upward and downward movements of the dicrotic notch in the ensembled-averaged pulse wave as well as the changing values of the a/b ratio demonstrate this phenomenon. The detection of the dicrotic notch position is aided by identifying the largest positive deflection of the ensembled-averaged pulse waveform in diastole by a software program (FIG. 20). The investigator can adjust this point in the software program if it disagrees with visual observations. The software program computes a standard index for quantifying the effectiveness of nitric oxide release into the circulation. This index consists of the amplitude of the pulse, termed 'a', and the height of the dicrotic notch above the end-diastolic level termed, 'b'. The ratio of a/b reflects the amount of nitric oxide released into the circulation (Imhof P. R., Vuillemin T., Gerardin A., Racine A., Muller P., Follath F., *Studies of the bioavailability of nitroglycerin from a transdermal therapeutic system* (*Nitroderm TTS*), Eur. J. Clin. Pharmacol., 27:7–12 (1984)).

Since periodic acceleration may shift the dicrotic notch into the next pulse wave, the a/b ratio would compute to infinity; arbitrarily, such values are taken as 100. As can be seen in Table 1 below, that provides a listing of published peak values of the a/b ratio with administration of nitric oxide donor drugs, peak values of the a/b ratio in normal humans and patients produced with periodic acceleration are far higher than with the drugs. Since this response occurred in both healthy and diseased persons, this indicates that endothelial dysfunction does not limit response to periodic acceleration.

TABLE 1

| Investigator | Drug or Device | Peak a/b* Response (% baseline) |
|---|---|---|
| Imhof 1980 | NTG 12 mg transdermal patch (n = 1) | 262 |
| Lund 1986 | NTG 0.13 mg sublingual (n = 1) | 138 |
| | NTG 1 mg sublingual (n = 1) | 130 |
| | NTG 0.25 mg sublingual (n = 1) | 227 |
| | NTG 20 mg ointment (n = 1) | 170 |
| Wiegand 1992 | NTG 0.8 mg sublingual (n = 10) | 184 |
| Buschmann 1993 | NTG 0.4 mg spray (n = 12) | 164 |
| Stengele 1996 | NTG 0.8 mg sublingual (n = 10) | 145 |
| Chowienczyk 1999 | NTG 0.8 mg spray (n = 12) | 147 |
| | NTG 0.1 mg/min I.V. (n = 1) | 305 |
| | Albuterol 0.4 mg inhaled (n = 1) | 135 |
| | Albuterol 20 ug/min I.V. (n = 1) | 224 |
| Sackner 2003 | AT 101 for 45 minutes (13 normals; age 46, SD 15)) | 1127 |
| Sackner 2003 | AT 101 for 45 minutes (25 patients*; age 62, SD 15) | 3909 |

Osteoarthritis, Parkinsonism, Multiple Sclerosis, Neuropathy, Carpal Tunnel, Restless Legs Syndrome, COPD, Fibromyalgia, Pulm. Fibrosis, Pulm Hypert., Post CABG, Chronic Venous Insufficiency, Interstitial Cystitis Nitric oxide produced in small quantities by upregulation of eNOS has the same or better suppressant action on nuclear factor kappa beta and iNOS as corticosteroids without side effects. In contrast to corticosteroids, it prevents osteoporosis, reduces insulin resistance, increases brain blood flow, lowers blood pressure in hypertension, heals duodenal ulcer and lowers pressure in open angle glaucoma. Moderate exercise releases nitric oxide from eNOS but distribution to non-skeletal and cardiac muscle sites, i.e., brain, gut, liver, and kidney may not take place since exercise diverts blood flow to the working muscles. However, periodic acceleration that induces shear stress to endothelium through addition of pulses to the circulation releases nitric oxide from eNOS that is preferentially distributed to the brain, gastrointestinal tract, liver, kidneys as well as the heart at the expense of skeletal muscle (Adams J. A., Mangino M. J., Bassuk J., Kurlansky P., Sackner M. A., *Regional blood flow during periodic acceleration,* Crit Care Med., 29:1983–88 (2001)).

Figure 22:
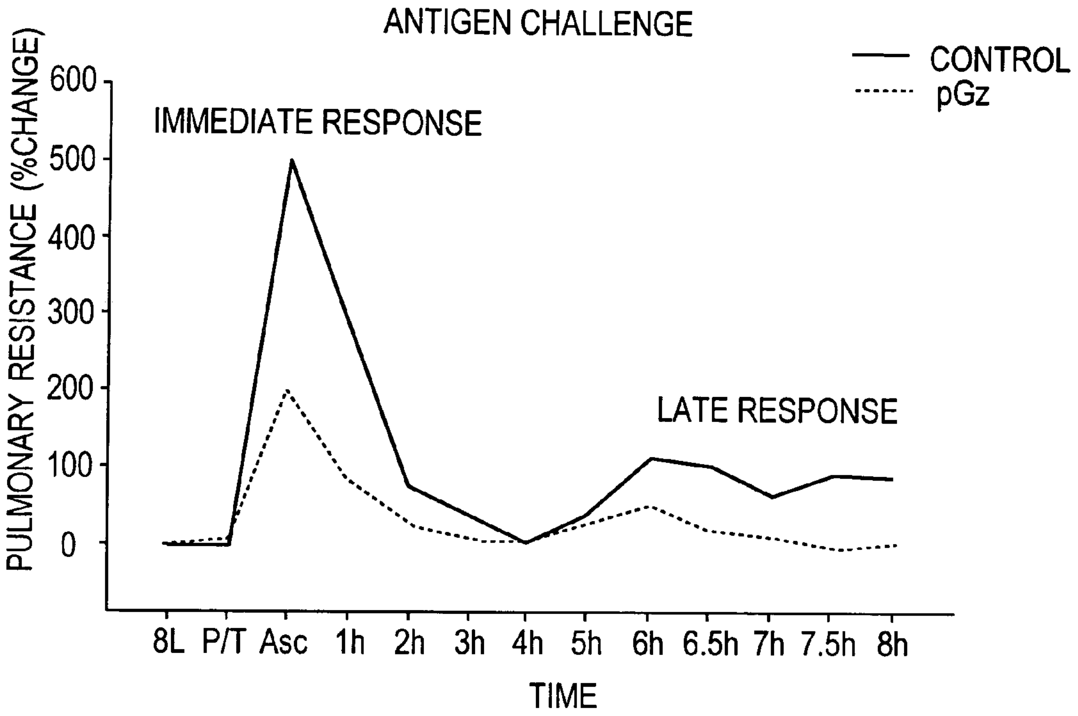
FIG. 22 shows two graphs demonstrating the effects of pretreating antigen challenged allergic sheep with periodic acceleration according to a preferred embodiment of the present invention.
Figure 22:
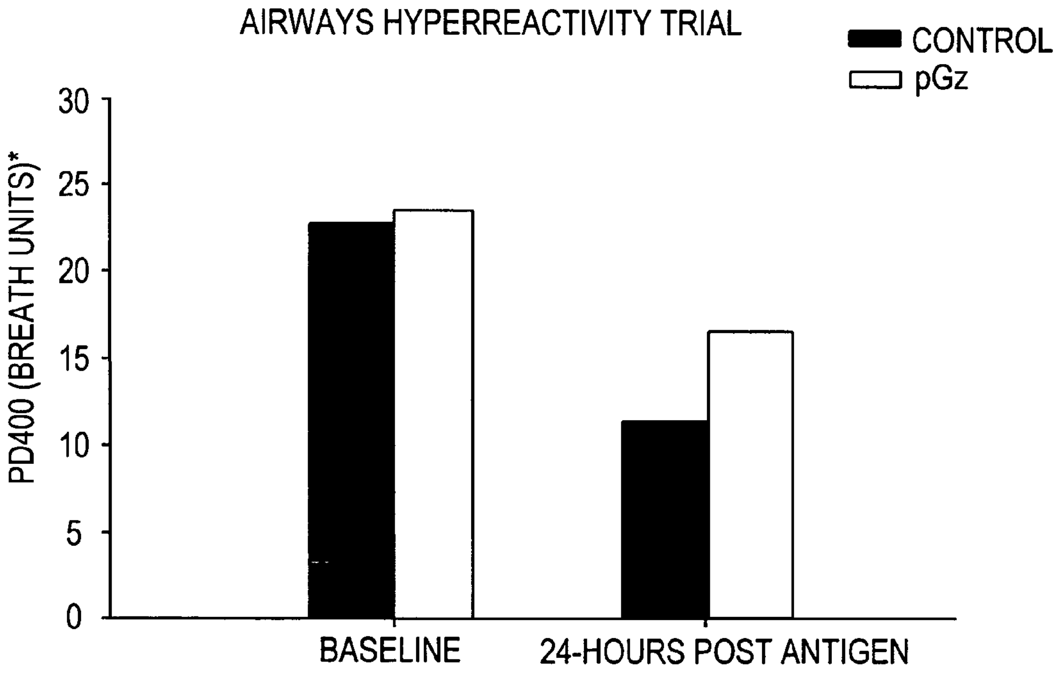

FIG. 22 further demonstrates that periodic acceleration has immunosuppressant properties similar to corticosteroids in an allergic sheep model. Removing the mattress 101 from the platform and attaching a cart that restrained the conscious sheep in its natural standing position allowed treatment with periodic acceleration using the invention in this application. Inhalation of an antigen (ascaris suum) to which these sheep are naturally sensitive produces immediate bronchoconstriction as signified by increased pulmonary resistance, an indicator of airways narrowing that mimics allergic-induced human asthma (FIG. 22).

About six hours later, there is a less intense rise in pulmonary resistance termed the late response. Twenty-four hours after the initial antigen challenge, carbachol, a non-specific bronchoconstrictor drug, is administered in graded doses. This assesses whether the airways remain hyperreactive to non-specific stimuli after the antigen challenge. The sheep that had not yet been treated with periodic acceleration required less carbachol 24-hours after an antigen challenge several days prior to the antigen challenge with periodic acceleration (FIG. 22, lower half of figure labeled control). In terms of human asthma, this suggests that the propensity for bronchoconstriction with non-specific stimuli such as breathing cold air, undergoing mental stress, and vigorously exercising would still be operative. Periodic acceleration administered for one-hour prior to antigen challenge blunted the immediate and delayed bronchoconstrictor responses but did not decrease airways hyperreactivity to the control carbachol administration 24-hours later labeled pGz in FIG. 22, lower half of figure.

Figure 23:
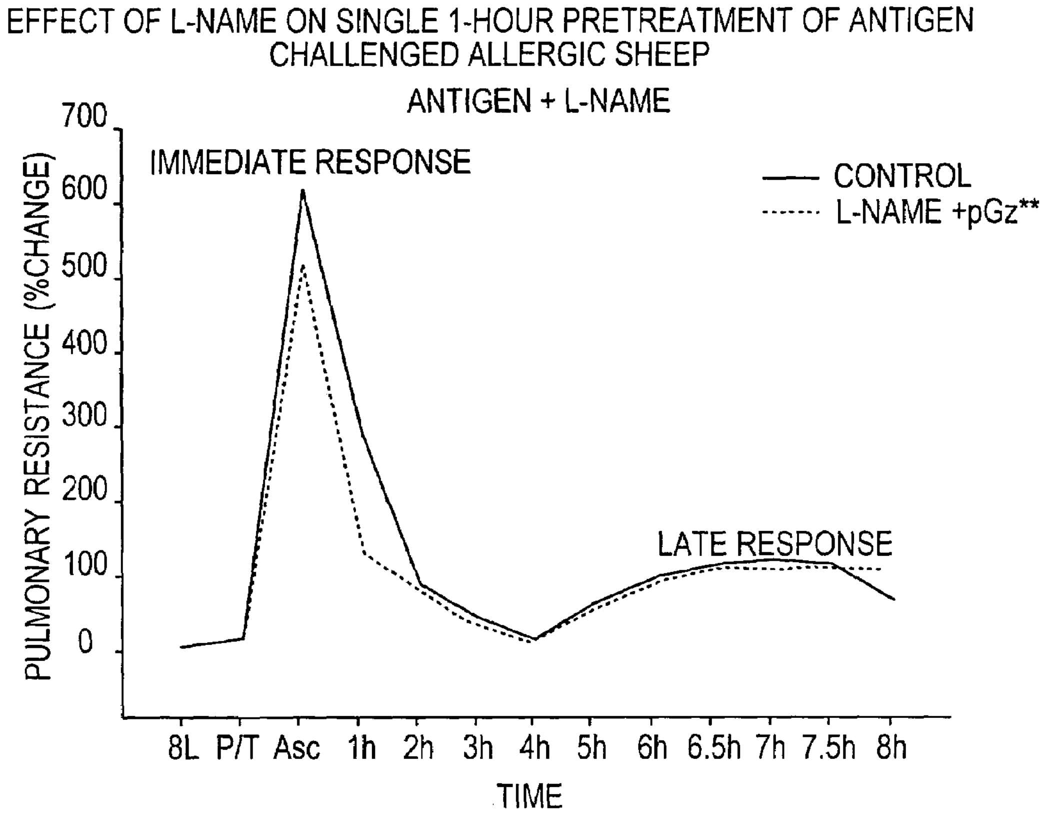
FIG. 23 shows two graphs demonstrating the effects of pretreating antigen challenged allergic sheep with L-NAME.
Figure 23:
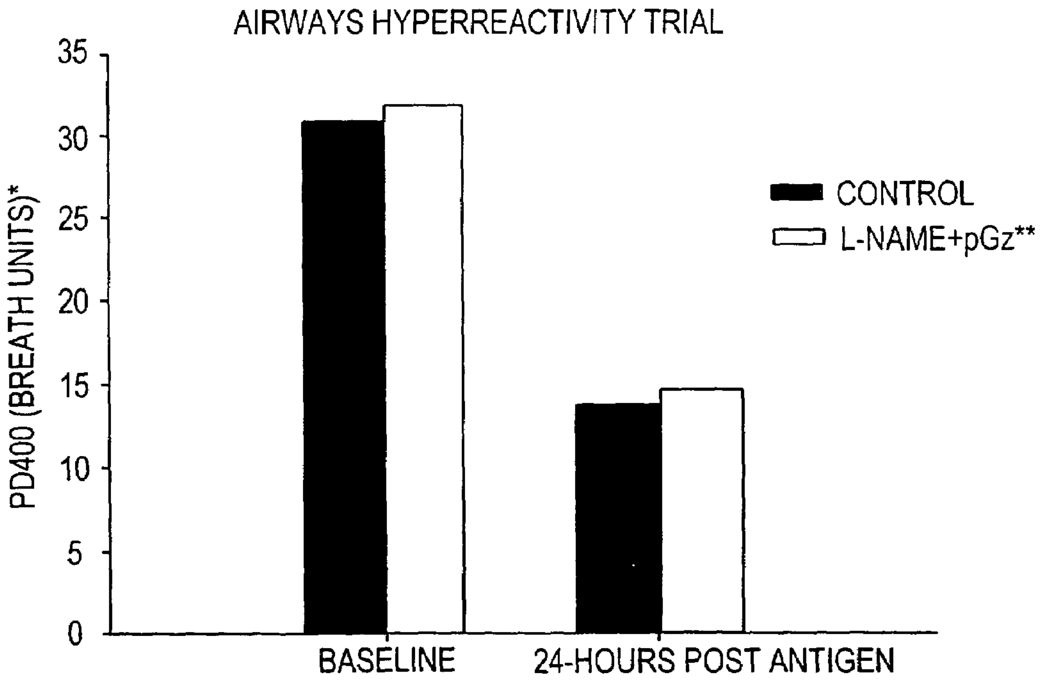

To demonstrate that the blunting of the immediate and late response were mediated through a nitric oxide pathway, L-NAME, an inhibitor of nitric oxide synthase activity, was administered prior to treatment with periodic acceleration. As seen in FIG. 23, this blocked the ameliorative action of periodic acceleration on the immediate and late response to antigen challenge. In this situation, periodic acceleration cannot release nitric oxide from eNOS. Since aerosolized nitroglycerin that releases nitric oxide and inhaled nitric oxide are weak bronchodilators (Gruetter C. A., Childers C. E., Bosserman M. K., Lemke S. M., Ball J. G., Valentovic M. A., *Comparison of relaxation induced by glyceryl trinitrate, isosorbide dinitrate, and sodium nitroprusside in bovine airways,* Am. Rev. Respir. Dis., 139:1192–97 (1989); Kacmarek R. M., Ripple R., Cockrill B. A., Bloch K. J., Zapol W. M., Johnson D. C., *Inhaled nitric oxide. A bronchodilator in mild asthmatics with methacholine-induced bronchospasm,* Am. J. Respir. Crit Care Med., 153:128–35 (1996)), this indicates that the action of nitric oxide as seen in FIG. 22, must have been indirect through its known suppression of the transcriptional gene, nuclear factor kappa beta that activates white blood cells and others to produce inflammatory cytokines.

Figure 24:
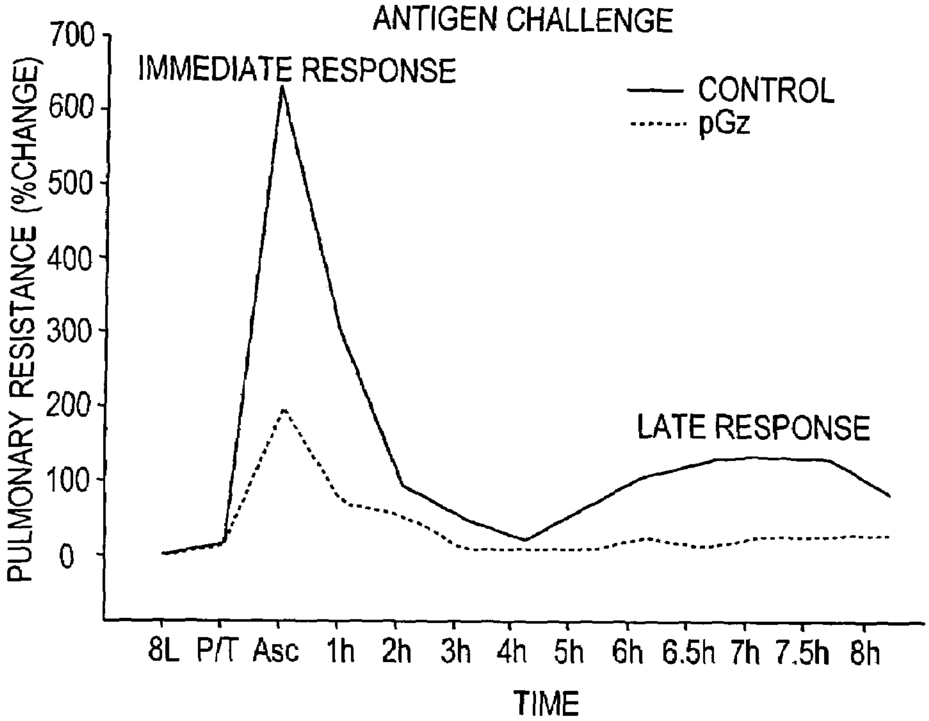
FIG. 24 shows two graphs demonstrating the effects of pretreating antigen challenged allergic sheep with periodic acceleration in one hour sessions over three days according to a preferred embodiment of the present invention.
Figure 24:
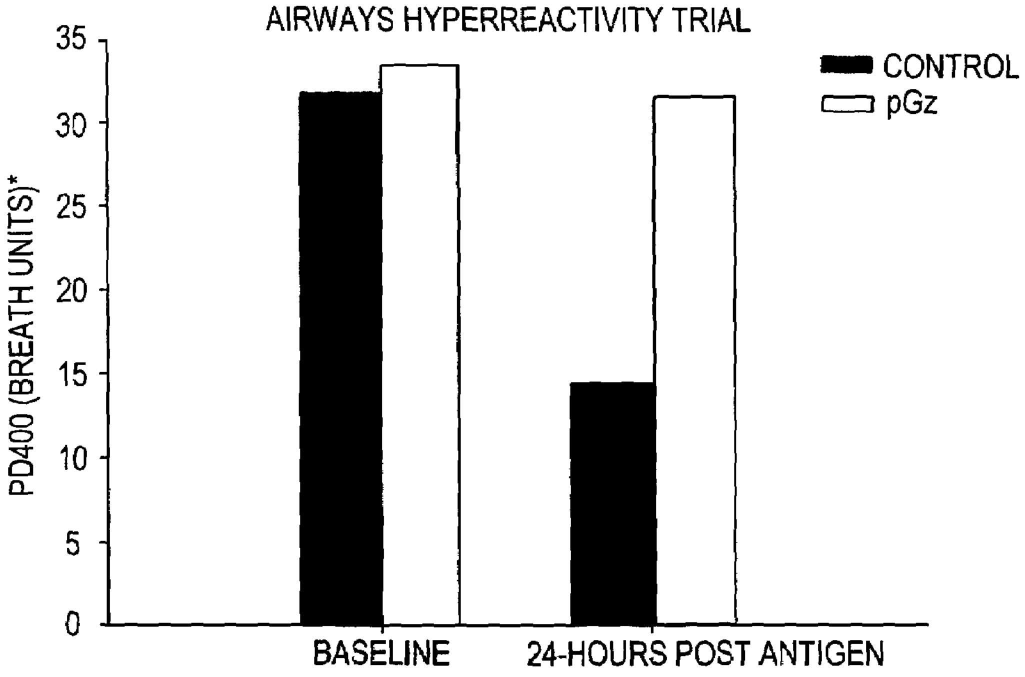

FIG. 24 shows the effects when an allergic sheep underwent a course of two, one-hour, periodic acceleration treatments a day for three days because treatment of asthmatic humans with corticosteroids is usually carried out over days rather than a single treatment. On the fourth day, a final periodic acceleration treatment was followed by antigen challenge. As seen in FIG. 24, there is even greater blunting of the immediate response compared to the single treatment in FIG. 22 and the late response is completely suppressed. The airways hyperreactivity tested with carbachol did not differ from the baseline control (without antigen challenge) in contrast to the results of a single periodic acceleration treatment depicted in FIG. 23 that showed hyperreactivity. This experiment indicates that there is a cumulative effect produced with periodic acceleration treatments that upregulates activity of eNOS. This effect is due to direct suppression of endothelin-1 by nitric oxide as well as an indirect effect of nitric oxide through suppression of nuclear factor kappa beta that inhibits production of endothelin-1 (Noguchi K., Ishikawa K., Yano M., Ahmed A., Cortes A., Abraham W. M., *Endothelin-*1 *contributes to antigen-induced airway hyperresponsiveness,* J. Appl. Physiol., 79:700–05 (1995); Ohkita M., Takaoka M., Shiota Y., Nojiri R., Matsumura Y., *Nitric oxide inhibits endothelin-*1 *production through the suppression of nuclear factor kappa B,* Clin. Sci. (Lond), 103 Suppl 48:68S–71S (2002)).

B. Preconditioning and/or Conditioning the Heart and Other Organs

Background

For almost two decades, it has been recognized that brief episodes of coronary occlusion (~15 minutes) followed by reperfusion does not result in myocardial necrosis. However, the contractile function and high-energy phosphate content of the previously ischemic myocardium remains depressed or "stunned" for several hours to days after reperfusion. Over the course of time, this situation may improve but chronic contractile abnormalities of the ischemic segment may persist as in chronic hibernation. The latter may be the result of repetitive stunning episodes that have a cumulative effect. Such episodes can cause protracted postischemic left ventricular dysfunction that often leads to chronic heart failure. Myocardial stunning occurs clinically in various situations in which the heart is exposed to transient ischemia, such as unstable angina, acute myocardial infarction with early reperfusion, ventricular fibrillation with DC countershock, exercise-induced ischemia, cardiac surgery, and cardiac transplantation (Kloner R. A., Jennings R. B., *Consequences of brief ischemia: stunning, preconditioning, and their clinical implications: part* 2, Circulation, 104: 3158–67 (2001)).

Prevention or mitigation of the extent of stunning can be accomplished by preconditioning the heart. It has long been recognized that brief periods (few minutes or less) of ischemia precondition the myocardium to subsequent longer ischemic challenges. The cardioprotective effects of preconditioning occur in two temporally distinct phases, an early phase that develops and wanes within 2 to 4 hours after the ischemic challenge, and, a second (or late) phase which begins after 12 to 24 hours and lasts for 3 to 4 days. Nitric oxide released from nitric oxide synthase (eNOS) in vascular endothelium is responsible for the early phase of precondioning and either nitric oxide generated from inducible nitric oxide synthase (iNOS) or eNOS are probably responsible for the late phase. Most investigators believe that nitric oxide released from eNOS in the early phase triggers the activation of iNOS in the late phase (Bell R. M., Smith C. C., Yellon D. M., *Nitric oxide as a mediator of delayed pharmacological* (*A*(1) *receptor triggered*) *preconditioning; is eNOS masquerading as iNOS?* Cardiovasc.Res., 53:405–13 (2002); Bolli R., *The late phase of preconditioning,* Circ. Res., 87:972–83 (2000)). Nitric oxide is the most important molecule in affording cardiac protection. Since periodic acceleration releases nitric oxide from nitric oxide synthase (eNOS), it can also serve as a means for preconditioning vital organs. The phenomenon of preconditioning also is operative in brain, kidneys, liver, stomach, intestines, and lungs (Pajdo R., Brzozowski T., Konturek P. C., Kwiecien S., Konturek S. J., Sliwowski Z. et al., *Ischemic preconditioning, the most effective gastroprotective intervention: involvement of prostaglandins, nitric oxide, adenosine and sensory nerves,* Eur. J. Pharmacol., 427: 263–76 (2001)).

In addition to myocardial ischemia, various nonpharmacologic and pharmacologic treatments have been shown to be effective in late phase preconditioning of the heart. These include heat stress, rapid ventricular pacing, exercise, endotoxin, cytokines, reactive oxygen species, nitric oxide donor drugs, adenosine receptor agonists, endotoxin derivatives, and opioid agonists. Most of these forms of late phase PC incitements protect against lethal ischemia/reperfusion injury (infarction) and at least some have been found to be protective against reversible postischemic dysfunction (stunning), arrhythmias, and endothelial dysfunction. None of the aforementioned techniques are practical as safe preventives in a clinical setting. Thus, Kloner & Jennings concluded that: "The future challenge is how to minimize the stunning phenomenon and maximize the preconditioning phenomenon in clinical practice." (Kloner R. A., Jennings R. B., *Consequences of brief ischemia: stunning, preconditioning, and their clinical implications: part* 2, Circulation, 104:3158–67 (2001)).

Use of Periodic Acceleration for Preconditioning and/or Conditioning

Although preconditioning is protective against ischemia in vital organs, its widespread application in most clinical situations is limited. For example, although preconditioning limits the extent of experimental stroke in animals, one cannot carry out preconditioning in patients in which a stroke is in progress since the event has already occurred. On the other hand, preconditioning prior to cardiopulmonary bypass surgery to prevent myocardial and brain ischemia can be accomplished because of the elective nature of this surgery. Since nitric oxide released from endothelial nitric oxide synthase (eNOS) appears to the agent most responsible for the protective effects of preconditioning, the treatment can be accomplished with periodic acceleration. Further, protection by upregulation of nitric oxide can be attained during the ischemic event, e.g., stroke, acute myocardial infarction, cardiopulmonary resuscitation, etc. Here, the modality can be designated "conditioning" rather than "preconditioning." In the recovery period after reperfusion has taken place, treatment with periodic acceleration can be termed, "postconditioning." Periodic acceleration accomplishes part of its beneficial effects by diminishing oxygen consumption of the ischemic organ through nitric oxide release from eNOS. The latter also suppresses the transcriptional gene, nuclear factor kappa beta, which diminishes the inflammatory response associated with ischemia by suppression of inflammatory cytokines, tumor necrosis factor alpha, adhesion molecules and activity of inducible nitric oxide synthase (iNOS).

C. As a Non-Invasive Ventilator and Cardiopulmonary Resuscitative Device

Background

Mechanical ventilators support respiration when the patient has cessation of breathing as in anesthesia, with narcotic and sedative overdoses, and with central nervous system injuries or infections. Mechanical ventilators are also used during episodes of respiratory muscle dysfunction and/or fatigue that occur in Adult Respiratory Distress Syndrome (ARDS), Severe Acute Respiratory Syndrome (SARS), meconium aspiration syndrome of the newborn, acute exacerbations of respiratory insufficiency associated with obstructive and restrictive lung diseases. Mechanical ventilators are often applied by facemask in patients with neuromuscular disease or chronic obstructive lung disease particularly during sleep, a situation associated with respiratory depression. However, mechanical ventilators that rely upon positive or negative pressures to inflate the lungs may produce serious adverse effects that include inflammation of pulmonary tissue mediated by activation of nuclear factor kappa beta and mechanical barotrauma or volutrauma causing pneumothorax. Long lasting consequences of the inflammatory process may lead to pulmonary fibrosis (Haddad J. J. *Science review: redox and oxygen-sensitive transcription factors in the regulation of oxidant-mediated lung injury: role for hypoxia-inducible factor-*1*alpha,* Crit Care 7:47–54 (2003); Parker J. C., Hernandez L. A., Peevy K. J., *Mechanisms of ventilator-induced lung injury,* Crit Care Med., 21:131–43 (1993)). A means for supporting ventilation by more natural means, i.e., without resorting to positive or negative pressure mechanical ventilators is clearly needed.

In previous work, such as the '976 patent, ventilation assistance for humans was based upon investigations in anesthetized, paralyzed piglets. In these animals, ventilation was fully supported with periodic acceleration despite paradoxical movement between the rib cage and abdomen. Since the piglet respiratory system has mechanical properties similar to human newborns, it was thought periodic acceleration would serve as an effective non-invasive ventilator in that patient group. Although this is true (especially of newborns), the prior art methods as disclosed in the '976 patent did not sufficiently factor in the fact that the adult respiratory system differs from the newborn in that the rib cage is much stiffer. Periodic acceleration produces less than 75 ml of tidal volume in relaxed normal, supine humans at rates up to about 180 per minute with ±0.4 g, a finding consistent with prior investigations in seated normal humans in which maximum tidal volumes of about 50 ml were found at a rate of 300 per minute (Zechman F. W. J., Peck D., Luce E., *Effect of vertical vibration on respiratory airflow and transpulmonary pressure,* J. Appl. Physiol., 20:849–54 (1965)). In seated subjects, there is also paradoxical movement between the rib cage and abdomen that limits breath volumes at the airway attainable with periodic acceleration.

In order to utilize periodic acceleration as a means of non-invasive ventilation, breath volumes (aka tidal volumes) must exceed the subject's pulmonary dead space, the volume of the conducting airways (trachea, bronchi, etc.) in which no exchange of oxygen and carbon dioxide takes place so that normal gas exchange can occur in the distal pulmonary alveoli. Dead space volume is approximately 1 ml per pound of body weight. The breathing pattern in supine, healthy subjects who are not breathing through a mouthpiece consists of respiratory rate 16.6 breaths/minute with range of 11–22 breaths per minute, tidal volume 383 ml with range of 201–565 ml and ventilation (rate times tidal volume) of 6.01 liters with range of 3.32–9.33 liters (Tobin M. J., Chadha T. S., Jenouri G., Birch S. J., Gazeroglu H. B., Sackner M. A., *Breathing patterns.* 1. *Normal subjects,* Chest, 84:202–05 (1983)). Therefore, ventilatory support with periodic acceleration requires production of tidal volume that at least exceeds the dead space volume, ~200 ml and is capable of producing greater than the upper limit of ventilation, ~10 liters per minute. In order to achieve this situation, the rib cage and abdomen must move in phase or nearly in phase during periodic acceleration in the same way as natural breathing. Our attempts to strap the abdomen, rib cage or both as well as application of continuous positive airway pressure (CPAP) in conscious adults failed to halt paradoxical movements between the rib cage and abdomen during periodic acceleration. It should be noted that external, high frequency chest wall oscillations with a VEST system over the torso produce only about 100 ml volume per breath (Khoo M. C., Gelmont D., Howell S., Johnson R., Yang F., Chang H. K., *Effects of high-frequency chest wall oscillation on respiratory control in humans,* Am. Rev. Respir. Dis., 139:1223–30 (1989)).

Use of Periodic Acceleration as Non-Invasive Ventilator and/or Cardiopulmonary Resuscitative Device The preferred embodiment of the apparatus according to the present invention is the preferred means to produce synchronous movements between the rib cage and abdomen during periodic acceleration to achieve ventilatory support comparable to that produced with positive or negative pressure mechanical ventilators. It is also a means to make periodic acceleration an aid to the removal of retained bronchopulmonary secretions. The latter occur in mechanical ventilator dependent patients, in cystic fibrosis, bronchiectasis, chronic bronchitis, bronchial asthma, kyphoscoliosis, Parkinson's disease, and with aspiration into the lungs of gastric contents.

Figure 25:
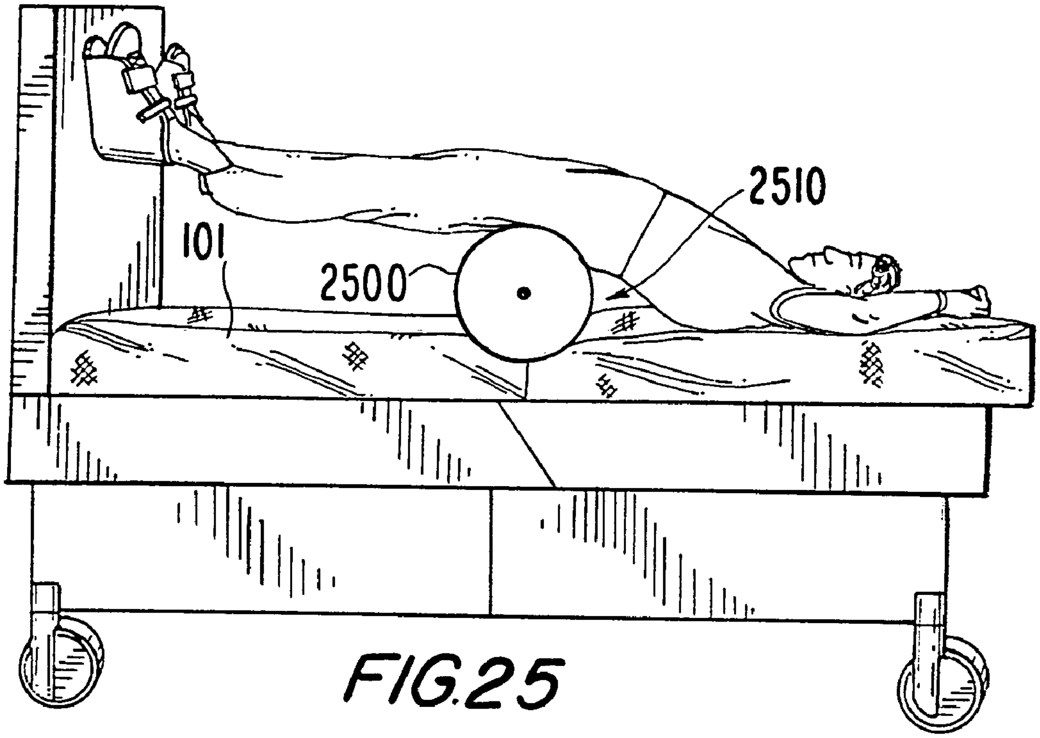
FIG. 25 is a picture showing a subject on a motion platform with a 12" diameter bolster placed under the subject's buttocks according to a preferred embodiment of the present invention.
Figure 26:
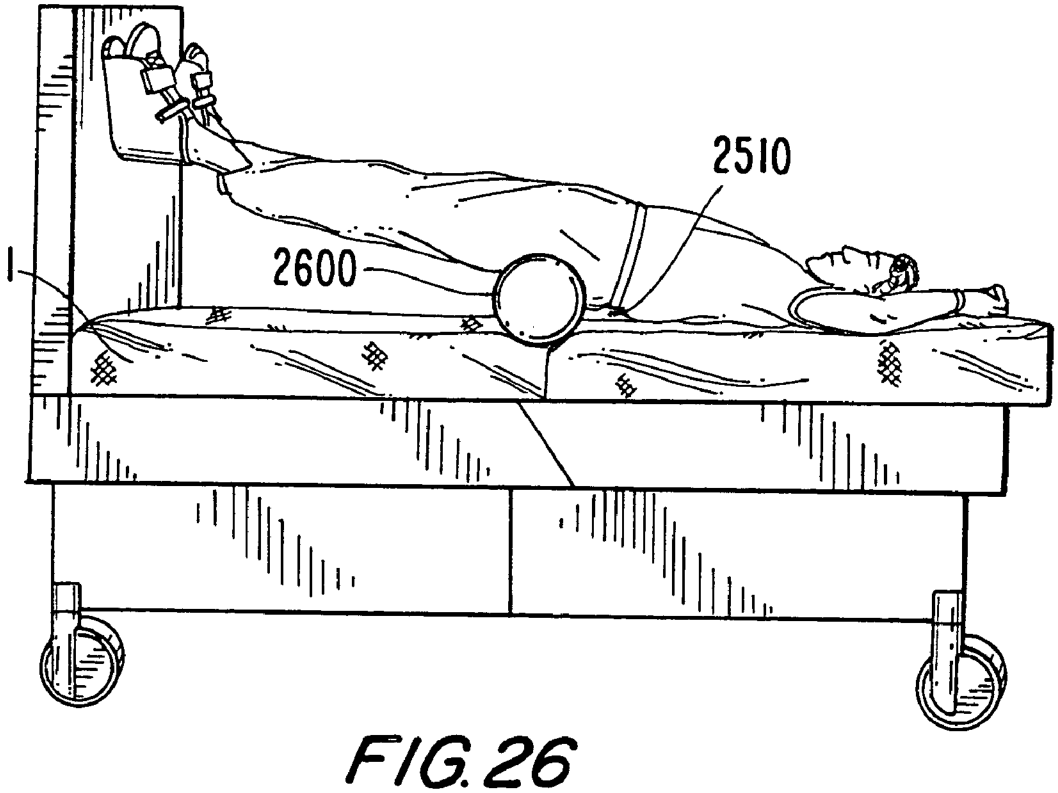
FIG. 26 is a picture showing a subject on a motion platform with a 8" diameter bolster placed under the subject's buttocks according to a preferred embodiment of the present invention.

In a relaxed, conscious subject with an opened glottis, synchronous movement between the rib cage and abdomen takes place during periodic acceleration if a bolster is placed under the buttocks such that the lower back of the supine subject is lifted off the mattress 101 of the motion platform with the upper back remaining on the mattress 101 (as shown in FIGS. 25–26). FIG. 25 depicts the placement of a 12" diameter bolster 2500 under the buttocks to lift the lower back off the AT 101 (the motion platform) mattress 101. This amount of lift is generally not needed but is depicted here to clearly demonstrate that the lower back is off the mattress 101, as shown at 2510. FIG. 26 depicts the placement of a 8" diameter bolster 2600 under the buttocks to lift the lower back off the AT 101 (motion platform) mattress 101.

Figure 27:
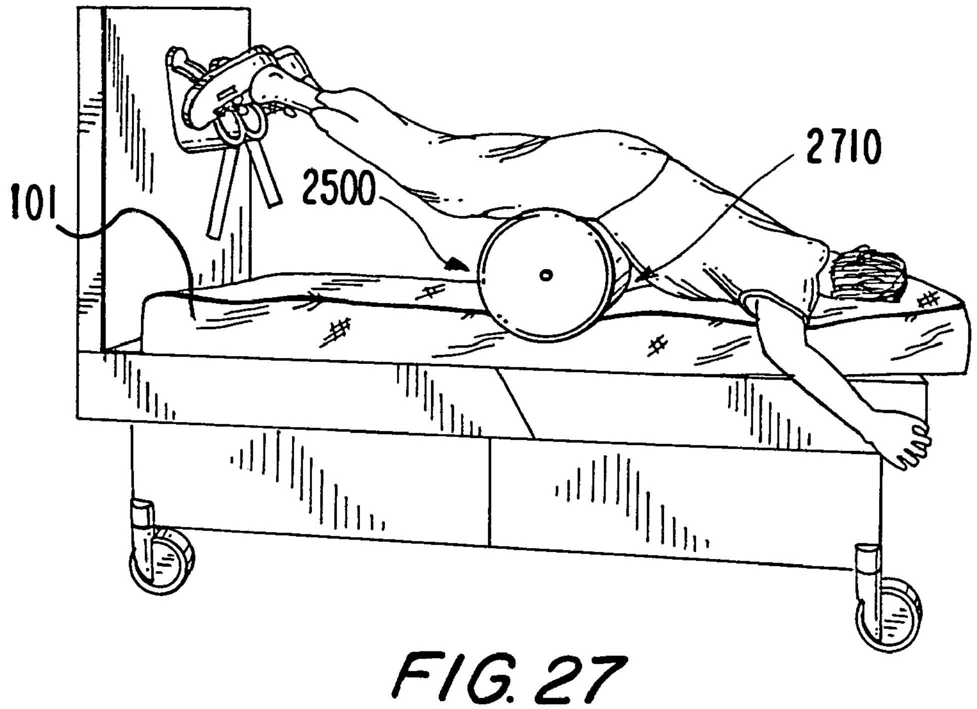
FIG. 27 is a picture showing a subject on a motion platform with a 12" diameter bolster placed under the subject's pubic area according to a preferred embodiment of the present invention.
Figure 28:
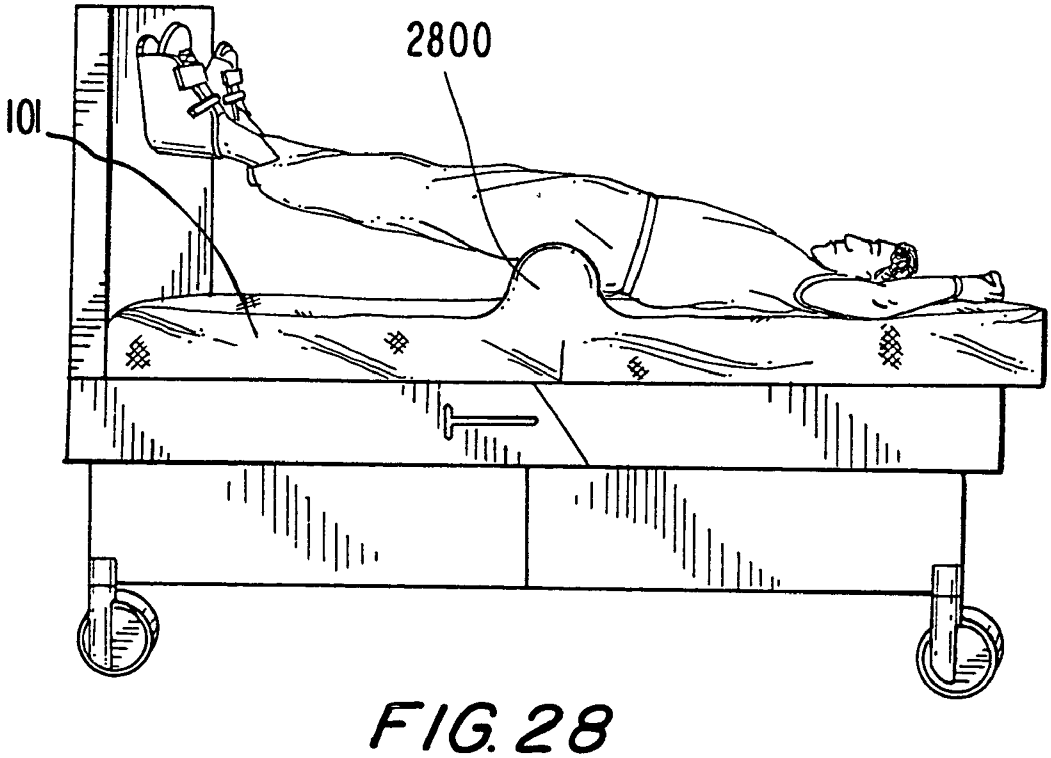
FIG. 28 is a drawing showing an adjustable bolster in a motion platform according to a preferred embodiment of the present invention.

In the prone posture, the same phenomenon takes place if bolster is placed under the pubic region in order to lift the abdomen off the mattress 101 (as shown in FIG. 27). FIG. 27 depicts the placement of a 12" diameter bolster 2500 under the buttocks to lift the abdomen off the AT 101 mattress 101 in the prone subject. This amount of lift is generally not needed but is depicted here to clearly demonstrate that the abdomen is off the mattress 101, as shown at 2710. The lifting of the body can also be accomplished with a sling from a crane or by mechanically raising a bolster-like object incorporated into the mattress assembly through an opening into the surface of the motion platform that supports the mattress 101. FIG. 28 depicts a bolster 2800 that can be raised or lowered from an opening in the surface of the plate that supports the mattress 101 of the AT 101 (motion platform) to achieve variable lift to the buttocks in the supine posture and the abdomen in the prone posture.

Figure 29:
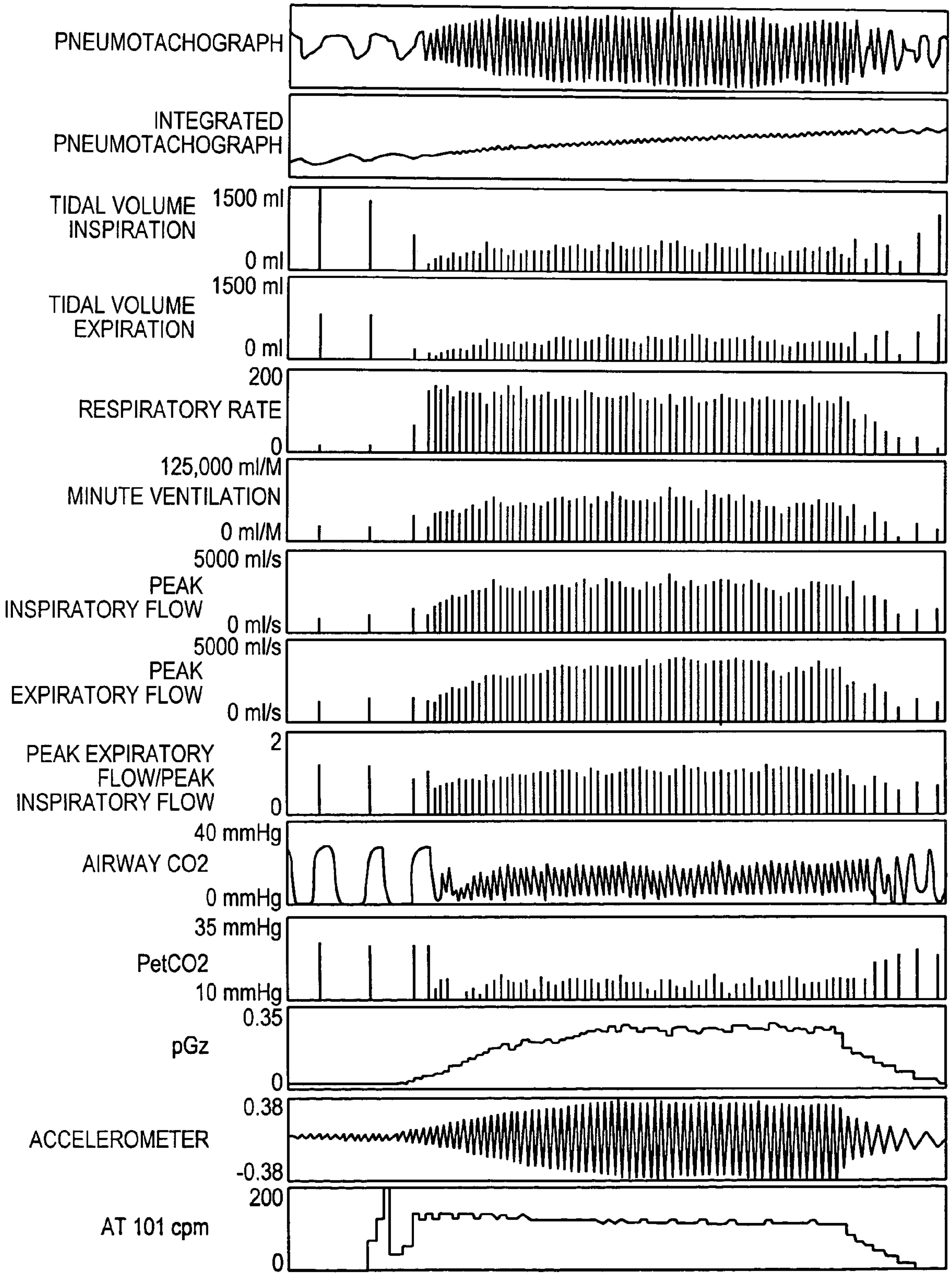
FIG. 29 is a graph showing the effects of non-invasive motion ventilation performed on an adult holding his glottis open according to a preferred embodiment of the present invention

In both the supine and prone postures, extremely efficient ventilatory support is achieved with periodic acceleration because the rib cage and the abdomen move synchronously with the bolster elevations of the mid-portion of the body. In the example recording shown in FIG. 29, the subject relaxed his respiratory muscles and held his glottis opened. Periodic acceleration was applied at ±0.25 g with the motion platform (AT 101) operating at about 150 cpm. A small bolster (6" diameter) was placed under the buttocks. This figure depicts a mean respiratory rate of 138 breaths/minute, tidal volume of 490 ml, and minute ventilation of 66 liters as well as low mean end-tidal carbon dioxide tensions (PetCO2) of 16 mmHg (normal 35–40 mm Hg). This indicates that non-invasive motion ventilation with a bolster under the buttocks has the capability of functioning as a non-invasive ventilator in adults. Non-invasive motion ventilation has sufficient capabilities to even hyperventilate as indicated by the very low values of end-tidal carbon dioxide tension, a measure of alveolar ventilation in this example. These low values could be a slight overestimate because of delay in response time of the carbon dioxide analyzer at the high respiratory rate of 138 breaths/minute. However, in the natural breath at a rate of 28 per minute immediately after halting periodic acceleration, end-tidal carbon dioxide tension was still very low at 23 mmHg (normal values 35 to 40 Hg).

Figure 30:
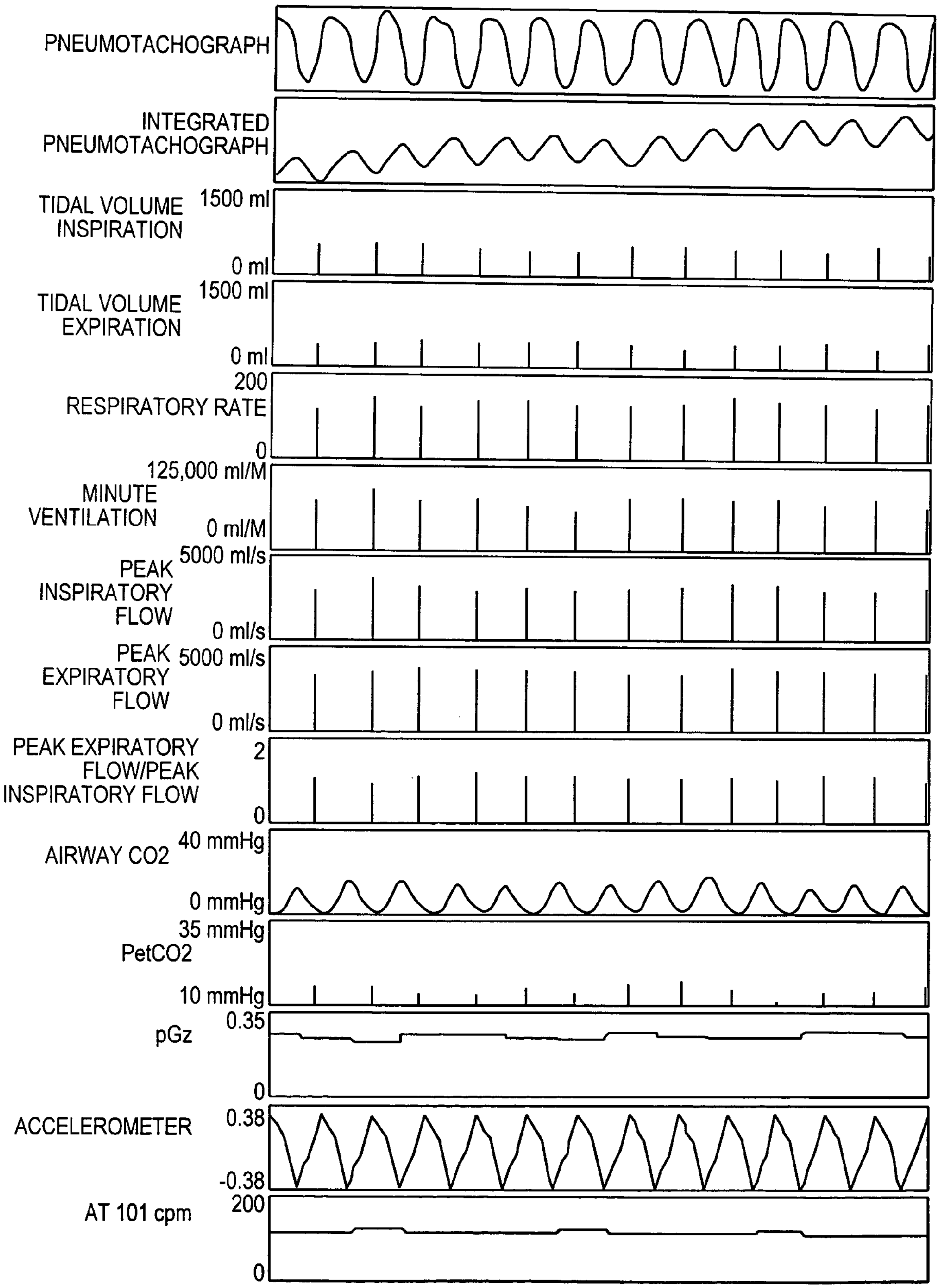
FIG. 30 is a closeup of a portion of FIG. 29 demonstrating the relationship between the acceleration of the motion platform and the airflow of the subject during treatment according to a preferred embodiment of the present invention.
Figure 31:
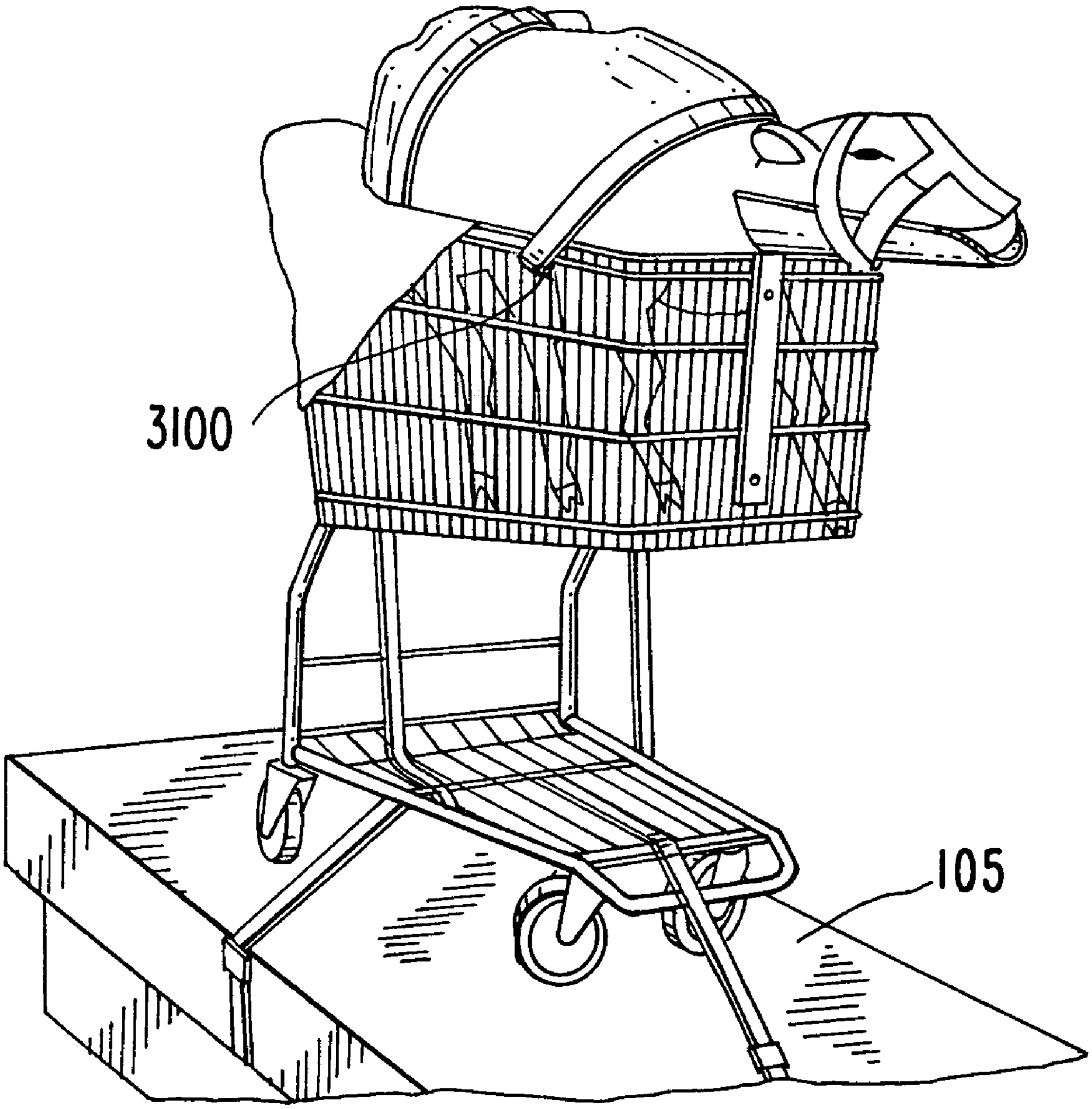
FIG. 31 is a picture of a sheep restrained on a motion platform according to an embodiment of the present invention.

As seen in FIG. 30, the accelerometer trace from the motion platform (AT 101) and the pneumotachograph airflow from the subject are nearly in-phase with minimal volume variability indicating that the respiratory system is being driven by the motion platform rather than by the subject responding to cues from the motion of the device. In conscious, nasal-tracheal intubated, standing sheep, restrained in a cart on the motion platform such that the rib cage was supported with a sling (shown in FIG. 31), the rib cage and abdomen moved in phase with periodic acceleration. FIG. 31 shows a sheep restrained in a cart placed upon the surface of the motion platform. The sling 3100 is attached to the rails of the cart. Low end-tidal carbon dioxide tensions were found that ranged between 10 and 20 mm Hg during application of periodic acceleration of 120 cpm and ±0.15 g. This observation further demonstrates that periodic acceleration with the rib cage supported and the abdomen free serves as an efficient means of ventilatory support.

Figure 32:
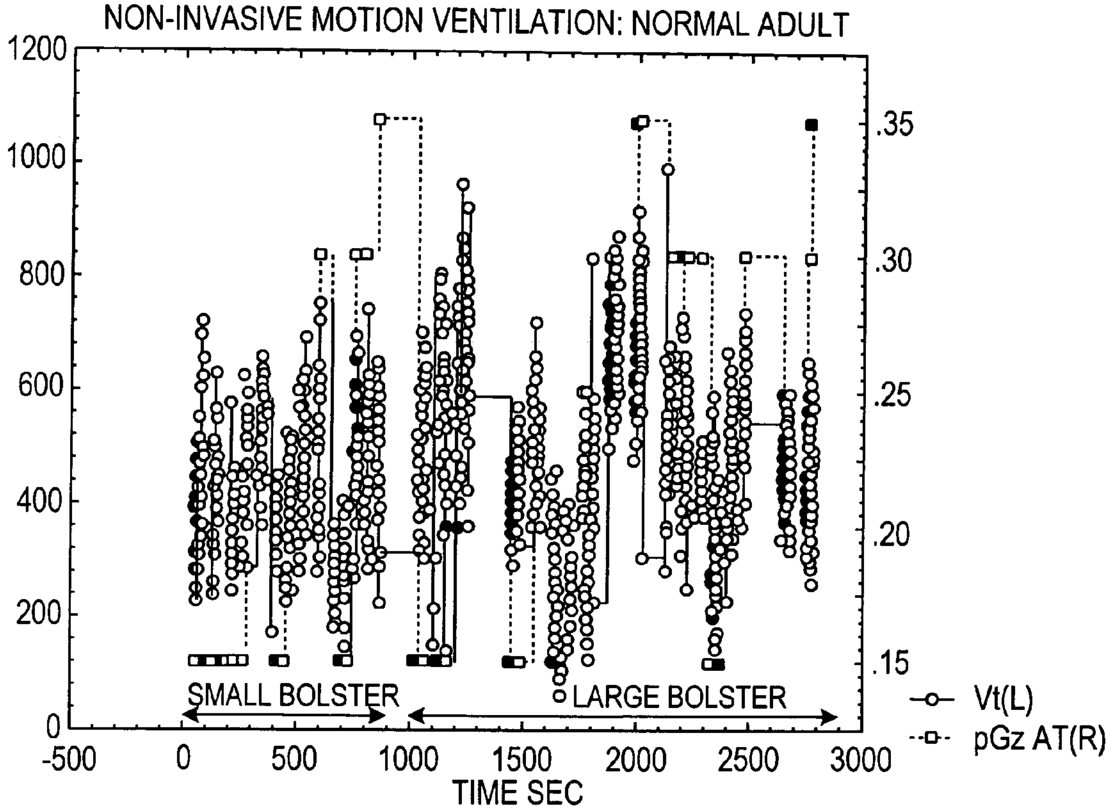
FIG. 32 shows two graphs demonstrating the effects on tidal volume and peak flow of a subject with either an 8" or a 12" bolster placed under the subject by periodic acceleration according to a preferred embodiment of the present invention.
Figure 32:
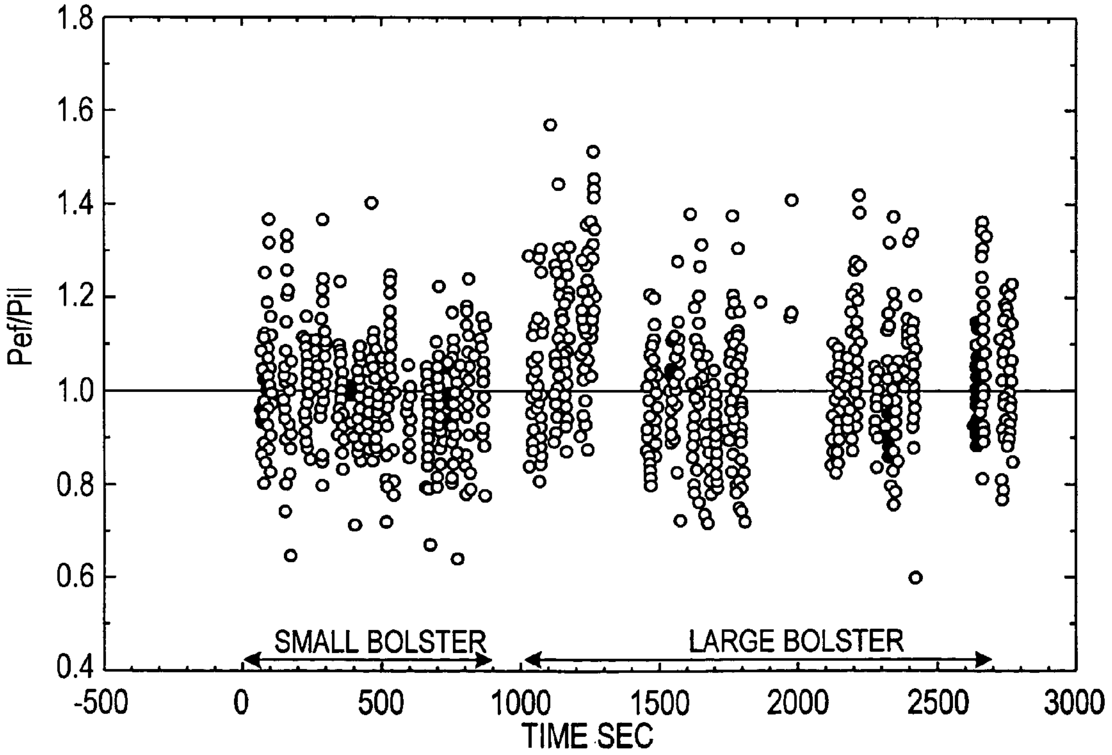

In general, tidal volumes produced with periodic acceleration were slightly greater with the large than the small bolster. Rates of approximately 120 cpm gave the highest mean value of tidal volume of 525 ml whereas pGz of 0.35 gave the highest mean value of tidal volume of 601 ml in this example (FIG. 32). In FIG. 32, the upper panel depicts values for tidal volume and pGz in a single subject lying supine with either a small (6" diameter) or large (8" diameter) bolster placed under the buttocks. The motion platform (AT 101) was set at approximately 90, 120, 150, and 180 cycles per minute. Periodic acceleration was varied from ±0.15 g, 0.20, 0.25. 0.30, and 0.35 over these frequencies. The lower panel shows that the ratio of peak expiratory flow to peak inspiratory is unity at any given cpm and pGz produced with the motion platform.

Figure 33:
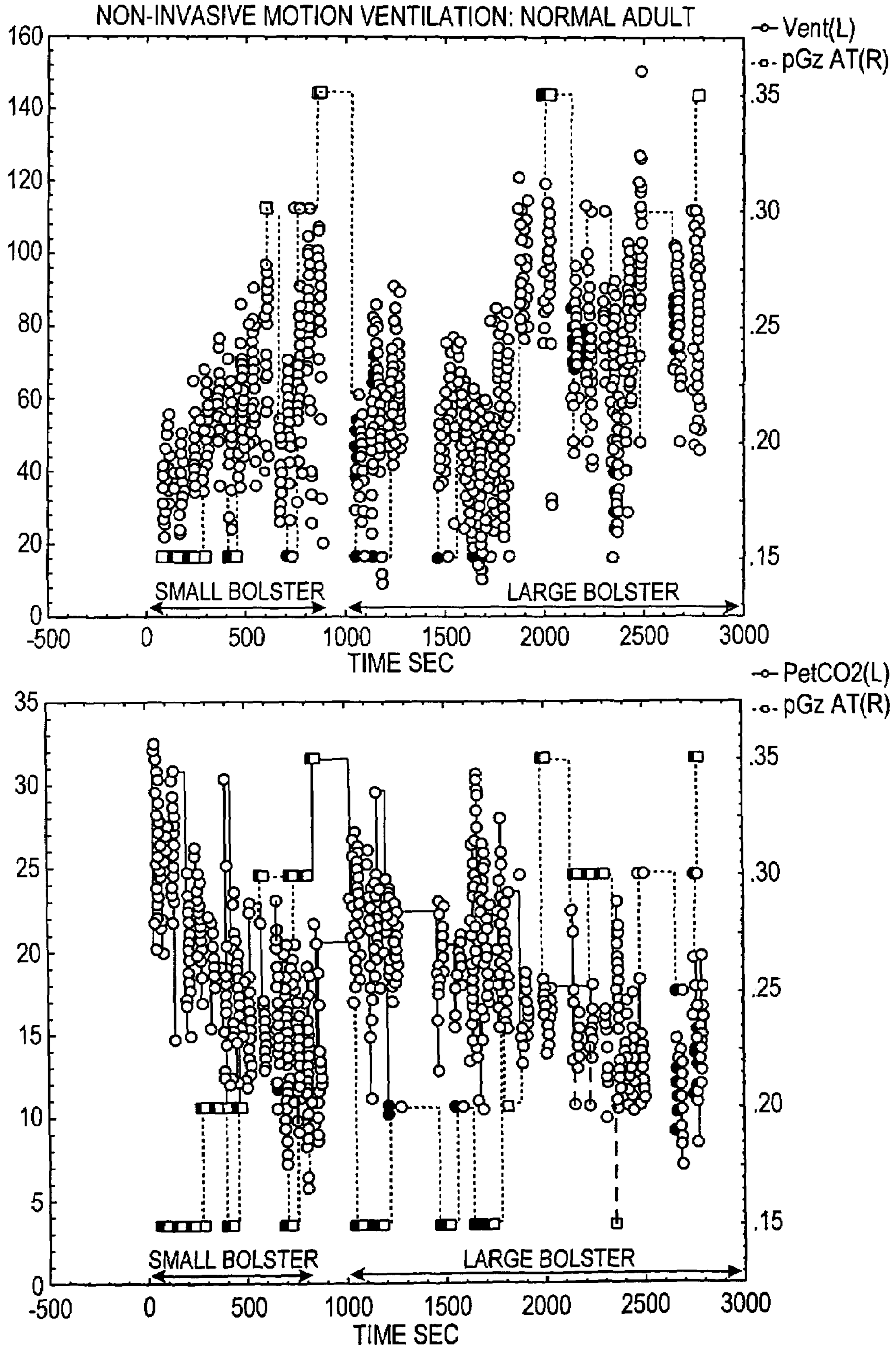
FIG. 33 shows two graphs demonstrating the effects on motion ventilation and end-tidal carbon dioxide tension of a subject with either an 8" or a 12" bolster placed under the subject by periodic acceleration according to a preferred embodiment of the present invention.

These values are more than adequate to achieve ventilatory support at the high respiratory rates attained in this study as demonstrated for the values of minute ventilation and end-tidal carbon dioxide tension depicted in FIG. 33. The upper panel in FIG. 33 depicts values for minute ventilation and pGz in a single subject lying supine with either a small (6" diameter) or large (8" diameter) bolster placed under the buttocks. The motion platform (AT 101) was set at approximately 90, 120, 150, and 180 cycles per minute. Periodic acceleration was varied from ±0.15 g, 0.20, 0.25. 0.30, and 0.35 over these frequencies. In general, ventilation produced with periodic acceleration was slightly greater with the large than the small bolster. The highest minute ventilation of 90 liters was obtained with pGz of approximately ±0.35 with the large bolster and 81 liters with the small bolster. End-tidal carbon dioxide tension was low at all levels, more so at the greater pGz levels. Finally, the beneficial mediator release of nitric oxide into the circulation from eNOS to suppress inflammatory processes into the circulation also occurs during the employment of periodic acceleration with bolster support of the mid-body.

In non-intubated humans, ventilatory support produced with periodic acceleration and bolster support under the buttocks in the supine posture and pubic region in the prone posture can be overcome by voluntary contraction of the respiratory muscles. Thus, periodic acceleration as a means of non-invasive ventilatory is indicated in intubated, sedated, ventilatory-dependent, or apneic subjects. Periodic acceleration with bolster support can also substitute for conventional, facemask or nasal applied positive or negative pressure mechanical ventilators in patients with neuromuscular or chronic respiratory diseases during sleep. Periodic acceleration can also supplement ventilation produced with standard mechanical ventilators. In the current design of the invention, the distance that the platform moves limits the lowest rate of periodic acceleration to about 90 cpm with ±0.15 g. When gravitional forces fall below this value, ventilation is difficult to achieve at lower rates. Therefore, for ventilatory applications at lower cpm, the platform displacement will be increased by increasing the radius of the driving fly wheels and/or using a more powerful motor.

In addition to the ventilatory aspects of this invention, periodic acceleration with placement o bolsters under the buttocks in the supine and under the pubic region in the prone posture aids in removal of retained bronchopulmonary secretions. This is because periodic acceleration produces high peak flow rates in both inspiration and expiration with their ratio near unity. Since airways are smaller in expiration than inspiration, air velocity in expiration is higher in expiration than inspiration even though flow rates are equivalent. The flow rates increased as a function of both cpm of the motion platform and the magnitude of pGz. The highest peak expiratory flow was obtained at pGz of ±0.35 g, e.g., 6 liters/second (normal resting peak flow about 0.5 liters/per second). Since two phase gas-liquid interaction moves secretions as a function of air velocity across the secretions and in a direction of the higher velocity phase, expiration as opposed to inspiration, bronchopulmonary secretions will move upward from the airways into the oral cavity to be expectorated or removed with suction catheters (Benjamin R. G., Chapman G. A., Kim C. S., Sackner M. A., *Removal of bronchial secretions by two-phase gas-liquid transport,* Chest, 95:658–63 (1989); Kim C. S., Iglesias A. J., Sackner M. A., *Mucus clearance by two-phase gas-liquid flow mechanism: asymmetric periodic flow model,* J. Appl. Physiol., 62:959–71 (1987)). The postural changes needed to achieve ventilation with the placement of bolsters or the built in rise bolster-like object incorporated within the motion platform (AT 101) also promote postural drainage that further facilitate removal of bronchopulmonary secretions (FIGS. C–F).

D. Preconditioning and/or Treatment of Animals

Background

Animals are subject to medical maladies which can have a great economic impact. As an instructive example, horses are susceptible to specific diseases or conditions that may be life-threatening or render the animal incapable of continuing a racing career. The economic impact of all horse activities as estimated by the American Horse Council was $112 billion (The Economic Impact of the Horse Industry in the United States, 1997). Services provided by racing, showing, and recreation provided over 25% each. The illnesses that commonly occur in horses include fractures of an extremity, osteoarthritis, colic, exercise-induced pulmonary hemorrhage, heaves, and chronic obstructive lung disease.

Compound leg fractures in horses during a race or training session are usually fatal because of problems with infection, immobilization and healing and are the commonest cause of death in a racing horse (Johnson B. J., Stover S. M., Daft B. M., Kinde H., Read D. H., Barr B. C. et al., *Causes of death in racehorses over a* 2 year period, Equine Vet. J., 26:327–30 (1994)). Stress fractures and non-displaced fractures of bones can be handled with techniques that have been used in treatment of human fractures but nonunion of fractures remains a problem (McClure S. R., Watkins J. P., Glickman N. W., Hawkins J. F., Glickman L. T., *Complete fractures of the third metacarpal or metatarsal bone in horses:* 25 *cases* (1980–1996), J. Am. Vet. Med. Assoc., 213:847–50 (1998); Winberg F. G., Pettersson H., *Outcome and racing performance after internal fixation of third and central tarsal bone slab fractures in horses. A review of* 20 cases, Acta Vet.Scand., 40:173–80 (1999)).

Osteoarthritis occurs naturally in horses. There are high concentrations of tumor necrosis factior alpha and metalloproteinases in the joint fluid (Jouglin M., Robert C., Valette J. P., Gavard F., Quintin-Colonna F., Denoix J. M., *Metalloproteinases and tumor necrosis factor-alpha activities in synovial fluids of horses: correlation with articular cartilage alterations,* Vet. Res., 31:507–15 (2002)). There are high concentrations of IL-1 and metalloproteinases in joint fluid. Although phenylbutazone, flunixin, betamethasone, dexamethasone, methylprednisolone acetate (MPA), hyaluronan, pentosan polysulphate and polysulphated glycosaminoglycan inhibit equine metalloproteinases, these effects are only obtained at concentrations which are unlikely to be achieved for any length of time in vivo (Clegg P. D., Jones M. D., Carter S. D., *The effect of drugs commonly used in the treatment of equine articular disorders on the activity of equine matrix metalloproteinase-*2 *and* 9, J. Vet. Pharmacol. Ther., 21:406–13 (1998)). Therefore, treatment of osteoarthritis mainly involves resting the horse along with anti-inflammatory drugs.

Colic in horses is a major risk to health that means only pain in the abdomen. There are many causes for such pain, ranging from the mild and inconsequential to life threatening or fatal. In its early stages, equine colic can be very difficult to distinguish the mild from the potentially fatal such that all cases of abdominal pain should be taken seriously right from their onset. The anatomy of the gastrointestinal horse offers an explanation as to why colic is common and potentially serious. At the junction of the small and large intestines, there is a large blind-ended outpouching over 1 m long with a capacity of 25–30 liters. This is the cecum (the horse's version of the human appendix). Food passes from a relatively small stomach to the small intestine into the cecum before passing into the large intestine. Together, the cecum and large intestine form the horse's "fermentation chamber", allowing it to gain nutritional support from the complex carbohydrates contained in grasses and other forage. The large intestine is 3 to 4 meters long with a diameter of 20–25 cm along most of its length and a capacity of over 50 liters; it fills a significant part of the abdomen. This large unwieldy structure is tethered to the body wall at only two points: at its beginning (where it joins the small intestine and cecum) and at its end (where it joins the short, narrow small colon which leads to the anus). With only two immobile points, the large intestine lies in the abdomen in a double-U formation, one "U" stacked on top of the other. This arrangement entails the food taking a circuitous route round a number of 180° bends (flexures) in the intestine.

There are several types of colic that occur in horses. Impaction colic occurs when the large intestine at one of its flexures becomes blocked by a firm mass of food. When gas builds up in the large intestine and/or cecum, it stretches the intestine causing gas colic. Spastic colic is due to increased intestinal contractions, the abnormal spasms causing the intestines to contract painfully. Displacement signifies that a portion of the intestine has moved to an abnormal position in the abdomen. A volvulus or torsion occurs when a piece of the intestine twists. The suspension of the small intestine from the mesentery (the "net curtain") and the unfixed nature of much of the large intestine predispose horses to intestinal displacements and torsions. Some cases of abdominal pain are due to inflammation of the small (enteritis) or large (colitis) intestines. When a horse gorges itself on grain or, even more seriously, a substance which expands when dampened like dried beet pulp, the contents of the stomach can swell. The horse's small stomach and its inability to vomit mean that in these circumstances the stomach may rupture. But in many cases of colic, it is impossible to determine the reason for the pain.

Thoroughbreds are more prone to colic than Arabian horses (Tinker M. K., White N. A., Lessard P., Thatcher C. D., Pelzer K. D., Davis B. et al., *Prospective study of equine colic incidence and mortality,* Equine Vet. J., 29:448–53 (1997)). Causes of colic in 229 racing horses included: gastric rupture (6); ileal impaction (17); small intestinal strangulating obstruction (22); proximal enteritis (16); transient small intestinal distension (18); large colon displacement (52); large colon impaction (34); colitis (8); small colon obstruction (7); peritonitis (7); and unknown (42). There was no correlation between use, amount of grain or hay fed, type of pasture, deworming or history of previous colic and various causes for colic (Morris D. D., Moore J. N., Ward S., *Comparison of age, sex, breed, history and management in* 229 horses with colic, Equine Vet. J. Suppl., 129–32 (1989)).

Since colic is a stress to the body, all causes are associated with an inflammatory response, e.g., blood and peritoneal fluid supernatant tumor necrosis factor alpha and IL-6 are greater in horses with colic, compared with healthy horses (Barton M. H., Collatos C., *Tumor necrosis factor and interleukin-*6 *activity and endotoxin concentration in peritoneal fluid and blood of horses with acute abdominal disease,* J. Vet. Intern. Med., 13:457–64 (1999)).

Exercise induced pulmonary hemorrhage (EIPH) is a major health concern and cause of poor performance in racing horses. It occurs primarily in Quarter Horses, Standardbreds, and Thoroughbreds worldwide during sprint racing but it is found in several other high performance non-racing activities. EIPH is of great concern to the racing industry because of financial implications resulting from decreased performance, lost training days, necessity for prerace medication, and banning of horses from racing. EIPH is characterized by pulmonary hypertension, edema in the gas exchange region of the lung, rupture of the pulmonary capillaries, intra-alveolar hemorrhage and the presence of blood in the airways. Numerous causes and pathophysiologic mechanisms have been proposed for EIPH, including small airway disease, upper airway obstruction, exercise-induced hyperviscosity, mechanical stresses of respiration and locomotion, redistribution of blood flow in the lung, alveolar pressure fluctuations, and pulmonary hypertension. Several factors may actually cause the pulmonary system to become heavily stressed to the point where capillaries fail leading to leakage of blood into the lungs. The severe pulmonary hypertension during racing seems to be the most likely primary cause of the bleeding but other factors as mentioned above may play a contributing role. The incidence of EIPH is greater in shorter, higher intensity events that are expected to generate higher pulmonary arterial pressures.

Many pharmacological and management interventions have been tried, but few have proven efficacy in treating EIPH. These include dehydration, furosemide and other diuretics, anti-hypertensive agents or pulmonary vasodilators such and nitroglycerin and inhaled nitric oxide to dilate the pulmonary vasculature, bronchodilators, pentoxifylline and other drugs to decrease blood viscosity, surgical correction of laryngeal hemiplegia to decrease upper airway resistance, nasal dilator strips to reduce the resistance and maintain full patency of the nasal passages, anti-inflammatory drugs to reduce lower airway inflammation, drugs to inhibit platelet aggregation, hesperidin-citrus bioflavinoids to alter capillary fragility, aminocaproic acid and transhexamic acid to inhibit fibrinolysis, herbal remedies, and estrogens (Kindig C. A., McDonough P., Finley M. R., Behnke B. J., Richardson T. E., Marlin D. J. et al.. *NO inhalation reduces pulmonary arterial pressure but not hemorrhage in maximally exercising horses.,* J. Appl. Physiol., 91:2674–78 (2001); Manohar M., Goetz T. E., Hassan A. S., *Effect of prior high-intensity exercise on exercise-induced arterial hypoxemia in Thoroughbred horses,* J. Appl. Physiol., 90:2371–77 (2001); Manohar M., Goetz T. E., *Pulmonary vascular pressures of strenuously exercising Thoroughbreds during intravenous infusion of nitroglycerin,* Am. J. Vet. Res., 60:1436–40 (1999); Newton J. R., Wood J. L., *Evidence of an association between inflammatory airway disease and EIPH in young Thoroughbreds during training,* Equine Vet. J. Suppl., 417–24 (2002); O'Callaghan M. W., Pascoe J. R., Tyler W. S., Mason D. K.. *Exercise-induced pulmonary haemorrhage in the horse: results of a detailed clinical, post mortem and imaging study. VIII. Conclusions and implications,* Equine Vet. J., 19:428–34 (1987); West J. B., Mathieu-Costello O., *Stress failure of pulmonary capillaries as a mechanism for exercise induced pulmonary haemorrhage in the horse,* Equine Vet. J., 26:441–47 (1994)).

The "heaves" signifies a respiratory disease in horses that is analogous to human bronchial asthma. It most common in horses older than six years. Recurrent bouts lead to pathologic findings consistent with pulmonary emphysema. It is currently treated with inhaled or intravenous corticosteroids and aerosolized bronchodilators. In one study, small amounts of nuclear factor kappa beta were present in bronchial cells of healthy horses, whereas high levels were found during acute airway obstruction in all heaves-affected horses. Three weeks after the crisis, the level of nuclear factor kappa beta found in bronchial cells of heaves-affected horses was highly correlated to the degree of residual lung dysfunction (Bureau F., Bonizzi G., Kirschvink N., Delhalle S., Desmecht D., Merville M. P. et al., *Correlation between nuclear factor-kappaB activity in bronchial brushing samples and lung dysfunction in an animal model of asthma,* Am. J. Respir. Crit Care Med., 161:1314–21 (2000); Giguere S., Viel L., Lee E., MacKay R. J., Hernandez J., Franchini M., *Cytokine induction in pulmonary airways of horses with heaves and effect of therapy with inhaled fluticasone propionate,* Vet. Immunol. Immunopathol., 85:147–58 (2002); Peroni D. L., Stanley S., Kollias-Baker C., Robinson N. E., *Prednisone per os is likely to have limited efficacy in horses.* Equine Vet. J., 34:283–87 (2002)).

Use of Periodic Acceleration for Treatment and/or Prevention in Animals, such as Horses The preferred embodiment of the apparatus according to the present invention can be used to address the treatment and prevention of several serious diseases of horses. Treatment and prevention hinges on release of nitric oxide from endothelial nitric oxide synthase owing to the addition of pulses to the circulation produced with periodic acceleration. This in turn produces preconditioning as well as suppression of nuclear factor kappa beta. The latter action in turn prevents release of inflammatory cytokines (IL-1 beta, IL-2, IL-6, IL-8, and IL-18 as well as tumor necrosis factor alpha. Small amounts of nitric oxide released cyclically from endothelial nitric oxide synthase also inhibit activity of inducible nitric oxide synthase. This enzyme produces large amounts of nitric oxide over prolonged time intervals to form nitrogen free radicals (Leng S., Chaves P., Koenig K., Walston J., *Serum interleukin-*6 *and hemoglobin as physiological correlates in the geriatric syndrome of frailty: a pilot study,* J. Am. Geriatr. Soc., 50:1268–71 (2002); Beauparlant P., Hiscott J., *Biological and biochemical inhibitors of the NF-kappa B/Rel proteins and cytokine synthesis,* Cytokine Growth Factor Rev., 7:175–90 (1996); Stefano G. B., Prevot V., Cadet P., Dardik I., *Vascular pulsations stimulating nitric oxide release during cyclic exercise may benefit health: a molecular approach* (*review*), Int. J. Mol. Med., 7:119–29 (2001)).

In addition to the immunosuppressant action of nitric oxide released from endothelial nitric oxide synthase with periodic acceleration, this treatment modality also preferentially increases distributes blood flow to the gastrointestinal tract, liver, and kidneys whereas exercise diminishes blood flow to these sites (Adams J. A., Mangino M. J., Bassuk J., Kurlansky P., Sackner M. A., *Regional blood flow during periodic acceleration,* Crit Care Med., 29:1983–88 (2001); Manohar M., Goetz T. E., Saupe B., Hutchens E., Coney E., *Thyroid, renal, and splanchnic circulation in horses at rest and during short-term exercise,* Am. J. Vet. Res. 56:1356–61 (1995)). This effect of periodic acceleration may be of importance in the management of colic in horses.

Periodic acceleration with release of nitric oxide from endothelial nitric oxide synthase from osteoblasts in the bone as from blood vessels in the bones aids in bone healing from fractures and prevents nonunion (Corbett S. A., Hukkanen M., Batten J., McCarthy I. D., Polak J. M., Hughes S. P., *Nitric oxide in fracture repair. Differential localisation, expression and activity of nitric oxide synthases,* J. Bone Joint Surg. Br., 81:531–37 (1999)). The stress of osteoarthritis causes release of nuclear factor kappa beta from chondrocytes and synovial fibroblasts that in turn can cause release of IL-1 and metalloproteinases (Alwan W. H., Carter S. D., Dixon J. B., Bennett D., May S. A., Edwards G. B., *Interleukin-*1*-like activity in synovial fluids and sera of horses with arthritis,* Res. Vet. Sci. 51:72–77 (1991); Elliott S. F., Coon C. I., Hays E., Stadheim T. A., Vincenti M. P., *Bcl-*3 *is an interleukin-*1*-responsive gene in chondrocytes and synovial fibroblasts that activates transcription of the matrix metalloproteinase* 1 *gene,* Arthritis Rheum., 46:3230–39 (2002)). Periodic acceleration through release of nitric oxide from endothelial nitric oxide synthase suppresses nuclear factor kappa beta that in turn suppresses both IL-1 and metalloproteinases.

Periodic acceleration with release of nitric oxide from endothelial nitric oxide synthase serves to precondition the horse from the ischemia of the gastrointestinal tract associated colic (Pajdo R., Brzozowski T., Konturek P. C., Kwiecien S., Konturek S. J., Sliwowski Z. et al., *Ischemic preconditioning, the most effective gastroprotective intervention: involvement of prostaglandins, nitric oxide, adenosine and sensory nerves,* Eur. J. Pharmacol., 427: 263–76 (2001); Hotter G., Closa D., Prados M., Fernandez-Cruz L., Prats N., Gelpi E. et al., *Intestinal preconditioning is mediated by a transient increase in nitric oxide,* Biochem. Biophys. Res. Commun., 222:27–32 (1996); Ogawa T., Nussler A. K., Tuzuner E., Neuhaus P., Kaminishi M., Mimura Y. et al., *Contribution of nitric oxide to the protective effects of ischemic preconditioning in ischemia-reperfused rat kidneys,* J. Lab Clin. Med., 138:50–58 (2001); Vlasov T. D., Smirnov D. A., Nuffullina G. M., *Preconditioning of the small intestine to ischemia in rats,* Neurosci. Behav. Physiol., 32:449–53 (2002)). During colic, nitric oxide released with periodic acceleration would suppress the inflammatory cytokines as well as tumor necrosis factor and activity of inducible nitric oxide synthase. These molecules account for the tissue destructive effects of colic.

Exercise-induced pulmonary hemorrhage is associated with an inflammatory response at the affected site. The latter produces fibrosis and further weakening of pulmonary capillaries that allows blood to leak through them during racing or training sessions. With repeated strenuous exercise, either in training or actual competition, the hemorrhage results in fibrosis/scarring, a weakened blood gas barrier and sustained inflammation. The blood within the alveoli may adversely affect lung health and exercise capacity by interfering with gas exchange. EIPH often worsens with repeated exercise and increased age. Thus, periodic acceleration would prevent the occurrence of worsening of the condition. Further, in those horses in which inflammation is an important contributory cause to EIPH, periodic acceleration serves as treatment.

Since heaves in horses are analogous to human bronchial asthma and repetitive episodes produce a situation analogous to chronic obstructive pulmonary disease, treatment with periodic acceleration is both preventative and therapeutic. The effectiveness related to nitric oxide release from endothelial nitric oxide synthase suppressing activities of nuclear factor kappa beta and inducible nitric oxide synthase.

Figure 34:
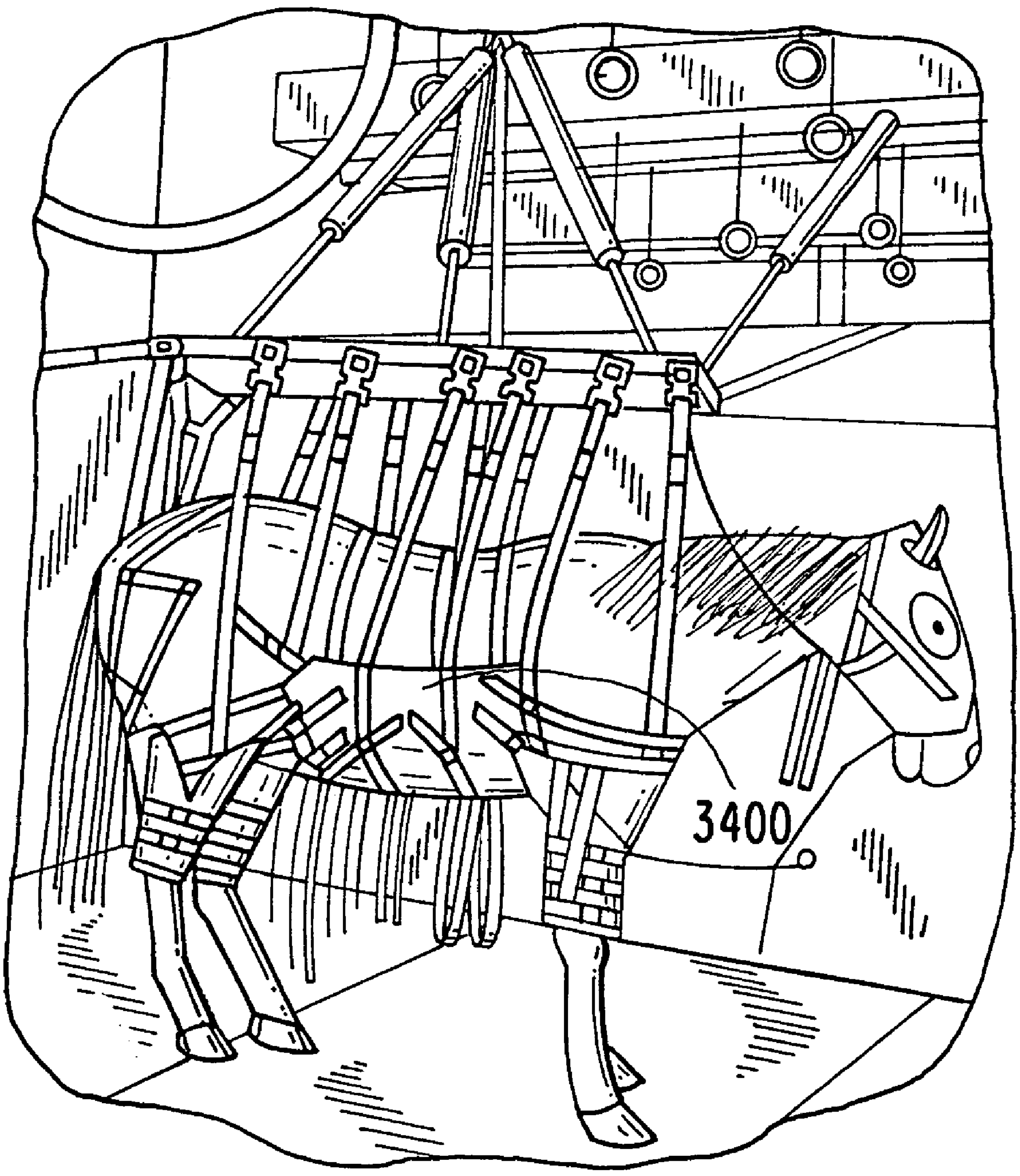
FIG. 34 is a picture of a horse in a UC Davis-Anderson sling.

Application of periodic acceleration to the horse can be carried out in two ways. The body of the horse could be lowered with a UC Davis-Anderson sling (shown in FIG. 34) into the frame attached to the motion platform such that his torso would be supported on an additional cloth sling attached to the frame (shown in FIG. 35). FIG. 34 depicts the UC Davis-Anderson sling placed around a horse. The sling is used primarily for supporting non-ambulatory horses, often after major orthopedic surgery requiring that the patient be non-weight bearing until healing has occurred. The sling was developed with an overhead hydraulic device for long-term rehabilitation cases and for recovery from anesthesia. The hydraulic system is able to take the weight off any one or all four legs.

Figure 35:
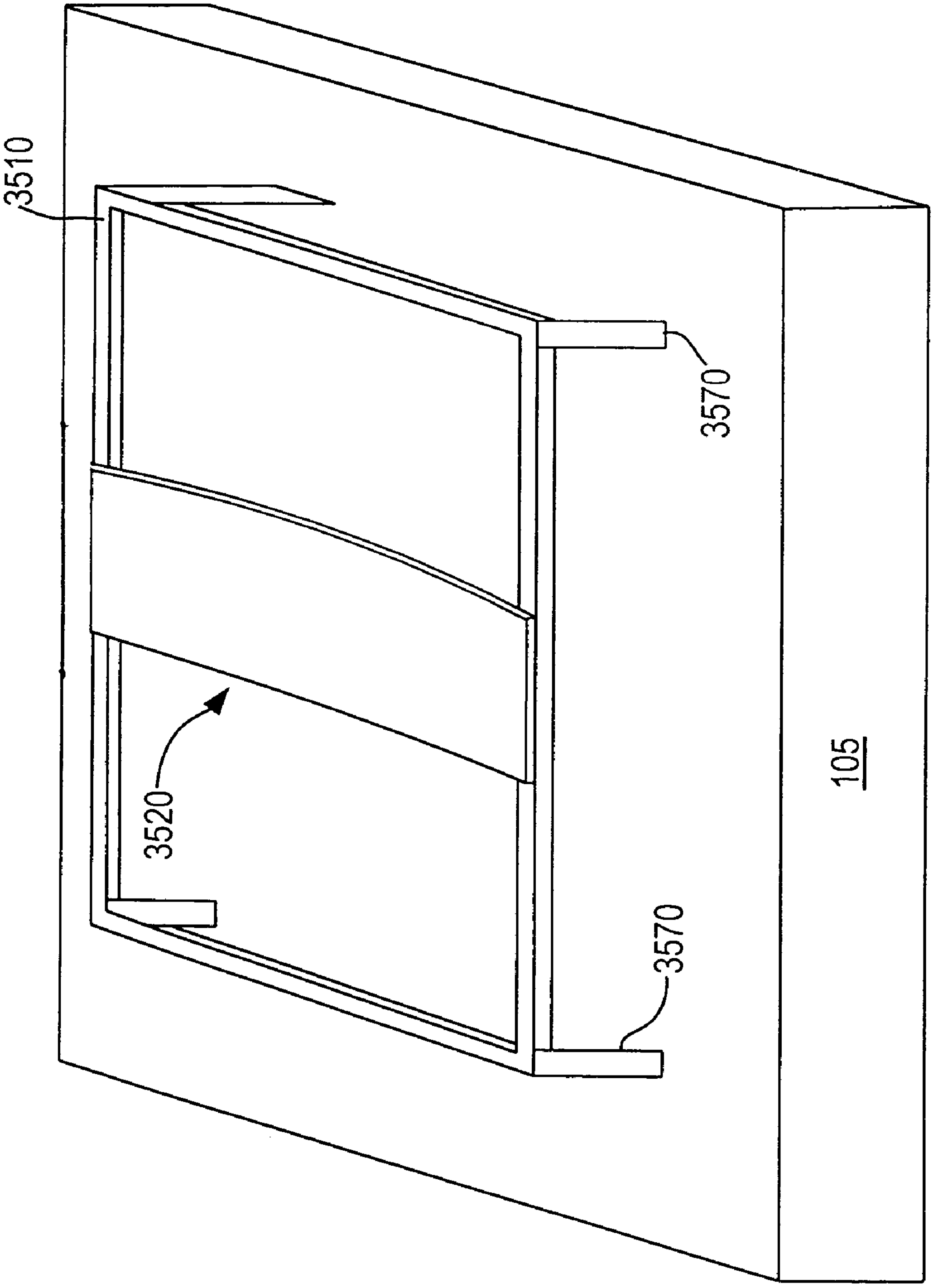
FIG. 35 is a schematic drawing of an apparatus for providing periodic acceleration to a horse according to a preferred embodiment of the present invention.

FIG. 35 is a conceptual schematic drawing, not drawn to scale, showing how a horse might be coupled to the motion platform. The body of the horse could be lowered with a UC Davis-Anderson sling 3400 shown in FIG. 34. In FIG. 35, the frame 3510 is attached to the motion platform such that his torso would be supported on an additional cloth sling 3520 attached to the frame 3510. The legs 3750 of frame 3510 would support the horse in sling 3520. The hoofs would be slightly above the surface 105 of the motion platform not touching or lightly touching it. Periodic acceleration could then be applied to the body while the UC Davis-Anderson sling remains in place. In a modification of this invention, the sling would be placed underneath the ventral torso of the horse and then attached to the frame. The legs of the frame would be telescoping and lifted upward by pneumatic, hydraulic or electrical motor powered assemblies such that the horse is supported by the sling of the frame that in turn is coupled to the motion platform.

E. Treatment of Diseases Where Oxidative Stress Plays a Role

Background

Reactive oxygen species (ROS) are generated by 1) environmental sources, for example, photo-oxidations and emissions and 2) normal cellular functions such as mitochondrial metabolism and neutrophil activation. ROS include 1) free radicals, superoxide and hydroxyl radicals, 2) nonradical oxygen species such as hydrogen peroxide and peroxynitrite and 3) reactive lipids and carbohydrates, for example, ketoaldehydes, hydroxynonenal. Oxidative damage to DNA can occur by many routes including the oxidative modification of the nucleotide bases, sugars, or by forming crosslinks. Such modifications can lead to mutations, pathologies, cellular aging and death. Oxidation of proteins appears to play a causative role in many chronic diseases of aging including cataractogenesis, rheumatoid arthritis, and various neurodegenerative diseases including Alzheimer's Disease (AD) (Gracy R. W., Talent J. M., Kong Y., Conrad C. C., *Reactive oxygen species: the unavoidable environmental insult?* Mutat. Res., 428:17–22 (1999)).

Oxidative stress results from an oxidant/antioxidant imbalance, an excess of oxidants and/or a depletion of antioxidants. Although activated leucocytes are rich in reactive oxygen species (ROS), other cells in the body can release ROS in response to a stress. Oxidative stress plays an important role in the pathogenesis of a number of lung diseases, through direct injurious effects and by involvement in the molecular mechanisms that control lung inflammation. Several studies have shown an increased oxidant burden and consequently increased markers of oxidative stress in the airspaces, breath, blood, and urine in smokers, COPD, cystic fibrosis, and asthma. Important consequences of oxidative stress for the pathogenesis of COPD include oxidative inactivation of antiproteinases, airspace epithelial injury, increased sequestration of neutrophils in the pulmonary microvasculature, and gene expression of inflammatory cytokines. Oxidative stress has a role in enhancing the inflammation that occurs in smokers, COPD, cystic fibrosis and asthma, through the activation of redox-sensitive transcriptions factors such as nuclear factor kappa beta and activator protein-1, which regulate the genes for inflammatory cytokines and protective antioxidant gene expression.

The sources of the increased oxidative stress in patients with COPD are derived from the increased burden of oxidants present in cigarette smoke, or from the increased amounts of reactive oxygen species released from leukocytes, both in the airspaces and in the blood. Environmental air pollution from high levels of atmospheric ozone produce oxidative stress. Antioxidant depletion or deficiency in antioxidants may contribute to oxidative stress (MacNee W., *Oxidants/antioxidants and COPD.* Chest, 117:303S–17S (2000); Rahman I., *Oxidative stress, chromatin remodeling and gene transcription in inflammation and chronic lung diseases.* J. Biochem. Mol. Biol., 36:95–109 (2003); Bowler R. P., Crapo J. D., *Oxidative stress in airways: is there a role for extracellular superoxide dismutase?* Am. J. Respir. Crit Care Med., 166:S38–S43 (2002); Kinney P. L., Nilsen D. M., Lippmann M., Brescia M., Gordon T., McGovern T. et al., *Biomarkers of lung inflammation in recreational joggers exposed to ozone,* Am. J. Respir. Crit Care Med., 154: 1430–35 (1996)). Hyperbaric oxygen treatments and hard-hat deep diving produce oxidative stress (Speit G., Dennog C., Radermacher P., Rothfuss A., *Genotoxicity of hyperbaric oxygen,* Mutat. Res., 512:111–19 (2002); Bearden S. E., Cheuvront S. N., Ring T. A., Haymes E. M., *Oxidative stress during a 3.5-hour exposure to 120 kPa (a) PO2 in human divers,* Undersea Hyperb. Med., 26:159–64 (1999)). Oxidative stress is found in allergic rhinitis (Bowler R. P., Crapo J. D., *Oxidative stress in allergic respiratory diseases,* J. Allergy Clin. Immunol., 110:349–56 (2002)). Both oxidative stress and increase of inflammatory cytokines are found in Asbstosis (Kamp D. W., Weitzman S. A., *Asbestosis: clinical spectrum andpathogenic mechanisms,* Proc. Soc. Exp. Biol. Med., 214:12–26 (1997)).

In addition to pulmonary diseases, there are several diseases or conditions in which oxidative stress has a major role usually with a co-existing inflammatory response. Oxidative stress is a prominent feature neurological diseases such as Alzheimer's disease, Parkinson's disease, supranuclear palsy, amyotrophic lateral sclerosis, motor neuron disease, HIV dementia, Huntington's chorea, Friedrich's ataxia, stroke, obstructive sleep apnea syndrome, and cognitive impairment in the elderly (Albers D. S., Augood S. J., *New insights into progressive supranuclear palsy,* Trends Neurosci., 24:347–53 (2001); Berr C., *Oxidative stress and cognitive impairment in the elderly,* J. Nutr. Health Aging, 6:261–66 (2002); Jenner P., *Oxidative stress in Parkinson's disease,* Ann. Neurol., 53:S26–S38 (2003); Lavie L., *Obstructive sleep apnoea syndrome—an oxidative stress disorder.* Sleep Med. Rev., 7:35–51 (2003); Mohanakumar K. P., Thomas B., Sharma S. M., Muralikrishnan D., Chowdhury R., Chiueh C. C., *Nitric oxide: an antioxidant and neuroprotector,* Ann. N.Y. Acad. Sci., 962:389–401 (2002); Pong K., *Oxidative stress in neurodegenerative diseases: therapeutic implications for superoxide dismutase mimetics.* Expert. Opin. Biol. Ther., 3:127–39 (2003); Puccio H., Koenig M., *Friedreich ataxia: a paradigm for mitochondrial diseases.* Curr. Opin. Genet. Dev. 12:272–77 (2002); Turchan J., Pocernich C. B., Gairola C., Chauhan A., Schifitto G., Butterfield D. A. et al., *Oxidative stress in HIV demented patients and protection ex vivo with novel antioxidants,* Neurology, 60:307–14 (2003)). Oxidative stress also plays a major role in muscular dystrophies (Rando T. A., *Oxidative stress and the pathogenesis of muscular dystrophies,* Am. J. Phys. Med. Rehabil., 81:S175–S186 (2002)).

Oxidative stress is the major pathogenic factor in reflux esophagitis (Oh T. Y., Lee J. S., Ahn B. O., Cho H., Kim W. B., Kim Y. B. et al., *Oxidative damages are critical in pathogenesis of reflux esophagitis: implication of antioxidants in its treatment.* Free Radic. Biol. Med., 30:905–15 (2001)). Helicobacter pylori infection induces infiltration of the gastric mucosa by polymorphonuclear cells and macrophages, as well as T and B lymphocytes. Paradoxically, this robust immune/inflammatory response cannot clear the infection, and thus leaves the host prone to complications resulting from chronic inflammation and oxidative stress. NSAID's may also cause gastric injury leading to inflammation and oxidative stress. An adverse consequence of the responses to helicobacter pylori infection and NSAID's may be the development of gastric cancer (Ernst P., *Review article: the role of inflammation in the pathogenesis of gastric cancer.* Aliment. Pharmacol. Ther., 13 Suppl 1:13–18 (1999); Yoshikawa T., Naito Y., *The role of neutrophils and inflammation in gastric mucosal injury,* Free Radic. Res., 33:785–94 (2000)).

Oxidative stress is a major component of inflammatory bowel disease (Kruidenier L., Verspaget H. W., *Review article: oxidative stress as a pathogenic factor in inflammatory bowel disease—radicals or ridiculous?* Aliment.

Pharmacol. Ther. 16:1997–2015 (2002)). Oxidative stress plays an important role in the development of alchoholic liver disease (Albano E., *Free radical mechanisms in immune reactions associated with alcoholic liver disease,* Free Radic. Biol. Med., 32:110–14 (2002)).

Oxidative stress is important for the pathology of atherosclerosis, hypertension, chronic heart failure, chronic renal failure, diabetes mellitus, dyslipidemias, hyperhomocystinuria, restenosis of coronary vessels, ischemia-perfusion injury, endothelial dysfunction, endometriosis, vein graft failure, and cardiopulmonary bypass surgery (Alameddine F. M., Zafari A. M., *Genetic polymorphisms and oxidative stress in heart failure.* Congest. Heart Fail., 8:157–64, 172 (2002); Annuk M., Zilmer M., Fellstrom B., *Endothelium-dependent vasodilation and oxidative stress in chronic renal failure: Impact on cardiovascular disease,* Kidney Int. Suppl., 50–53 (2003); Jeremy J. Y., Yim A. P., Wan S., Angelini G. D., *Oxidative stress, nitric oxide, and vascular disease,* J. Card Surg., 17:324–27 (2002); Kaminski K. A., Bonda T. A., Korecki J., Musial W. J., *Oxidative stress and neutrophil activation—the two keystones of ischemialreperfusion injury,* Int. J. Cardiol., 86:41–59 (2002); Matata B. M., Sosnowski A. W., Galinanes M., *Off-pump bypass graft operation significantly reduces oxidative stress and inflammation,* Ann. Thorac. Surg., 69:785–91 (2000); Santanam N., Song M., Rong R., Murphy A. A., Parthasarathy S., *Atherosclerosis, oxidation and endometriosis,* Free Radic. Res., 36:1315–21 (2002)).

Ionizing radiation produces oxidative stress (Riley P. A., *Free radicals in biology: oxidative stress and the effects of ionizing radiation.* Int. J. Radiat. Biol., 65:27–33 (1994)). Oxidative stress is found in atopic dermitis, contact dermatitis, and psoriasis (Fuchs J, Zollner T M, Kaufmann R, Podda M., *Redox-modulated pathways in inflammatory skin diseases,* Free Radic. Biol. Med. 30:337–53 (2001)). Oxidative stress occurs in rheumatoid arthritis (Gracy R. W., Talent J. M., Kong Y., Conrad C. C., *Reactive oxygen species: the unavoidable environmental insult?* Mutat. Res., 428:17–22 (1999)).

Ageing is associated with onset of a chronic inflammatory state that includes the following predisposing factors. These consist of increased oxidative stress, a decrease in ovarian function, a decrease in stress-induced glucocorticoid sensitivity of pro-inflammatory cytokine production in men, and an increased incidence of asymptomatic bacteriuria. Obesity induces chronic inflammation. Inflammation is a key factor in the progressive loss of lean tissue and impaired immune function observed in ageing. Polymorphisms in the promoter regions of pro- and anti-inflammatory cytokine genes influence the level of cytokine production and the ageing process. Thus, a genotype for high pro-inflammatory cytokine production results in high cytokine production and may accelerate the rate of tissue loss. Conversely, polymorphisms in the genes for anti-inflammatory cytokines may result in a slowing of tissue loss. In the healthy aged male population, the former polymorphisms are under-represented and the lafter over-represented, indicating a genetically determined survival advantage in maintaining inflammation at a low level. The increased levels of chronic inflammation during ageing play a major role in the decline in immune function and lean body mass. The pro- and anti-inflammatory cytokine genotype is linked negatively and positively, respectively, with life-span, because of its influence on inflammation.

Mitochondria not only produce less ATP, but they also increase the production of reactive oxygen species (ROS) as by-products of aerobic metabolism in the aging tissues of the human and animals. It is now generally accepted that aging-associated respiratory function decline can result in enhanced production of ROS in mitochondria. Moreover, the activities of free radical-scavenging enzymes are altered in the aging process. The concurrent age-related changes of these two systems result in the elevation of oxidative stress in aging tissues. Within a certain concentration range, ROS may induce stress response of the cells by altering expression of respiratory genes to uphold the energy metabolism to rescue the cell. However, beyond the threshold, ROS may cause a wide spectrum of oxidative damage to various cellular components to result in cell death or elicit apoptosis by induction of mitochondrial membrane permeability transition and release of apoptogenic factors such as cytochrome c (Grimble R. F., *Inflammatory response in the elderly,* Curr. Opin. Clin. Nutr. Metab Care, 6:21–29 (2003); Wei Y. H., Lee H. C., *Oxidative stress, mitochondrial DNA mutation, and impairment of antioxidant enzymes in aging,* Exp. Biol. Med. (Maywood.), 227:671–82 (2002)).

Use of Periodic Acceleration for Treatment of Oxidative Stress

Periodic acceleration causes release of small quantities of nitric oxide (nMol/L) from endothelial nitric oxide synthase (eNOS). This scavenges reactive oxygen species (ROS) thereby diminishing or eliminating oxidative stress (Stefano G. B., Prevot V., Cadet P., Dardik I., *Vascular pulsations stimulating nitric oxide release during cyclic exercise may benefit health: a molecular approach* (*review*), Int. J. Mol. Med., 7:119–29 (2001); Joshi M. S., Ponthier J. L., Lancaster J. R., Jr. *Cellular antioxidant and pro-oxidant actions of nitric oxide,* Free Radic. Biol. Med., 27:1357–66 (1999)).

The invention is not limited by the embodiments described above which are presented as examples only but can be modified in various ways within the scope of protection defined by the appended patent claims. Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A motion platform for providing periodic acceleration to a living subject, comprising:

a box frame providing a foundation of the motion platform;

a drive module adjoining said box frame, said drive module operably movable relative to said box frame; and a support connected to said drive module, said support comprising a planar surface for supporting the subject, said planar surface having a head end and a foot end;

wherein said drive module comprises a displacement module for inducing periodic acceleration to the subject by moving the drive module in a line parallel to the planar surface of the support, and the periodic acceleration is alternately in the direction of the head end, and the foot end, of the planar surface, whereby the motion platform adds pulses to fluid filled channels of the body of the subject, the displacement module being connected to said box frame only through said drive module, whereby said displacement module is not directly connected to said box frame.

2. The motion platform of claim 1, further comprising: a mattress attached to the support for the subject to lie on.

3. The motion platform of claim 1, wherein the movement has a rate of substantially 100–200 cpm and a force in a range of about 0.09 to 0.35 g.

4. The motion platform of claim 1, wherein the provided periodic acceleration release of nitric oxide from the vascular endothelium of the subject through activation of endothelial nitric oxide synthase (eNOS) that in turn suppresses the transcriptional gene, nuclear factor kappa beta, thereby suppressing formation of inflammatory cytokines, tumor necrosis factor, adhesion molecules, inducible nitric oxide synthase (iNOS) activity, and endothelin-1 release.

5. The motion platform of claim 4, wherein the immunosuppressant effects are utilized to treat at least one of Alzheimer's disease, anaphylaxis, ankylosing spondylitis, asthma, atherosclerosis, chronic obstructive pulmonary disease, Crohn's disease, gout, Hashimoto's thyroiditis, ischemic-reperfusion injury (occlusive and embolic stroke attacks and myocardial infarction), multiple sclerosis, osteoarthritis, pemphigus, periodic fever syndrome, psoriasis, rheumatoid arthritis, sarcoidosis, systemic lupus erythematosis, Type 1 diabetes mellitus, ulcerative colitis, vasculitides (Wegener's syndrome, Goodpasture's syndrome, giant cell arteritis, polyarteritis nodosa), xenograft rejection, bacterial dysentery, Chagas disease, cystic fibrosis pneumonia, filiarisis, heliobacter pylori gastritis, hepatitis C, influenza virus pneumonia, leprosy, neisseria or pneumococcal meningitis, post-streptococcal glomerulonephritis, sepsis syndrome, tuberculosis, bleomycin-induced pulmonary fibrosis, chronic allograft rejection, idiopathic pulmonary fibrosis, hepatic cirrhosis (post-viral or alcoholic), radiation-induced pulmonary fibrosis, schistosomiasis, peripheral vascular disease, coronary artery disease, angina pectoris, restenosis after relief of stenosis, arteriosclerotic plaque rupture, stroke, chronic venous insufficiency, cardiopulmonary bypass surgery, chronic heart failure, amyotrophic lateral sclerosis, myasthenia gravis, Huntington's chorea, Parkinson's disease, fibromyalgia, chronic fatigue syndrome, complex regional pain syndrome, muscular dystrophy, myopathy, obstructive sleep apnea syndrome, cerebral palsy, neuropathy, HIV dementia, head trauma/coma, atopic dermatitis, urticarias, pressure ulcers, burns, Behcet's disease, injuries, sprains, intervertebral disc disorder, sciatica, dislocations, fractures, carpal tunnel syndrome, the geriatric syndrome of frailty, endometriosis acute myeloblastic leukemia, melanoma, lung cancer, myelidysplastic syndrome, multiple myeloma, Kaposi's sarcoma in conjunction with HIV-1, Hodgkin's disease, cancer-related fatigue, hemolytic anemias such as sickle cell disease, hemolytic-uremic syndrome, and thalassemia have strong inflammatory components, depression, autism, and schizophrenia, allergic rhinitis, nasal and sinus polyps, and chronic sinusitis, smoking, chronic bronchitis, bronchiectasis, pneumoconiosis, adult respiratory distress syndrome (ARDS), severe acute respiratory syndrome (SARS), smoke burn inhalation injury to the lungs, inflammatory response due to overinflation of the lungs by mechanical ventilation, aseptic loosening of total hip replacement, aseptic necrosis of the hip, injury to donor organs due to brain death of the donor, periodontal disease, severe systemic inflammation with a vasodilatory syndrome after cardiopulmonary bypass for open heart surgery, repeated deep breathing of cold air, and cellulite.

6. The motion platform of claim 4, wherein the immunosuppressant and the scavenging of reactive oxygen and nitrogen species effects are utilized to slow the non-genetic components of the ageing process.

7. The motion platform of claim 4, wherein the provided periodic acceleration provides better viability for donor organs intended for use in transplantation.

8. The motion platform of claim 4, wherein the provided periodic acceleration prevents the pulmonary inflammation associated with mechanical ventilation.

9. The motion platform of claim 4, wherein the provided periodic acceleration serves as treatment for Severe Acute Respiratory Syndrome (SARS).

10. The motion platform of claim 4, wherein the provided periodic acceleration serves as treatment for severe systemic inflammation with a vasodilatory syndrome after cardiopulmonary bypass, open-heart surgery.

11. The motion platform of claim 4, wherein treatment using the provided periodic acceleration replaces the use of corticosteroids and non-steroidal anti-inflammatory drugs (NSAID's) in management of inflammatory diseases.

12. The motion platform of claim 4, wherein the provided periodic acceleration provides cumulative effectiveness in treatment of inflammatory diseases.

13. The motion platform of claim 1, wherein the provided periodic acceleration administered once or twice daily serves as protection against inflammatory processes that occur episodically.

14. The motion platform of claim 13, wherein the episodic inflammatory processes comprise asthma, exercising in cold air, the subject's condition prior to cardiopulmonary bypass surgery, allergic rhinitis, and mental stress.

15. The motion platform of claim 1, wherein the provided periodic acceleration is used to prevent failure of prosthetic hip replacements.

16. The motion platform of claim 1, wherein the provided periodic acceleration is used to treat cellulite.

17. The motion platform of claim 1, wherein the provided periodic acceleration serves as a means for at least one of preconditioning, conditioning and postconditioning tissues of the body to events that are associated with at least one of impaired blood supply and delivery of oxygen to the tissues.

18. The motion platform of claim 17, wherein the provided periodic acceleration preconditions the heart, brain, kidneys, lungs, gastrointestinal tract, liver and pancreas in patients when administered prior to cardiopulmonary bypass surgery.

19. The motion platform of claim 17, wherein the provided periodic acceleration preconditions the heart, brain, kidneys, lungs, gastrointestinal tract, liver and pancreas during ascent to high altitude.

20. The motion platform of claim 17, wherein the provided periodic acceleration preconditions the lungs of the subject for a case of deep venous thrombosis.

21. The motion platform of claim 17, wherein the provided periodic acceleration preconditions the heart, brain, kidneys, lungs, gastrointestinal tract, liver and pancreas in a subject who has atrial fibrillation/flutter and in whom cardioversion is indicated.

22. The motion platform of claim 17, wherein the provided periodical acceleration conditions at least one of:

the heart during cardiopulmonary resuscitation, acute myocardial infarction, and unstable angina;

the brain during an acute stroke;

the lungs during pulmonary embolism/thrombosis;

the brain, kidneys, gastrointestinal tract, liver and pancreas during an arterial embolism; and the heart, brain, kidneys, lungs, gastrointestinal tract, liver and pancreas during sepsis, shock and hypotension states.

23. The motion platform of claim 17, wherein the provided periodical acceleration postconditions at least one of:

the brain after an acute stroke;

the lungs after pulmonary embolism/thrombosis;

the heart, brain, kidneys, lungs, gastrointestinal tract, liver and pancreas while the subject is recovering from sepsis, shock, and hypotension states;

the heart, brain, kidneys, lungs, gastrointestinal tract, liver and pancreas while the subject is at a high altitude; and the heart, brain, kidneys, lungs, gastrointestinal tract, liver, pancreas, and skeletal muscles before the subject engages in physical activity in order to enhance physical performance.

24. The motion platform of claim 1, wherein the provided periodic acceleration causes release of nitric oxide from the vascular endothelium through activation of endothelial nitric oxide synthase (eNOS) that in turn scavenges reactive oxygen species thereby diminishing or eliminating oxidative stress.

25. The motion platform of claim 24, wherein the release of small quantities of nitric oxide from endothelial nitric oxide synthase causes antioxidant activity which treats and prevents the diseases and conditions that have oxidative stress as a major component.

26. The motion platform of claim 25, wherein the diseases and conditions that have oxidative stress as a major component comprise one of: smoking, environmental pollution, cystic fibrosis, asthma, Alzheimer's disease, Parkinson's disease, supranuclear palsy, amyotrophic lateral sclerosis, motor neuron disease, HIV dementia, Huntington's chorea, Friedrich's ataxia, stroke, obstructive sleep apnea syndrome, cognitive impairment in the elderly, muscular dystrophy, reflux esophagitis, Helicobacter pylori infection, inflammatory bowel disease, alchoholic liver disease, atherosclerosis, hypertension, chronic heart failure, chronic renal failure, diabetes mellitus, dyslipidemias, hyperhomocystinuria, restenosis of coronary vessels, ischemia-perfusion injury, endothelial dysfunction, endometriosis, vein graft failure, cardiopulmonary bypass surgery, ionizing radiation, atopic dermitis, contact dermatitis, psoriasis, and rheumatoid arthritis.

27. The motion platform of claim 1, wherein the periodic acceleration produces antioxidant activity thereby slowing the ageing process.

28. The motion platform of claim 26, wherein the periodic acceleration is administered prior to exposure to oxidative stress from environmental sources in order to prevent deleterious effects.

29. The motion platform of claim 28, wherein the environmental sources causing oxidative stress comprise at least one of hyperbaric oxygen treatments, hard-hat diving, and excessive atmospheric ozone.

30. The motion platform of claim 3, wherein the movement has a rate of substantially 120–180 cpm and a force in a range of about 0.2 to 0.25 g.

31. The motion platform of claim 30, wherein the periodic acceleration is provided at a rate of about 120 cpm with a force of about 0.15 g. in order to provide as gentle a treatment as possible while still having a therapeutic effect.

32. The motion platform of claim 1, wherein said support further comprises a footboard connected at the foot end of the planar surface, said footboard rising perpendicularly to the planar surface and having cast shoes for securing the feet of the subject to the support.

33. The motion platform of claim 32, wherein the cast shoes are rigidly attached to the footboard with nuts and bolts.

34. The motion platform of claim 32, wherein the cast shoes are comprised of a solid material in the form of boots with a soft lining on the inside.

35. The motion platform of claim 34, wherein each of the solid boots are comprised of two parts, and wherein the parts are capable of being separated and then locked together so that the feet of the subject may be placed in the cast shoes and the secured within the cast shoes.

36. The motion platform of claim 32, wherein the cast shoes are comprised of pliable material, and wherein the feet of the subject are secured in the cast shoes by partially or wholly enclosing the feet with at least two portions of the pliable material and connecting the at least two portions of the pliable material with a fastening means.

37. The motion platform of claim 36, wherein the fastening means is at least one of a hook and loop connection, a buckle connection, and a notch and detent connection.

38. The motion platform of claim 36, wherein the fastening means is at least one of a hook and loop connection, a buckle connection, and a notch and detent connection.

39. The motion platform of claim 1, wherein the provided periodic acceleration adds pulses to fluid filled channels of the body of the subject that do not entrain the subject's own pulse, whereby the number of pulses to which the fluid filled channels are exposed is increased, the added pulses being of sufficient frequency and strength to cause release of nitric oxide from the vascular endothelium of the subject through activation of endothelial nitric oxide synthase (eNOS).

40. The motion platform of claim 1, wherein the drive module comprises:

four track wheels located substantially at the four corners of the upper portion of the drive module;

wherein the drive module adjoins the box frame where the four track wheels of the drive module rest in four wheel tracks located on the upper portion of the box frame; and wherein the four wheels allow the head end-foot end motion of the drive module within the box frame, and the four wheel tracks limit said head end-foot end motion.

41. The motion platform of claim 1, wherein the drive module comprises a frame to which the support is connected and the displacement module comprises at least one pair of rotating counterweights being attached to said frame by a drive shaft, wherein both counterweights in the at least one pair rotate around the drive shaft in the same plane.

42. The motion platform of claim 2, further comprising a bolster to be placed above the mattress in a location such that it supports and raises the buttocks region of a supine subject or the pubic region of a prone subject and the mattress supports either the upper back of the supine subject, or the upper chest of the prone subject.

43. The motion platform of claim 1, further comprising:

a processing means for determining a position of the dicrotic notch of the subject's pulse wave; and an override means for overriding the movement of the motion platform when the pulse is distorted by the pulses added by the periodic acceleration.

44. The motion platform of claim 1, further comprising:

a processing means for computing an a/b ratio for the dicrotic notch position;

wherein the efficacy of the provided periodic acceleration in releasing nitric oxide into the circulation from upregulation of endothelial nitric oxide synthase (eNOS) may be measured.

45. A motion platform for providing periodic acceleration to a living subject, comprising:

a box frame providing a foundation of the motion platform:

a drive module adjoining said box frame, said drive module operably movable relative to said box frame; and a support connected to said drive module, said support comprising:

a planar surface for supporting the subject, said planar surface having a head end and a foot end; and a footboard connected at the foot end of the planar surface, said footboard rising perpendicularly to the planar surface and having cast shoes for securing the feet of the subject to the support;

wherein said drive module provides periodic acceleration to the subject by moving in a line parallel to the planar surface of the support while the subject is secured to said support by said cast shoes on said footboard, and the periodic acceleration is alternately in the direction of the head end, and the foot end, of the planar surface, whereby the motion platform adds pulses to fluid filled channels of the body of the subject, and wherein the drive module comprises:

four track wheels located substantially at the four comers of the upper portion of the drive module;

wherein the drive module adjoins the box frame where the four track wheels of the drive module rest in four wheel tracks located on the upper portion of the box frame; and wherein the four wheels allow the head end-foot end motion of the drive module within the box frame, and the four wheel tracks limit said head end-foot end motion.

46. A motion platform for providing periodic acceleration to a living subject comprising:

a box frame providing a foundation of the motion platform;

a drive module adjoining said box frame, said drive module operably movable relative to said box frame; and a support connected to said drive module, said support comprising:

a planar surface for supporting the subject, said planar surface having a head end and a foot end; and a footboard connected at the foot end of the planar surface, said footboard rising perpendicularly to the planar surface and having cast shoes for securing the feet of the subject to the support;

wherein said drive module provides periodic acceleration to the subject by moving in a line parallel to the planar surface of the support while the subject is secured to said support by said cast shoes on said footboard, and the periodic acceleration is alternately in the direction of the head end, and the foot end, of the planar surface, whereby the motion platform adds pulses to fluid filled channels of the body of the subject, and wherein the drive module comprises:

a frame to which the support is connected; and at least one pair of rotating counterweights being attached to said frame by a drive shaft, wherein both counterweights in the at least one pair rotate around the drive shaft in the same plane.

47. The motion platform of claim 46, wherein the at least one pair of counterweights comprises:

a first counterweight attached by a first arm to the drive shaft; and a second counterweight attached by a second arm to the drive shaft, wherein the second arm is longer than the first arm;

wherein the mass of the counterweights is such that the centrifugal force exerted by the first counterweight is substantially the same as the centrifugal force exerted by the second counterweight when the counterweights are rotating around the drive shaft.

48. The motion platform of claim 46, wherein the first counterweight rotates clockwise in the rotation plane around the drive shaft, and the second counterweight rotates counter-clockwise in the rotation plane around the drive shaft, and wherein a first point during rotation where the counterweights are aligned and a second point opposite from the first point during rotation where the counterweights are aligned are located such that a first line drawn from the drive shaft to the first point is in the direction of the head end and a second line drawn from the drive shaft to the second point is in the direction of the foot end;

whereby the centrifugal forces of the counterweights during rotation cancel each other except in the direction of the foot end and the head end.

49. The motion platform of claim 48, wherein the at least one pair of counterweights comprises:

a head end pair of counterweights located toward the head end of the frame and comprising a head end drive shaft and first and second head end counterweights; and a foot end pair of counterweights located toward the foot end of the frame and comprising a foot end drive shaft and first and second foot end counterweights.

50. The motion platform of claim 48, wherein the drive module further comprises:

a drive rotation motor for driving both the head end and foot end drive shafts; and a linear displacement motor for controlling a relative phase between the head end pair of counterweights and the foot end pair of counterweight, said relative phase being the timing relationship between when the front end counterweights align and when the head end counterweights align;

wherein said drive rotation motor controls the speed of the movement of the support, and said linear displacement motor controls an amount of force applied in the head end and foot end directions.

51. A motion platform for providing periodic acceleration to a living subject, comprising:

a box frame providing a foundation of the motion platform;

a drive module adjoining said box frame, said drive module operably movable relative to said box frame; and a support connected to said drive module, said support comprising:

a planar surface for supporting the subject, said planar surface having a head end and a foot end; and a footboard connected at the foot end of the planar surface, said footboard rising perpendicularly to the planar surface and having cast shoes for securing the feet of the subject to the support;

wherein said drive module provides periodic acceleration to the subject by moving in a line parallel to the planar surface of the support while the subject is secured to said support by said cast shoes on said footboard, and the periodic acceleration is alternately in the direction of the head end, and the foot end, of the planar surface, whereby the motion platform adds pulses to fluid filled channels of the body of the subject:

a mattress attached to the support for the subject to lie on; and a bolster to be placed above the mattress in a location such that it supports and raises the buttocks region of a supine subject or the pubic region of a prone subject and the mattress supports either the upper back of the supine subject, or the upper chest of the prone subject.

52. The motion platform of claim 51, wherein the bolster is adjustable, thereby allowing an operator to control an amount the bolster raises the body of the subject.

53. The motion platform of claim 51, wherein the provided periodic acceleration permits efficient, non-invasive ventilation because the subject's rib cage and abdomen move in phase.

54. The motion platform of claim 53, wherein the non-invasive ventilation is utilized in clinical situations where conventional positive and negative pressure mechanical ventilators are indicated.

55. The motion platform of claim 53, wherein the non-invasive ventilation is utilized in conjunction with conventional positive and negative pressure mechanical ventilators.

56. The motion platform of claim 53, wherein the non-invasive ventilation is utilized in patients requiring non-invasive nocturnal ventilation.

57. The motion platform of claim 53, wherein the non-invasive ventilation is utilized in patients who have the obstructive sleep or central sleep apneas to reduce the prevalence of apneas.

58. The motion platform of claim 53, wherein the non-invasive ventilation is utilized to cause release of beneficial mediators such as nitric oxide from vascular endothelium into the circulation.

59. The motion platform of claim 53, wherein the non-invasive ventilation replaces a mechanical ventilator, thereby protecting the subject from mechanical ventilator induced lung injury by inducing the production of nitric oxide, which, in turn, suppresses nuclear factor kappa beta which is related to mechanical ventilator induced lung injury.

60. The motion platform of claim 53, wherein the non-invasive ventilation is utilized to aid in the removal of retained bronchopulmonary secretions in a ventilation-independent subject.

61. The motion platform of claim 60, wherein the ventilation-independent subject is trained to relax with an opened glottis, thereby aiding in removal of the retained bronchopulmonary secretions.

62. A motion platform for providing periodic acceleration to a living subject, comprising:

a box frame providing a foundation of the motion platform;

a drive module adjoining said box frame, said drive module operably movable relative to said box frame; and a support connected to said drive module, said support comprising:

a planar surface for supporting the subject, said planar surface having a head end and a foot end; and a footboard connected at the foot end of the planar surface, said footboard rising perpendicularly to the planar surface and having cast shoes for securing the feet of the subject to the support;

wherein said drive module provides periodic acceleration to the subject by moving in a line parallel to the planar surface of the support while the subject is secured to said support by said cast shoes on said footboard, and the periodic acceleration is alternately in the direction of the head end, and the foot end, of the planar surface, whereby the motion platform adds pulses to fluid filled channels of the body of the subject;

a processing means for determining a position of the dicrotic notch of the subject's pulse wave; and an override means for overriding the movement of the motion platform when the pulse is distorted by the pulses added by the periodic acceleration.

63. A motion platform for providing periodic acceleration to a living subject, comprising:

a box frame providing a foundation of the motion platform;

a drive module adjoining said box frame, said drive module operably movable relative to said box frame; and a support connected to said drive module, said support comprising:

a planar surface for supporting the subject, said planar surface having a head end and a foot end; and a footboard connected at the foot end of the planar surface, said footboard rising perpendicularly to the planar surface and having cast shoes for securing the feet of the subject to the support;

wherein said drive module provides periodic acceleration to the subject by moving in a line parallel to the planar surface of the support while the subject is secured to said support by said cast shoes on said footboard, and the periodic acceleration is alternately in the direction of the head end, and the foot end, of the planar surface, whereby the motion platform adds pulses to fluid filled channels of the body of the subject;

a processing means for computing an a/b ratio for the dicrotic notch position;

wherein the efficacy of the provided periodic acceleration in releasing nitric oxide into the circulation from upregulation of endothelial nitric oxide synthase (eNOS) may be measured.

64. A motion platform for providing periodic acceleration to a living subject, comprising:

a box frame providing a foundation of the motion platform, said box frame having four wheel tracks located substantially at the four corners of the top portion of the box frame;

a drive module having four track wheels located substantially at the four corners of the top portion of the drive module, wherein said track wheels extend from the top portion of the drive module and rest in the wheel tracks of the box frame, whereby the drive module sits within the box frame and is operably movable relative to said box frame, and wherein the drive module comprises:

a frame with a head end and a foot end;

a head end pair of counterweights located toward the head end of the frame and attached to the frame by a head end drive shaft around which rotate first and second head end counterweights which share a first plane of rotation, wherein the first head end counterweight rotates in an opposite direction of the second head end counterweight such that their centrifugal forces cancel each other except in the direction of the head end and the foot end; and a foot end pair of counterweights located toward the foot end of the frame and attached to the frame by a foot end drive shaft around which rotate first and second foot end counterweights which share a second plane of rotation, wherein the first foot end counterweight rotates in an opposite direction of the second foot end counterweight such that their centrifugal forces cancel each other except in the direction of the head end and the foot end;

wherein the first plane of rotation is the same as the second plane of rotation; and a support connected to said drive module, said support comprising:

a planar surface for supporting the subject, said planar surface having a head end connected to the head end of the frame of the drive module, and a foot end connected to the foot end of the frame of the drive module; and a footboard connected at the foot end of the planar surface, said footboard rising perpendicularly to the planar surface and having cast shoes for securing the feet of the subject to the support;

wherein said drive module provides periodic acceleration to the subject by moving in a line parallel to the planar surface of the support while the subject is secured to said support by said cast shoes on said footboard, and the periodic acceleration is alternately in the direction of the head end, and the foot end, of the planar surface, whereby the motion platform adds pulses to fluid filled channels of the body of the subject.

* * * * *

UNITED STATES PATENT AND TRADEMARK OFFICE

CERTIFICATE OF CORRECTION

PATENT NO. : 7,111,346 B2 
APPLICATION NO. : 10/439957
DATED : September 26, 2006
INVENTOR(S) : D. Michael Inman It is certified that error appears in the above-identified patent and that said Letters Patent is hereby corrected as shown below:

Col. 10, line 15, should read:

-- scriptional factor that is ubiquitously present in the body's --

Col. 35, line 21, should read:

-- the transcriptional factor, nuclear factor kappa beta, thereby --

Signed and Sealed this

Ninth Day of January, 2007

JON W. DUDAS
*Director of the United States Patent and Trademark Office*